United States Patent [19]

Adams et al.

[11] Patent Number: 5,780,709
[45] Date of Patent: Jul. 14, 1998

[54] TRANSGENIC MAIZE WITH INCREASED MANNITOL CONTENT

[75] Inventors: Thomas R. Adams, North Stonington, Conn.; Paul C. Anderson, West Des Moines, Iowa; Richard J. Daines, Ledyard, Conn.; William Gordon-Kamm, Urbandale, Iowa; Albert P. Kausch, Stonington, Conn.; Michael T. Mann, Mystic, Conn.; Peter M. Orr, Pawcatuck, Conn.; David C. Warner, Wakefield, R.I.

[73] Assignee: Dekalb Genetics Corporation, Dekalb, Ill.

[21] Appl. No.: 594,861

[22] Filed: Jan. 19, 1996

Related U.S. Application Data

[63] Continuation-in-part of Ser. No. 113,561, Aug. 25, 1993.

[51] Int. Cl.[6] .................. A01H 5/00; C12N 15/00; C12N 15/05
[52] U.S. Cl. .......... 800/205; 800/250; 800/DIG. 56; 435/172.3; 435/172.1; 435/424; 435/419; 536/24.1; 536/27.1; 935/52; 935/55; 935/67; 47/58; 47/DIG. 1
[58] Field of Search .............. 800/205, 250, 800/DIG. 56; 47/58, DIG. 1; 435/172.3, 69.1, 70.1, 72, 424, 419; 536/27.1, 24.1; 935/52, 55, 67, 88

[56] References Cited

U.S. PATENT DOCUMENTS

| | | | |
|---|---|---|---|
| 4,370,160 | 1/1983 | Ziemelis | 71/117 |
| 4,399,216 | 8/1983 | Axel et al. | 435/6 |
| 4,535,060 | 8/1985 | Comai | 435/172.3 |
| 4,559,301 | 12/1985 | Turner | 435/76 |
| 4,559,302 | 12/1985 | Ingolia | 435/172.3 |
| 4,581,847 | 4/1986 | Hibberd et al. | 47/58 |
| 4,634,665 | 1/1987 | Axel et al. | 435/68 |
| 4,642,411 | 2/1987 | Hibberd et al. | 800/1 |
| 4,665,030 | 5/1987 | Close | 435/240 |
| 4,666,844 | 5/1987 | Cheng | 435/240 |
| 4,683,202 | 7/1987 | Mullis | 435/91 |
| 4,727,028 | 2/1988 | Santerre et al. | 435/240.2 |
| 4,743,548 | 5/1988 | Crossway et al. | 435/172.3 |
| 4,761,373 | 8/1988 | Anderson et al. | 435/172.3 |
| 4,806,483 | 2/1989 | Wang | 435/240.49 |
| 4,940,835 | 7/1990 | Shah et al. | 800/205 |
| 4,971,908 | 11/1990 | Kishore et al. | 435/172.1 |
| 5,001,060 | 3/1991 | Peacock et al. | 435/172.3 |
| 5,004,863 | 4/1991 | Umbeck | 800/205 |
| 5,015,580 | 5/1991 | Christou et al. | 435/172.3 |
| 5,034,322 | 7/1991 | Rogers et al. | 435/172.3 |
| 5,049,500 | 9/1991 | Arnizen et al. | 435/172.3 |
| 5,094,945 | 3/1992 | Comai | 435/172.3 |
| 5,110,732 | 5/1992 | Benfey et al. | 435/172.3 |
| 5,134,074 | 7/1992 | Gordon et al. | 435/240.4 |
| 5,177,010 | 1/1993 | Goldman et al. | 435/172.3 |
| 5,187,073 | 2/1993 | Goldman et al. | 435/172.3 |
| 5,187,267 | 2/1993 | Comai et al. | 536/23.1 |
| 5,188,642 | 2/1993 | Shah et al. | 47/58 |
| 5,188,958 | 2/1993 | Moloney et al. | 435/240.4 |
| 5,250,515 | 10/1993 | Fuchs et al. | 514/12 |
| 5,254,799 | 10/1993 | DeGrave et al. | 800/205 |
| 5,258,300 | 11/1993 | Glassman et al. | 435/240.4 |
| 5,268,463 | 12/1993 | Jefferson | 536/23.7 |
| 5,290,924 | 3/1994 | Last et al. | 536/24.1 |
| 5,302,523 | 4/1994 | Coffee et al. | 435/172.1 |
| 5,350,689 | 9/1994 | Shillito et al. | 435/240.47 |
| 5,352,605 | 10/1994 | Fraley et al. | 435/240.4 |
| 5,371,003 | 12/1994 | Murry et al. | 435/172.3 |
| 5,405,765 | 4/1995 | Vasil et al. | 435/172.3 |
| 5,484,956 | 1/1996 | Lundquist et al. | 800/205 |
| 5,489,520 | 2/1996 | Adams et al. | 435/172.3 |
| 5,500,365 | 3/1996 | Fischhoff et al. | 435/240.4 |
| 5,550,318 | 8/1996 | Adams et al. | 800/205 |
| 5,561,236 | 10/1996 | Leemans et al. | 800/205 |
| 5,563,324 | 10/1996 | Tarczynski et al. | 800/205 |
| 5,589,616 | 12/1996 | Hoffman et al. | 800/205 |
| 5,591,616 | 1/1997 | Hiei et al. | 435/172.3 |

FOREIGN PATENT DOCUMENTS

| | | | |
|---|---|---|---|
| AU-B-80893/87 | 12/1988 | Australia | C12N 15/00 |
| 0 126 537 A2 | 4/1983 | European Pat. Off. | A61K 9/52 |
| 0 131 623 B1 | 1/1984 | European Pat. Off. | C12N 15/11 |
| 0 141 373 A3 | 5/1985 | European Pat. Off. | A01G 7/00 |
| 0 154 204 A2 | 9/1985 | European Pat. Off. | C12N 15/00 |
| 0 160 390 A2 | 11/1985 | European Pat. Off. | A01H 15/10 |
| 0 193 259 A1 | 9/1986 | European Pat. Off. | C12N 15/00 |
| 0 204 549 A2 | 10/1986 | European Pat. Off. | C12N 15/00 |
| 0 202 668 A2 | 11/1986 | European Pat. Off. | C12N 5/02 |
| 0 242 236 A1 | 10/1987 | European Pat. Off. | C12N 15/00 |
| 0 242 246 A1 | 11/1987 | European Pat. Off. | C12N 15/00 |
| 0 299 552 A1 | 1/1988 | European Pat. Off. | C12N 15/00 |
| 0 257 472 A2 | 3/1988 | European Pat. Off. | C12N 15/00 |
| 0 262 971 A2 | 5/1988 | European Pat. Off. | A01H 1/02 |
| 0 270 356 A2 | 6/1988 | European Pat. Off. | C12N 15/00 |
| 0 271 408 | 6/1988 | European Pat. Off. | C12N 15/00 |
| 0 275 069 A2 | 7/1988 | European Pat. Off. | C12N 15/00 |
| 0 280 400 A2 | 8/1988 | European Pat. Off. | A01C 1/06 |
| 0 282 164 A2 | 9/1988 | European Pat. Off. | C12N 5/00 |
| 0 289 479 A2 | 11/1988 | European Pat. Off. | C12N 15/00 |

(List continued on next page.)

OTHER PUBLICATIONS

Specification of U.S. Patent Application, Serial No. 07/205,155, entitled "Stable Transformation of Plant Cells," pp. 1–29 (Filed Jun. 10, 1988).

P. J. Charest, et al., "Factors Affecting the Use of Chloramphenicol Acetyltransferase as a Marker for Brassica Genetic Transformation", *Plant Cell Reports*, 7, 628–631 (1989).

(List continued on next page.)

*Primary Examiner*—Gary Benzion
*Attorney, Agent, or Firm*—Schwegman, Lundberg, Woessner & Kluth, P.A.

[57] ABSTRACT

The present invention provides a method for conferring tolerance or resistance to water or salt stress in a monocot plant, and/or altering the osmoprotectant content of a monocot plant, by introducing a preselected DNA segment into the plant. This invention also relates to the transformed cells and seeds, and to the fertile plants grown from the transformed cells and to their pollen.

24 Claims, 11 Drawing Sheets

FOREIGN PATENT DOCUMENTS

| | | | |
|---|---|---|---|
| 0 290 395 A2 | 11/1988 | European Pat. Off. | C12N 15/00 |
| 0 292 435 A1 | 11/1988 | European Pat. Off. | C12N 15/00 |
| 0 301 749 A2 | 2/1989 | European Pat. Off. | C12N 15/00 |
| 0 353 908 A2 | 7/1989 | European Pat. Off. | C12N 15/29 |
| 0 331 855 A2 | 9/1989 | European Pat. Off. | C12M 3/00 |
| 0 334 539 A2 | 9/1989 | European Pat. Off. | C12N 15/00 |
| 0 335 528 A2 | 10/1989 | European Pat. Off. | C12N 15/00 |
| 348 348 A2 | 12/1989 | European Pat. Off. | |
| 0 385 962 A1 | 2/1990 | European Pat. Off. | C12N 15/82 |
| 0 359 617 A2 | 3/1990 | European Pat. Off. | C12N 15/53 |
| 0 360 750 A2 | 3/1990 | European Pat. Off. | C12N 15/29 |
| 0 408 403 A1 | 5/1990 | European Pat. Off. | C12N 15/32 |
| 0 424 047 A1 | 4/1991 | European Pat. Off. | C12N 15/87 |
| 0 442 174 A1 | 4/1991 | European Pat. Off. | C12N 15/82 |
| 0 459 643 A2 | 5/1991 | European Pat. Off. | C12N 15/82 |
| 0 442 175 A1 | 8/1991 | European Pat. Off. | A01H 1/02 |
| 0 452 269 A2 | 11/1991 | European Pat. Off. | C12N 15/82 |
| 469 273 A1 | 2/1992 | European Pat. Off. | |
| 0 485 970 A3 | 5/1992 | European Pat. Off. | C12N 15/82 |
| 0 589 110 A1 | 3/1994 | European Pat. Off. | A01N 63/02 |
| 2661421 | 11/1991 | France . | |
| 3738874 A1 | 11/1988 | Germany . | |
| 4013099 A1 | 10/1991 | Germany . | |
| 61-134343 | 5/1984 | Japan . | |
| 96-253871 | 4/1996 | Japan | C12N 15/10 |
| 96-512578 | 10/1996 | Japan | C12N 15/13 |
| 8801444 | 1/1990 | Netherlands . | |
| 2 159 173 | 11/1985 | United Kingdom | C12N 15/00 |
| WO 85/01856 | 5/1985 | WIPO | A01B 76/00 |
| WO 85/02972 | 7/1985 | WIPO | A01C 1/06 |
| WO 87/04181 | 7/1987 | WIPO | C12N 1/00 |
| WO 87/05629 | 9/1987 | WIPO | C12N 15/00 |
| WO 89/04371 | 5/1989 | WIPO | C12N 21/00 |
| 89/10369 | 11/1989 | WIPO | C12N 5/00 |
| WO 89/11789 | 12/1989 | WIPO | A01H 1/00 |
| WO 89/12102 | 12/1989 | WIPO | C12N 15/00 |
| WO 90/01869 | 3/1990 | WIPO | A01H 1/00 |
| WO 90/02801 | 3/1990 | WIPO | C12N 15/32 |
| WO 90/10691 | 8/1990 | WIPO | C12N 5/00 |
| WO 91/02071 | 2/1991 | WIPO | C12N 15/82 |
| WO 91/04323 | 4/1991 | WIPO | C12N 9/10 |
| WO 91/00183 | 5/1991 | WIPO . | |
| WO 91/10725 | 7/1991 | WIPO | C12N 5/00 |
| WO 91/16432 | 10/1991 | WIPO | C12N 15/31 |
| WO 92/06205 | 4/1992 | WIPO | C12N 15/82 |
| WO 92/09696 | 6/1992 | WIPO | C12N 15/82 |
| WO 92/12250 | 7/1992 | WIPO | C12N 15/82 |
| 91/17580 | 10/1992 | WIPO | C12N 05/10 |
| WO 92/19731 | 11/1992 | WIPO | C12N 15/00 |
| WO 93/07278 | 4/1993 | WIPO | C12N 15/82 |
| 93/09237 | 5/1993 | WIPO | C12N 15/82 |
| WO 93/08682 | 5/1993 | WIPO | A01H 1/00 |
| WO 93/14210 | 7/1993 | WIPO | C12N 15/82 |
| WO 93/19190 | 9/1993 | WIPO | C12N 15/82 |
| WO 93/21335 | 10/1993 | WIPO | C12N 15/87 |
| 94/14970 | 7/1994 | WIPO . | |
| 95/06128 | 3/1995 | WIPO | C12N 15/82 |
| 95/13389 | 5/1995 | WIPO | C12N 15/82 |
| 95/30005 | 11/1995 | WIPO . | |
| 96/00789 | 1/1996 | WIPO . | |
| 96/29857 | 10/1996 | WIPO . | |

OTHER PUBLICATIONS

Finnegan, J., et al., "Transgene Inactivation: Plants Fight Back!" *Bio/Technol.*, 12, 883–888 (Sep., 1994).

L. Herrera–Estrella, et al., "Use of Reporter Genes to Study Gene Expression in Plant Cells", In: *Plant Molecular Biology Manual B1*, Kluwer Academic Publishers, Dordrecht, pp. 1–22, (1988).

M. M. Johri, et al., "Genetic Approaches to Meristem Organization", In: *Maize for Biological Research*, W. F. Sheridan, (ed.), Plant Molecular Biology Association, pp. 301–310 (1982).

Bohnert, H.J., "Coping with Water Deficit–Application of Biochemical Principles," 1995 Plant Physiology Meeting, Abstract No. 20003 (1995).

Bohnert, H.J., et al., "Adaptations to Environmental Stresses," *The Plant Cell*, 7, 1099–1111 (1995).

Boyer, J.S., "Water Deficits and Photosynthesis," In: *Water Deficits and Plant Growth*, vol. IV, Kozlowski, T. T., (ed.), Academic Press, New York, pp. 153–190 (1976).

Landi, P., et al., "Genetic Analysis of Leaf ABA Concentration and of Agronomic Traits in Maize Hybrids Grown Under Different Water Regimes," *Maydica*, 40, 179–186 (1995).

Milborrow, B. V., "Abscisic Acid and Other Hormones," In: *The Physiology and Biochemistry of Drought Resistance in Plants*, Paleg, L. G., et al., (eds.), Academic Press, New York, pp. 347–388 (1981).

Tarczynski, M. C., et al., "Stress Protection of Transgenic Tobacco by Production of the Osmolyte Mannitol." *Science*, 259, 508–510 (1993).

Tarczynski, M. C., et al., "Expression of a Bacterial mtlD Gene in Transgenic Tobacco Leads to Production and Accumulation of Mannitol," *Proc. Natl. Acad. Sci. USA*, 89, 2600–2604 (1992).

Xue, Q., et al., "Genotypic Variation in Osmotic Adjustment Among Closely Related Wheat Lines," Agronomy Abstracts, p.78 (1995).

Holmstrom, K., et al., "Production of the *Escherichia coli* betaine–aldehyde dehydrogenase, an enzyme required for the synthesis of the osmoprotectant glycvine betaine, in transgenic plants", *The Plant Journal*, 6(5), pp. 749–758, (1994).

Kavi Kishor, P.B., et al., "Overexpression of Delta 1–Pyrroline–5–Carboxylate Sythetase Increases Proline Production and Confers Osmotolerance in Transgenic Plants", *Plant Physiol.*, 108, 1387–1394, (1995).

McCue, K.F., et al., "Drought and salt tolerance: towards understanding and application", *Tibtech*, vol. 8, pp. 358–362, (Dec. 1990).

Rathinasabapathi, B. et al., "Metabolic engineering of glycine betaine synthesis: plant betaine aldehyde dehydrogenase lacking typical transit peptides are targeted to tobacco chloroplasts where they confer betaine aldehyde resistance" *Planta*, 193, pp. 155–162 (1994).

Saneoka, H., et al., "Salt toleranacae of glycinebetaine–deficient and –containing maize lines 1", *Plant Physiol.*, 107, pp. 631–638, (1995).

Tarczynski, M.C., et al., "Stress Protection of Transgenic Tobacco by Production of the Osmolyte Mannitol", *Science*, vol. 259, pp. 508–510, (Jan. 22, 1993).

Xu, D., et al., "Expression of a late embryogenesis abundant protein gene, HVA1, from barley confers tolerance to water deficit and salt stress in transfenic rice", *Plant Physiol*, 110, pp. 249–257, (1996).

Abstracts, 35th Annual Maize Genetics Conference, *In Vitro Cellular and Devel. Biol.*, 28:(3) (1992).

"Bullets Transform Plant Cells," *Agricell Report*, 9, 5, (Jul. 1987).

"Bio–Technica Applies for Field Test of Genetically Engineered Corn," *Genetic Technology News*, 10(3), (Mar. 1990).

Catalog, *Handbook of Fine Chemicals*, Aldrich Chem. Co., p. 508 (1988).

"Chipping Away at Old Weed Enemies," Farm Science Outlook, *Prairie Farmer* 162, 34 (Feb. 20 1990).

"Corn Transformers Multiply," *Bio/Technol.*, 8, 490 (Jun. 1990).

"Cornell U. Gene Gun Hits Biotech Bullseye," *Agriculture Technology*, p. 13.

"Dalapon," Merck Index, 11th edition, S. Budavae, (ed.), Merck and Co., pp. 405–406 (1989).

"Dekalb Researchers Produce Fertile Corn Plants with Foreign Genes," *ARI Newsletter*(Oct./Nov. 1990).

Dialog Search of Japanese Patent No. 61–134343 (1986).

EPO Notice Regarding Publication of Bibliographic Data for EPO 0485506 (1992).

"Gene Guns Succeed in Altering Corn," *Biotechnology News*, p. 2 (Apr. 1990).

"Genetic Engineering Advance Announced for Corn Plants, *"Investor's Daily*, (Apr. 19, 1990).

"Genetically Engineered Corn: Breakthrough Brings Market Closer," *Genetic Technology News*, 8–11 (Oct. 1990).

"Herbicide–Resistant Corn" *CT Academy of Science and Engineering, Case Reports*, 5(4), 6 (1990).

International Search Report, PCT/US 90/04462, mailed January 15, 1991.

International Search Report, PCT/US 90/09699, mailed August 16, 1995.

International Society for Plant Molecular Biology, Program and Abstracts, Molecular Biology of Plant Growth and Development, Tuson, Arizona, Oct. 6–11 (1991).

"Keystone Crops," *Agricultural Genetics Report*, (Mar./Apr. 1990).

Patent Family Record for Australian Patent 87 80 893.

"Plant Science Research, Inc. Achieves Successful Transformation of Corn," *Genetic Engineering News*, 10(3), 3 (Mar. 1990).

"Shotgunning DNA into Cells," *Genetic Engineering News*, (Jul./Aug. 1987).

"Sticky Ends," Genetic Engineering News, 10(5), 1 (May 1990).

"Teams from USDA/Monsanto and DeKalb Genetically Engineer Corn," *Genetic Technology News*, 10(5) (May 1990).

"Two Teams Succeed in Putting Foreign Genes in Corn Plants," *Genetic Engineering Letter*, 10(8), 3 (Apr. 24, 1990).

"USDA Approves More Field Tests," *Genetic Technology News*, 11(7), 12 (Jul. 1991).

"USDA Approves Field Test for BioTechnica's Genetically Engineered Corn," *Genetic Technology News*, 10(7), 6 (Jul. 1990).

Adang, M. J., et al., "Characterized Full–Length and Truncated Plasmid Clones of the Crystal Protein of *Bacillus thuringiensis* subsp. *kurstaki* HD–73 and Their Toxicity to *Manduca sexta*," *Gene*, 36, 289–300 (1985).

Ahokas, H. "Transfection of Germinating Barley Seed Electrophoretically with Exogenous DNA," *Theor. Appl. Genet.*, 77, 469–472 (1989).

Ahokes, H. "Electrophoretic transfection of cereal grains with exogenous nucleic acid," Soc. Biochem. Biophys. Microbio. Fen., Biotieteen Paivat ( Bioscience Days), Abstract, Technical University of Helsinki, Espoo, p. 2 (1989).

Akella, V., et al., "Expression in Cowpea Seedings of Chimeric Transgenes after Electroporation into Seed–Derived Embryos," *Plant Cell Rep.*, 12, 110–117 (1993).

Altenbach, S. B., et al., "Enhancement of the Methionine Content of Seed Proteins by the Expression of a Chimeric Gene Encoding a Methionine–Rich Protein in Transgenic Plants," *Plant. Mol. Biol.*, 13, 513–522 (1989).

Altenbach, S. B., et al., "Cloning and Sequence Analysis of a cDNA Encoding a Brazil Nut Protein Exceptionally Rich in Methionine," *Plant Mol. Biol.*, 8, 239–250 (1987).

Ampe, C., et al., "The Amino–Acid Sequence of the 2S Sulphur–Rich from Seed of Brazil Nut (*Bertholletia excelsa* H. B. K.)," *Eur. J. Biochem.*, 159, 597–604 (1986).

Armstrong, C. L., et al., "Establishment and Maintenance of Friable, Embryogenic Maize Callus and the Involvement of L–Proline," *Planta*, 164, 207–214 (1985).

Armstrong, C. L., et al., "Genetic and cytogenetic variation in plants regenerated from organogenic and friable, embryonic tissue cultures of maize," *Biological Abstracts*, vol. 85, Abstract No. 117662 (1988).

Aves, K., et al., Transformation of an Elite Maize Inbred Through Microprojectile Bombardment of Regenerable Embryonic Callus, *In Vitro Cell. Develop. Biol.*, 28A, p. 124A, Abstract No. P–1134 (1992).

Bao–Jian, L., et al., "Introduction of Foreign Genes into the Seed Embryo Cells of Rice by Electroinjection and the Regeneration of Transgenic Rice Plants," *Science in China*, 34, 925–931 (1991).

Barker, R. F., et al., "Nucleotide Sequence of the T–DNA Region from the *Agrobacterium tumefaciens* Octopone Ti Plasmid pTi15955," *Plant Mol. Biol.*, 2, 335–350 (1983).

Beerman, F., et al., "Tyrosinase as a Marker for Transgenic Mice," *Nuc. Acids. Res.*, 19, 958 (1991).

Belanger, F. C., et al., "Molecular Basis for Allelic Polymorphism of the Maize Globulin–1 Gene " *Genetics*, 129, 863–872 (1991).

Benner, M. S., et al., "Genetic Analysis of Methionine–Rich Storage Protein Accumulation in Maize," *Theor. Appl. Genet.*, 78, 761–767 (1989).

Bevan, M., et al., "A Chimaeric Antibiotic Resistance Gene as a Selectable Marker for Plant Cell Transformation," *Nature*, 304, 184–187 (1983).

Bevan, M., et al., "Structure and Transcription of the Nopaline Synthase Gene Region of T–DNA," *Nuc. Acids. Res.*, 11, 369–385 (1983).

Binns, A N., "Agrobacterium–mediated gene delivery and the biology of host range limitations," *Physiologia Plantarum*, 79, 135–139 (1990).

Bishop, J. E., "Two Teams Plane Genes into Corn," *The Wall Street Journal*, B1 (Apr. 1990).

Booy, G., et al., "Attempted Pollen–Mediated Transformation of Maize," *J. Plant Physiol.*, 135, 319–324 (1989).

Boulton, M. I., et al., "Specificity of Agrobacterium–mediated delivery of maize streak virus DNA to members of the Gramineae," *Plant Molecular Biology*, 12, 31–40 (1989).

Brill, W. J., "Agriculture Microbiology," *Scientific American*, 245(3), 199–215 (Sep. 1981).

Brunke, K.J., et al., "Insect Control with Genetically Engineered Crops," *Trends in Biotechnol.*, 9, 197–200 (1991).

Buchanan–Wollaston, V., et al., "Detoxification of the Herbicide Dalapon by Transformed Plants," *J. of Cell. Biochem.*, 13D, p. 330, Abstract No. M503 (1989).

Caliguri, M. G., et al., "Identification of Amino Acid Residues Involved in Feedback Regulation of the Anthranilate Synthase Complex from *Salmonella typhimurium*," *J. Biol. Chem.*, 266, 8328–8335 (1991).

Callis, J., et al., "Introns Increase Gene Expression in Cultures Maize Cells," *Genes and Development*, 1, 1183–1200 (1987).

Cao, J., et al., "Transformation of Rice and Maize Using the Biolistic Process," In:*Plant Gene Transfer*, Alan R. Liss, Inc., pp. 21–33 (1990).

Carpita, N. C., "The Biochemistry of Growing Cell Walls," In: *Physiology of Cell Expansion During Plant Growth*, Cosgrove, D. J., et al., (eds.) Am. Soc. Plant Physiol., pp. 28–100 (1987).

Chan, M.-T., et al., "Agrobacterium–Mediated Production of Transgenic Rice Plants Expressing a Chimeric α-Amylase Promoter/β-Glucuronidase Gene," *Plant Mol. Biol.*, 22, 491–506 (1993).

Chandler, V. L., et al., "Two Regulatory Genes of the Maize Anthocyanin Pathway are Homologous: Isolation of B Utilizing R Genomic Sequences," *The Plant Cell*, 1, 1175–7783 (1989).

Chasan, R., "Transforming Maize Transformation," *The Plant Cell*, 4, 1463–1464 (1992).

Chourey, P. S., et al., "Callus Formation from Protoplasts of a Maize Cell Culture," *Theor. Appl. Genet.*, 59, 341–344 (1981).

Christou, P., et al., "Opine Synthesis in Wild-Type Plant Tissue," *Plant Physiol.*, 82, 218–221 (1986).

Christou, P., et al., "Soybean Genetic Engineering–Commercial Production of Transgenic Plants," *Trends Biotechnol.*, 8, 145–151 (1990).

Christou, P., et al., "Cotransformation Frequencies of Foreign Genes in Soybean Cell Cultures," *Theor. Appl. Genet.*, 79, 337–341 (1990).

Christou, P., et al., "Genetic Transformation of Crop Plants Using Microprojectile Bombardment," *The Plant Journal*, 2, 275–281 (1992).

Christou, P., et al., "Stable Transformation of Soybean Callus by DNA–Coated Gold Particles," *Plant Physiol.*, 87, 671–674 (1988).

Chu, C.-C., et al., "Establishment of an Efficient Medium for Anther Culture of Rice Through Comparative Experiments on the Nitrogen Sources," *Sci. Sin. (Peking)*, 13, 659–668 (1975).

Clark, B., "Biotech Advance in Corn: Gunslinging Researchers Fire Marker Genes in to Corn," *AG Consultant*, 46(7), 12 (Jul. 1990).

Cocking, F., et al., "Gene Transfer in Cereals," *Science*, 236, 1259–1262 (1987).

Coe et al., "The Genetics of Corn" In: *Corn and Corn Improvement*, 2nd edition, Sprague, G. F., (ed.), American Soc. Agronomy, Inc, Madison, WI, p. 138 (1977).

Comai, L., et al., "Expression in Plants of a Mutant aroA Gene from *Salmonella typhimurium* Confers Tolerance to Glyphosate," *Nature*, 317, 741–744 (Oct., 1985).

Creissen, G., et al., "Agrobacterium –and Microprojectile–Mediated Viral DNA Delivery into Barley Microspore Derived–Cultures," *Plant Cell Rep.*, 8, 680–683 (Apr. 1990).

Crossway, A., et al., "Integration of foreign DNA following microinjection of tobacco mesophyll protoplasts," *Mol. Gen. Genet.*, 202, 179–185 (1986).

D'Halluin, K., et al., "Transgenic Maize Plants by Tissue Electroporation," *The Plant Cell*, 4, 1495–1505 (1992).

Darvill, A., et al., "The Primary Cell Walls of Flowering Plants," In: *The Biochemistry of Plants*, vol. 1, pp. 91–162 (1980).

Dauce-LeReverand, B., et al., "Improvement of *Escherichia coli* Strains Overproducing Lysine Using Recombinant DNA Techniques," *Eur. J. Appl. Microbiol. Biotechnol.*, 15, 227–231 (1982).

De Block, M., et al., "Engineering herbicide resistance on plants by expression of a detoxifying enzyme," *EMBO J.*, 6, 2513–2518 (1987).

De Greef, W., et al., "Evaluation of herbicide resistance in transgenic crops under field conditions," *Bio/Technol.*, 7, 61–64 (1989).

Dekeyser, R. A., et al., "Evaluation of Selectable Markers for Rice Transformation," *Plant Physiol.*, 90, 217–223 (1989).

Dekeyser, R. A., et al., "Transient Gene Expression in Intact and Organized Rice Tissues," *The Plant Cell*, 2, 591–602 (1990).

DeWald et al., "Plant regeneration from inbred maize suspensions," VIIth International Congress on Plant Tissue and Cell Culture, p. 12, Abstract No. A1–36 (Jun. 24–29, 1990).

DeWet, J. M. J., et al., "Exogenous gene transfer in maize (*Zea mays*) using DNA–treated pollen;" In: *The experimental manipulation of ovule tissues*. Chapman, G. P., et al., (eds.), Longman, New York, pp. 197–209 (1985).

DeWet, J. R. et al., "Cloning of Firefly Luciferase cDNA and the Expression of Active Luciferase in *Escherichia coli*, " *Proc. Nat. Acad. Sci. USA*, 82, 7870–7873 (1985).

Donn, G., et al., "Stable Transformation of Maize with a Chimaeric, Modified Phosphinothricin–Acetyltransferase Gene from *Streptomyces viridochromogens*, " Abstracts, VIIth International Congress Plant Tissue Cell Culture, p. 53, Abstract No. A2–38 (Jun. 24–29, 1990).

Dupuis, I., et al., "Gene Transfer to Maize Male Reproductive Structure by Particle Bombardment of Tassel Primordia," *Plant Cell Rep.*, 12, 607 (1993).

Ellis, J. G., et al., "Does the OCS–Element Occur as a Functional Component of the Promotors of Plant Genes?" *EMBO J.*, 3203–3208 (1987).

Evans, D. A., et al., "Somaclonal Variation–Genetic Basis and Breeding Applications," *Trends Genet.*, 5, 46–50 (1989).

Fennel, A., et al., "Electroporation and PEG Delivery of DNA into Maize Microspores," *Plant Cell Reports*, 11, 567–570 (1992).

Fitzpatrick, T., "Pleiotrophic Gene Found in Barley Plant," *Genetic Engineering News*, 13, 1 (1993).

Fransz, P., et al., "Cytodifferentiation during callus initiation and somatic embryogenesis in *Zea mays* L.," Ph.D. thesis, U. of Wageningen Press, The Netherlands (1988).

Freeling, J.C., et al., "Development Potentials of Maize Tissue Cultures," *Maydica*, XXI, 97–112 (Jul. 1977).

Freiberg, "More Researchers Discover Corn Transformation Technology," *AG Biotechnology News*, p. 26 (1990).

Fromm, M. E., et al., "Inheritance and Expression of Chimeric Genes in the Progeny of Transgenic Maize Plants," *Bio/Technol.*, 8, 833–839 (1990).

Fromm, M. E., et al., "Stable Transformation of Maize after Gene Transfer by Electroporation," *Nature*, 319, 791–793 (1986).

Fromm, M., et al., "Expression of Genes Transfected into Monocot and Dicot Plant Cells by Electroporation," *Proc. Nat. Acad. Sci. USA*, 82, 5824–5828 (1985).

Fry, S.C., "Introduction to the Growing Cell Wall," In: *The Growing Plant Cell Wall: Chemical and Metabolic Analysis*, Longman Scientific and Technical, New York, pp. 1–5, 102–109 (1988).

Geiser, M., et al., "The Hypervariable Region on the Genes Coding for Entomopathogenic Crystal Proteins of *Bacillus thuringiensis*: Nucleotide Sequence fo the kurhd1 gene of subsp. kurstaki HD1," *Gene*, 48, 109–118 (1986).

Goff, S. A., et al., "Plant Regeneration of Anthocyanin Biosynthetic Genes Following Transfer of B Regulatory Genes into Maize Tissues," *EMBO J.*, 9, 2517–2522 (1990).

Gordon-Kamm, W. J., et al., "Stable Transformation of Embryonic Maize Cultures by Microprojectile Bombardment," *J. Cellular Biochem.*, 13D, p. 259, Abstract No. M122 (1989).

Gordon-Kamm, W. J., et al., "Transformation of Maize Cells and Regeneration of Fertile Transgenic Plants," *The Plant Cell*, 2, 603–618 (1990).

Gould, J., et al., "Transformation of the Graminae by *Agrobacterium tumefaciens*," Int. Soc. Plant Mol. Biol. 3rd Int. Congress, Abstract No. 1277 (1991).

Gould, O., et al., "Shoot Tip Culture as a Potential Transformation System," Abstracts, Beltwide cotton production research conferences, New Orleans, LA, p. 91 (1988).

Gould, J., et al., "Transformation of Zea mays L. Using *Agrobacterium tumefaciens* and the Shoot Apex," *Plant Physiol.*, 95, 426–434 (1991).

Graves, A., et al., "The transformation of Zea mays seedlings with *Agrobacterium tumefacians*," *Plant Mol. Biol.*, 7, 43–50 (1986).

Green, C., et al., "Plant Regeneration from Tissue Cultures of Maize," *Crop. Sci.*, 15, 417–421 (1975).

Green, C., et al., "Plant Regeneration in Tissue Cultures of Maize," In: *Maize for Biological Research*, Sheridan, W. F., (ed.) Plant Mol. Biol. Assoc., pp. 267–372 (1982).

Green, C., et al., "Somatic Cell Genetic Systems in Corn," In: *Advances in Gene Technoogy: Molecular Genetics of Plant and Animals*, Academic Press, Inc., pp. 147–157 (1983).

Grimsley, N., et al., "DNA Transfer from Agrobacterium to Zea mays or Brassica by Agroingection is Dependent on Bacterial Virulence Functions," *Mol. Gen. Genet.*, 217, 309–316 (1989).

Gritz, L., et al., "Plasmid–Encoded Hygromycin B Resistance: The Sequence of Hygromycin B Phosphotransferase Gene and Its Expression in *Escherichia coli* and *Saccharomyces cerevisiae*," *Gene*, 25, 179–188 (1983).

Guerineau, F., et al., "Sulfonamide Resistance Gene for Plant Transformation," *Plant Molecular Biology*, 15, 127–136 (1990).

Guilley, H., et al., "Transcriptional of Cauliflower Mosaic Virus DNA: Detection of Promoter Sequences, and Characterization of Transcript," *Cell*, 30, 763–773 (Oct., 1982).

Gunset, G., "Genetic Advance May Transform Corn," *Chicago Tribune* (Apr. 19, 1990).

Gunset, G., "Corn Farmers See Economic, Environmental Gold in Designer Genes," *Chicago Tribune* (Jan. 21, 1991).

Hallauer A. R., et al., "Corn Breeding," In: *Corn and Corn Improvement*, 3rd edition, Sprague, G. F., et al., (eds.), Agronomy Soc. Amer., pp. 463–564 (1988).

Haughn, G. W., "Transformation with a Mutant *Arabidopsis* Acetolactate Synthase Gene Render Tobacco Resistant to Sulfonylurea Herbicides," *Mol. Gen. Genet.*, 211, 266–271 (1988).

Hautpman, R. M., et al., "Evaluation of Selectable Markers for Obtaining Stable Transformants on the Gramineae," *Plant Physiol.*, 86, 602–606 (1988).

Hiel, Y., et al., "Efficient Transformation of Rice (Oryza Sativa L.) Mediated by Agrobacterium and Sequence Analysis of the Boundaries of the T–DNA," *The Plant J.*, 6, 271–282 (1994).

Hoffman, L. M., et al., "a Modified Storage Protein in Synthesized, Processed, and Degraded in the Seeds of Transgenic Plants," *Plant Mol. Biol.*, 11, 717–729 (1988).

Hoffman, L. M., et al., "Synthesis and Protein Body Deposition of Maize 15kD Zein in Transgenic Tobacco Seeds," *EMBO J.*, 6, 3213–3221 (1987).

Hofte, H., et al., "Insecticidal Crystal Proteins of *Bacillus thuringiensis*," *Microbiol. Rev.*, 53, 242–255 (1989).

Hong, B., et al., "Developmental and Organ–Specific Expression of an ABA–and Stress–Induced Protein in Barley," *Plant Mol. Biol.*, 18, 663–674 (1992).

Hooykaas, P.J.J., "Transformation of plant cell via Agrobacterium," *Plant Mol. Biol.*, 13, 327–336 (1989).

Horn, M., et al., "Transgenic Plants of Orchard Grass (*Dactylis glomerata* L.) from Protoplasts," *Chem. Abstracts*, 110, p. 208, Abstract No. 89869a (1989).

Horn, M., et al., "Transgenic Plants of Orchardgrass (*Dactylis glomerata* L.) from Protoplasts," *Plant Cell Reports*, 7, 469 (1988).

Howe, A., et al., "Development of Glyphosphate as a Selectable Marker for the Production of Fertile Transgenic Corn Plants," *In Vitro Cell. Develop. Biol.*, 28A, p. 124A, Abstract No. P–1136 (Jul.–Aug. 1992).

Huang, Y., et al., "Factors Influencing Stable Transformation of Maize Protoplasts by Electroporation," *Plant Cell, Tissue and Organ Cultures*, 18, 281 (1989).

Imbrie-Milligan, C., et al., "Microcallus Growth from Maize Protoplasts," *Planta*, 171, 58–64 (1987).

Jahne, A., et al., "Regeneration of Fertile Plants from Protoplasts Derived from Embryogenic Cell Suspension of Barley (*Hordeum vulgare* L.)," *Plant Cell Rep.*, 10, 1–6 (1991).

Jayne, S., et al., "Analysis of Elite Transgenic Maize Plants Produced by Microprojectile Bombardment," Program and Abstracts, Int. Soc. for Plant Mol. Biol., 3rd Int. Cong., Abstract No. 338 (Oct. 6–11, 1991).

Jefferson, R., et al., "β–Glucuronidase from *Escherichia coli* as a Gene–Fusion Marker," *Proc. Nat. Acad. Sci. USA*, 83, 8447–8451 (1986).

Jefferson, R., et al., "GUS Fusions: β–Glucuronidase as a Sensitive and Versatile Gene Fusion Marker in Higher Plants," *EMBO J.*, 6, 3901–3907 (1987).

Jefferson, R., "Assaying chimeric genes in plants: the GUS gene fusion system," *Plant Mol. Biol. Rep.*, 5, 387–405 (1987).

Jones, H., et al., "Recent Advances in Plant Electroporation," *Oxford Surveys of Plant Molecular and Cell Biol.*, 4, 347–357 (1987).

Jones, H., et al., "Transient Gene Expression in Electroporated Solanum Protoplasts," *Plant Mol. Biol.*, 13, 503–511 (1989).

Kaeppler, H. F., et al., "Silicon Carbide Fiber–Mediated DNA Delivery into Plant Cells," *Plant Cell Rep.*, 9, 415–418 (1990).

Kamo, K., et al., "Establishment and Characterization of Long–Term Embryonic Maize Callus and Cell Suspension Cultures," *Plant Sci.*, 45, 111–117 (1986).

Kamo, K. et al., "Regeneration of *Zea mays* L. from Embryogenic Callus," *Bot. Gaz.*, 146, 327–334 (1985).

Kao, K. N., et al., "Nutritional Requirements for Growth of *Vicia hajastana* Cells and Protoplasts at a Very Low Population Density in Liquid Media," *Planta*, 126, 105–110 (1978).

Kartha, K., et al., "Transient Expression of Chloramphenicol Acetyl Transferase (CAT) Gene in Barley Cell Cultures and Immature Embryos Through Microprojectile Bombardment," *Plant Cell Rep.*, 8, 429–432 (1989).

Kay, R., et al., "Duplication of CaMV 35S Promoter Sequences Creates a Strong Enhancer for Plant Genes," *Science*, 236, 1299–1302 (Jun. 5, 1987).

Kirihara, J., et al., "Differential Expression of a Gene for a Methionine-Rich Storage Protein in Maize," *Mol. Gen. Genet.*, 211, 477–484 (1988).

Kirihara, J., et al., "Isolation and Sequence of a Gene Encoding a Methionine–Rich 10–kD Zein Protein from Maize," *Gene*, 71, 359–370 (1988).

Klein, T., et al., "Transfer of Foreign Genes into Intact Maize Cells with High–Velocity Microprojectiles," *Proc. Nat. Acad.Sci. USA*, 85, 4305–4309 (1988).

Klein, T. M., et al., "Factors Influencing Gene Delivery into Zea mays Cells by High Velocity Microprojectiles," *Bio/Technol.*, 6, 559–563 (1988).

Klein, T. M., et al., "High–Velocity Microprojectiles for Delivering Nucleic Acids to Living Cells," *Nature*, 327, 70–73 (1987).

Klein, T., et al., "Genetic Transformation of Maize Cell by Particle Bombardment and the Influence of Methylation on Foreign Gene Expression," In: *Gene Manipulation in Plant Improvement II*, Gustafson, J. P., (ed.), Plenum, Press, NY, pp. 265–266 (1990).

Klein, T., et al., "Genetic transformation of Maize Cells by Particle Bombardment," *Plant Physiol.*, 91, 440–444 (1989).

Klein, T., et al., "Regulation of Anthocyanin Biosynthetic Genes Introduced into Intact Maize Tissue by Microprojectiles," *Proc. Nat. Acad. Sci. USA*, 86, 6682–6685 (1989).

Kozak, M., "Compilation and Analysis of Sequence from the Translational Start Site in Eukaryotic mRNAs," *Nuc. Acids. Res.*, 12, 857–871 (1984).

Kozak, M., "Point Mutations Define a Sequence Flanking the AUG Initiator Codon that Modulates Translation by Eukaryotic Ribosomes," *Cell*, 44, 283–292 (1986).

Koziel, M. G., et al., "Field Performance of Elite Transgenic Maize Plants Expressing and Insecticidal Protein Derived from *Bacillus thuringenesis*," *Bio/Technol.*, 11, 194–200 (1993).

Kreitlow, B., "Genetic Engineering 'Breakthrough' Disputed," Cedar Rapids Gazette (Apr. 20, 1990).

Kriz, A. L., et al., "Characterization of the Maize Globulin–2 Gene and Analysis of Two Null Alleles," *Biochemical Genetics*, 29, 241–254 (1991).

Kuhlemeir, C., et al., "Regulation of Gene Expression in Higher Plants," *Ann. Rev. Plant Physiol.*, 38, 234–239 (1987).

Langridge, et al., "Transformation of Cereals via Agrobacterium and the Pollen Pathway: A Critical Assessment," *The Plant J.*, 2, 613–638 (1992).

Laursen, C. M., et al., "Production of Fertile Transgenic Maize by Electorporation of Suspension Culture Cells," *Plant Mol. Biol.*, 24, 51–61 (1994).

Lazzeri, P., et al., "In Vitro Genetic Manipulation of Cereals and Grasses," *Ad. Cell Culture*, 6, 291–293 (1988).

Lee, J. S., et al., "Gene Transfer into Intact Cells of Tobacco by Electroporation," *Korean J. Genet.*, 11, 65–72 (1989).

Leemans, J., "Genetic Engineering for Fertility Control," Keystone Symposium on Crop Improvement via Biotechnology: An International Perspective, Abstract No. Y016 (Apr. 10–26, 1992).

Levitt, J., "Growth Regulators"In: *Introduction to Plant Physiology*, The C.V. Mosby Company, St. Louis , p. 241 (1969).

Li, X.–Q., et al., "GUS Expression in Rice Tissues Using Agrobacterium–Mediated Transformation," Program and Abstract, Int. Soc. for Plant Mol. Biol., 3rd Int. Cong., Abstract No. 385 (Oct. 6–11, 1991).

Lindsey, K., et al., "Electroporation of Cells," *Physiologia Plantarum*, 79, 168–172 (1990).

Lindsey, K., et al., "The Permeability of Electroporated Cells and Protoplasts of Sugar Beets," *Planta*, 172, 346–355 (1987).

Masumura, T., et al., "cDNA Cloning of an mRNA Encoding a Sulfar–Rich 10 kDa Prolamin Polypeptide in Rice Seeds," *Plant Mol.Biol.*, 12, 123–130 (1989).

McCabe et al., "Stable Transformation of Soybean (*Glycine max*) by Particle Acceleration," *Bio/Technol.*, 6, 923–926 (1988).

McDaniel, C., et al., "Cell–Lineage Patterns in the Shoot Apical Meristem of the Germinating Maize Embryo," *Planta*, 175, 13–22 (1988).

Meadows, M., "Characterization of Cells and Protoplasts of the B73 Maize Cell Line," *Plant Sci. Lett.*, 28, 337–348 (1982/83).

Mendel, R., et al., "Delivery of Foreign Genes to Intact Barley Cell by High–Velocity Microprojectiles," *Theor. Appl. Genet.*, 78, 31–34 (1989).

Messing, J., "Corn Storage Protein: A Molecular Genetic Model," Division of Energy BioSciences–Summaries of FY 1990 Activities, p. 70, Abstract No. 135 (1990).

Moffat, A. S., "Corn Transformed," *Science*, 249, 630 (Aug. 10, 1990).

Morikawa, et al., "Gene Transfer into Intact Plant Cells by Electroporation Through Cell Walls and Membranes," *Gene*, 41, 121(1986).

Morocz, S. et al., "An Improved System to Obtain Fertile Regenerants via Maize Protoplasts Isolated From a Highly Embryonic Suspension Culture," *Theor. Appl. Genet.*, 80, 721–726 (1990).

Morocz, S., et al., "Two Approaches to Rendering Zea mays L. Applicable to Tissue Culture Manipulations," Abstracts, VIIth Int. Cong. on Plant Tissue and Cell Culture, Amsterdam A1–102, Abstract No. 209, p. 190 (1990).

Murakami, T., et al., "The Bialaphos Biosynthetic Genes of *Streptomyces hygroscopicus*: Molecular Cloning and Characterization of the Gene Cluster," *Mol. Gen. Genet.*, 205, 42–50 (1986).

Murashige, T., et al., A Revised Medium for Rapid Growth and Bio Assays with Tobacco Tissue Cultures, *Physiol. Plant.*, 15, 473–497 (1962).

Murphy, H. L., "New Dekalb–Pfizer Seed Chief to Harvest R & d Breakthroughs," *Crain's Business Weekly*, pp. 38–39 (1990).

Murray, E. E., et al., "Codon usage in plant genes," *Nuc. Acids. Res.*, 17, 477–498 (1989).

Murry, L. E., et al., "Transgenic Corn Plants Expressing MDMV Strain B Coat Protein are Resistant to Mixed Infections of Maize Dwarf Mosaic Virus and Maize Chlorotic Mottle Virus," *Bio/Technol.*, 11, 1559–1564 (1993).

Nelson, R. S., "Virus Tolerance, Plant Growth, and Field Performance of Transgenic Tomato Plants Expressing Coat Protein from Tobacco Mosaic Virus," et al., *Bio/Technol.*, 6, 403–409 (1988).

Nelson, T., "New Horses for Monocot Gene Jockeys," *The Plant Cell*, 2, 589 (1990).

Neuffer, "Growing Maize for Genetic Purpose," Maize for Biological Research, Plant Mol. Biol. Assoc., (1988).

Niyogi, K. K., et al., "Suppressors of trp1 Fluoresence Identify a New Arabidopsis Gene, TRP4, Encoding the Anthranilate Synthase beta Gene," *The Plant Cell*, 5, 1011–1027 (1993).

Niyogi, K. K., et al., "Two Anathranilate Synthase Genes in Arabidopis: Defense–Related Regulation of the Tryptophan Pathway," *The Plant Cell*, 4, 721–733 (1992).

Odell, J., et al., "Identification of DNA Sequences Required for Activity of the Cauliflower Mosaic Virus 35S Promoter," *Nature*, 313, 810–811 (1985).

Office Action dated May 30, 1989, Goldman et al., USSN 06/880,271, filed Jun. 30, 1986.

Office Action dated March 8, 1990, Goldman, USSN 06/880,271, filed Jun. 30, 1986.

Ohta, Y., "High–Efficiency Genetic Transformation of Maize by a Mixture of Pollen and Exogenous DNA," *Proc. Nat. Acad. Sci. USA*, 83, 715–719 (1986).

Okta, Y., et al., "Gene Manifestation of Exogenous DNA Applied to Self–Propagating Stigma (Gene Action Revealed in the $M_1$ and $M_2$ Generations from Self–Pollination Applying Exogenous DNA)," *Jap. J. Breed.*, 30, 184–185 (1980).

Omirullen, S., et al., "Activity of a Chimeric Promoter with the Doubled CaMV 35S Enhancer in Protoplast–Derived Cells and Transgenic Plants in Maize," *Plant Mol. Biol.*, 21, 415–428 (1993).

Ozias–Akins, P., et al., "In vitro regeneration and genetic manipulation of grasses," *Physiol. Plant.*, 73, 565–569 (1988).

Ozias–Akins, P., et al., "Progress and Limitations in the Culture of Cereal Protoplasts," *Trends in Biotechnol.*, 2, 119–123 (1984).

Park, S. H., et al., "Selection of Maize Transformants form Shoot Apex Cultures Cocultivated with Agrobacterium Containing the Bar Gene," *In Vitro Cell. Develop. Biol.*, 29A, p. 85A, Abstract No. P–1102 (1993).

Parker, W. B., et al., "Selection and Characterization of Sethoxydim–Tolerant Maize Tissue Cultures," *Plant Physiol.*, 92, 1220–1225 (1990).

Pederson, K., et al., "Sequence Analysis and Characterization of a Maize Gene Encoding a High–Sulfur Zein Protein of $M_r$ 15,000," *J. Biol. Chem.*, 261, 6279–6284 (1986).

Perl, A., et al., "Bacterial Dihydrodipicolinate Synthase and Desensitized Aspartate Kinase: Two Novel Selectable Markers for Plant Transformation," *Bio/Technol.*, 11, 715–718 (1993).

Perlack, F.J., et al., "Modification of the Coding Sequence Enhances Plant Expression of Insect Control Protein Genes," *Proc. Nat. Acad. Sci. USA*, 88, 3324–3328 (1991).

Phillips, R. L., et al., "Elevated Protein–Bound Methionine in Seeds of a Maize Line Resistant to Lysine Plus Threonine," *Cereal Chem.*, 62, 213–218 (1985).

Phillips, R. L., et al., "Cell/Tissue Culture and In Vitro Manipulation," In: *Corn and Corn Improvement*, 3rd edition, Sprague, G. F., et al., (eds.), Agronomy Soc. Amer., pp. 345–387 (1988).

Pioneer HiBred International, Inc., *Application Under 7 CFR 340*, Release of Genetically Engineered Corn Plants, Permit No. 92–174–02, NO CBI, p. 8 (Nov. 3, 1992).

Pioneer HiBred International, Inc., *Application Under 7 CFR 340*, Release of Genetically Engineered Corn Plants, Permit No. 92–330–01, CBI–DELETED, p. 13 (Apr. 13, 1993). Phillips, R. L., et al., "Elevated Protein–Bound Methionine in Seeds of a Maize Line Resistant to Lysine Plus Threonine," *Cereal Chem.*, 62, 213–218 (1985). Pioneer's Application for Release in the *Environment Under 7 CFR 340*, Corn Plants Genetically Engineered to Express Wheat Germ Agglutinin (WGA) Genes, in Order to Confer Resistance to the European Corn Borer (*Ostrinia nubilalis*) and Tolerance to Glufosinate Herbicides, 92–022–03, NO CBI COPY, p. 11 (May 4, 1992).

Poehlman, J. "Breeding Corn (Maize)," In: *Breeding Field Crops*, 3rd edition, AVI Publishing Co., Westport CN, pp. 452 (1986).

Poehlman, J. "Breeding Corn (Maize)," In: *Breeding Field Crops*, 3rd edition, AVI Publishing Co., Westport CN, pp. 469–471, 477–481 (1986).

Potrykus, I., et al., "Callus Formation from Cell Culture Protoplasts of Corn (*Zea mays L.*)," *Theor. Appl. Genet.*, 54, 209–214 (1979).

Potrykus, I., "Gene Transfer to Cereals: An Assessment," *Bio/Technol.*, 8, 535–542 (Jun. 1990).

Potrykus, I., "Gene Transfer to Cereals: An Assessment," *Trends Biotechnol.*, 7, 269–273 (Oct. 1989).

Potrykus, I., "Gene Transfer to Plants: Assessment and Perspectives," *Physiol. Plant.*, 79, 125–134 (1990).

Potrykus, I., et al., "Callus formation from stem protoplasts of corn (*Zea mays L.*)" *Mol. Gen. Genet.*, 156, 347–350 (1977).

Potter, et al., "Enhancer–Dependent Expression of Human κImmunoglobulin Genes Introduced into Mouse Pre–B Lymphocytes by Electroporation," *Proc. Nat. Acad. Sci. USA*, 81, 7161 (1984).

Prioli, L. M., et al., "Plant Regeneration and Recovery of Fertile Plants from Protoplasts of Maize (*Zea mays L.*)," *Bio/Technol.* 7, 589–594 (Jun. 1989).

Puite, K. J., et al., "Electrofusion, a Simple and Reproducible Technique in Somatic Hybridization of *Nicotiana plumbaginifolia* mutants," *Plant Cell Rep.*, 4, 274–276 (1985).

Rasmusen, J. L., et al., "Biolistic Transformation of Tobacco and Maize Suspension Cells Using Bacterial Cells as Microprojectiles," *Plant Cell Rep.*, 13, 212–217 (1994).

Rhodes, C. A., et al., "Genetically Transformed Maize Plants from Protoplasts," *Science*, 240, 204–207 (Apr. 8, 1988).

Rhodes, C. A., et al., "Plant Regeneration from Protoplasts Isolated from Embryogenic Maize Cell Cultures," *Bio/Technol.*, 6, 56–60 (Jan. 1988).

Rhodes, C. A., "Corn: From Protoplasts to Fertile Plants," *Bio/Technol.*, 7, 548 (Jun., 1989).

Richaud, F., et al., "Chromosomal Location and Nucleotide Sequence of the *Escherichia coli* dapA Gene," *Biol. Abstracts*, 82, p. AB–391, Abstract No. 3396 (1986).

Richaud, F., et al., "Chromosomal Location and Nucleotide Sequence of the *Escherichia coli* dapA Gene," *J. Bacteriol.*, 166, 297–300 (1986).

Robbins–Roth et al., "They Make it Happen in Biotech," *Bioworld*, pp. 30–36 (Nov./Dec. 1990).

Robertson, D. S., "Loss of Mu Mutator Activity when Active Mu Systems are Transferred to Inbred Lines," *Maize Genetics Coop. Newsletter*, 60, 10 (1986).

Ross, M.C., et al., "Transient and Stable Transgenic Cells and Calli of Tobacco and Maize Following Microprojectile Bombardment," *J. Cell. Biochem.*, 13D, p. 268, Abstract No. M149 (1989).

Sahi, S. V., et al., "Metabolites in Maize Which Affect Virulence Induction in *Agrobacterium tumefaciens*," *Plant Physiol., Supplement*, p. 86, Abstract No. 514, (1989).

Sanford, J. C., "Biolistic Plant Transformation," *Physiol. Plant.*, 79, 206–209 (1990).

Sanford, J. C., "The Biolistic Process," *Trends Biotechnol.*, 6, 299–302 (1988).

Sanford, J. C., et al., "Attempted Pollen–Mediated Plant Transformation Employing Genomic Donor DNA," *Theor. Appl. Genet.*, 69, 571–574 (1985).

Sanford, J. C., et al., "Delivery of Substances into Cells and Tissues Using a Particle Bombardment Process," *Particulate Sci. Technol.*, 5, 27–37 (1987).

Sass, "Morphology: Development of the Caryopsis " In: *Corn and Corn Improvement*, 2nd edition, Sprauge, G. F., (ed.), American Soc. Agronomy, p. 89, 98 (1977).

Schmidt A., et al., "Media and environmental effects of phenolics production from tobacco cell cultures," *Chem. Abstracts*, 110, p. 514, Abstract No. 230156z (1989).

Shen, W.-H., et al., "Excision of a Transposible Element form a Viral Vector Introduced into Maize Plants by Agroinfection," *The Plant J.*, 2, 35–42 (1992).

Shen, W.-H., et al., "Amplification and expression of the β-glucuronidase gene in maize plants by vectors based on maize streak virus," *The Plant Journal*, 5, 227–236 (1994).

Shigekawa, K., et al., "Electroporation of Eukaryotes and Prokaryotes: A General Approach to the Intoduction of Macromolecules into Cells," *Bio Techniques*, 6, 742–751 (1988).

Shillito, R. D., et al., "High Efficiency Direct Gene Transfer to Plants," *Bio/Technol.*, 3, 1099 (1985).

Shillito, R. D., et al., "Regeneration of Fertile Plants From Protoplasts of Elite Inbred Maize," *Bio/Technol.*, 7, 581–587 (Jun. 1989).

Shimamoto, K., et al., "Fertile Transgenic Rice Plants Regenerated from Transformed Protoplasts," *Nature*, 338, 274–278 (1989).

Shotwell, M. A., et al., "The Biochemistry of Plants——A Comprehensive Treatise," In: *The Biochemistry of Plants*, vol. 15, Marcus, A., (ed.), Academic Press, Inc., San Diego, pp. 297–345 (1989).

Smith, R., et al., "Shoot apex explant for transformation," *Plant Physiol.*, 86, p. 108, Abstract No. 646 (1988).

Soberon, X., et al., "Construction and Characterization of New Cloning Vehicles, IV. Deletion Derivatives of pBR322 and pBR325," *Gene*, 9, 287–305 (1980).

Songstad, D. D., et al., "Transient Expression of GUS and Anthocyanin Constructs in Intact Maize Immature Embryos Following Electroporation," *Plant Cell Tissue and Organ Culture*, 33, 195–201 (1993).

Spencer, T. M., et al., "Fertile Transgenic Maize," Abstracts, 7th Annual Meeting, Mid Atlantic Plant Mol. Biol. Soc., p. 30 (1990).

Spencer et al., "Bialaphos Selection of Stable Transformation from Maize Cell Culture," *Theor. Appl. Genet.*, 79, 625–631 (May 1990).

Spencer, T. M., et al., "Segregation of Transgenes in Maize, "*Plant Mol. Biol.*, 18, 201–210 (1992).

Spencer, T.M., et al., "Selection of Stable Transformants from Maize Suspension Cultures using the Herbicides Bialaphos," Poster presentation, FASEB Plant Gene Expression Conference, Copper Mountain, Colorado (Aug. 8 1989).

Sprauge et al., "Corn Breeding," In: *Corn and Corn Improvement*, Sprauge, G. F., (ed.), American Society of Agronomy, Inc, Madison. Wi, pp. 305, 320–323 (1977).

Steimel, D., "Corn Breeders Stalk Perfect Hybrid," *Rockford Register Star*, (Aug. 6, 1990).

Steimel, D., "New Gun Will Custom–Design Corn: Breeding Technique Expected by End of '90's Will Let Crop Grow Without Pesticides or Much Water," (Apr. 1990).

Sugiyama, M., et al., "Use of the Tyrosine Gene from *Streptomyces* to Probe Promoter Sequences for *Escherichia coli*," *Plasmid*, 23, 237–241 (1990).

Suttie, J., et al., "Use of Different Selection Agents to Produce Maize Transformants of an Elite Geneotype Using Microprojectile Bombardment," Program and Abstracts, Int. Soc. Plant Mol. Biol., 3rd Int. Cong. Abstract No. 426 (Oct. 6–11, 1991).

Thompson, C., et al., "Characterization of the Herbicide–Resistance Gene bar from *Streptomyces hygroscopicus*," *EMBO J.*, 6, 2519–2523 (1987).

Tomes, D. "Status of Corn Transformation," 26th Annual Corn Breeders School, Meeting Proceedings, U. Illinois, p. 7–8 (Feb. 26–27 1990).

Tomes, D. T., et al., "Transgenic Tobacco Plants and their Progeny Derived by Microprojectile Bombardment of Tobacco Leaves," *Plant Mol. Biol.*, 14, 261–268 (Feb. 1990).

Twell, D., et al., "Transient Expression of Chimeric Genes Delivered into Pollen by Microprojectile Bombardment," *Plant Physiol.*, 91, 1271–1274 (1989).

Ulian, E., et al., "Transformation of Plants via the Shoot Apex," *In Vitro Cell. Dev. Biol.*, 9, 951–954 (1988).

Usami, S., et al., "Absence in Monocotyledonous Plants of the Diffusible Plant Factors including T–DNA Circularization and vir Gene Expression in *Agrobacterium*," *Mol. Gen. Genet.*, 209, 221–226 (1987).

Vain, P., et al., "Osmotic Pretreatment Enhances Particle Bombardment–Mediated Transient and Stable Transformation of Maize,"*Plant Cell Rep.*, 12, 84–88 (1993).

Vasil, I. K., "Transgenic Cereals Becoming a Reality," *Bio/Technol.*, 8, 797 (Sep. 1990).

Vasil, I. K., et al., "Culture of Protoplasts Isolated from Embryogenic Cell Suspension Cultures of Sugarcane and Maize," *IAPTC Abstract*, p. 443 (1986).

Vasil, V., et al., "Isolation and Maintenance of Embryogenic Cell Suspension Cultures of Gramineae," In: *Cell Culture and Somatic Cell Genetics of Plants*, vol. I, Academic Press, pp. 152–158 (1984).

Vasil, V., et al., "Plant Regeneration from Friable Embryonic Callus and Cell Suspension Cultures of Zea mays L.," *J. Plant Physiol.*, 124 399–408 (1986).

Walbot, V., et al., "Molecular genetics of corn," In: *Corn and Corn Improvement*, 3rd edition, Sprague, G. F., et al., (eds.), American Soc. Agronomy, Madison, WI, pp. 389–430 (1988).

Waldron, C., et al., "Resistance to Hygromycin B," *Plant Mol. Biol.*, 5, 103–108 (1985).

Walters, D. A., et al., "Transforamtion and Inheritance of Hygromycin Phosphotransferase Gene in Maize Plants," *Plant Molecular Biol.*, 18 189–200 (1992).

Wan, Y., et al., "Generation of Large Numbers of Independently Transformed Fertile Barley Planets,"*Plant Physiol.*, 104, 37–48 (1994).

Wan, Y., et al., "Maize Transformation and Regeneration of Transgenic Plants by Microprojectile Bombardment of Type I Calluas," Abstracts, 35th Annual Maize Genetics Conference, p. 5 (Mar. 18–21, 1993).

Wang, Y., et al., "Characterization of cis–Acting Elements Regulating Transcription from the Promoter of a Constitutively Active Rice Actin Gene," *Mol. Cell. Biol.*, 12, 3399–3406 (1992).

Wang, Y., et al., "Transient Expression of Foreign Genes in Rice, Wheat and Soybean Cells Following Particle Bombardment," *Plant Mol. Biol.*, 11, 433–439 (1988).

Weising K., et al., "Foreign Genes in Plants: Transfer, Structure, Expression and Applications," *Ann. Rev. Genet.*, 22, 421–478 (1988).

White, J., et al., "A Cassette Containing the bar Gene of *Streotomyces hygroscopicus*: a Selectable Marker for Plant Transformation," *Nuc. Acid. Res.*, 18, 1062 (1989).

Whiteley, H.R., et al., "The Molecular Biology of Parasporal Crystal Body Formation in *Bacillus thuringiensis*, *Ann. Rev. Microbiol.*, 40, 549–576 (1986).

Wong, E. Y., et al., *Arabidopis thaliana* Small Subunit Leader and Transit Peptide Enhance the Expression of *Bacillus thuringiensis* Proteins in Transgenic Plants,", *Plant Mol. Biol.*, 20, 81–93 (1992).

Yang, H., et al., "Production of Kanamycin Resistant Rice Tissues Following DNA Uptake into Protoplasts,"*Plant Cell Rep.*, 7, 421 (1988).

Yanisch–Perron, C., et al., "Improved M13 Phage Vectors and Host Strains: Nucleotide Sequences of M13mp 18 and pUC19 Vectors," *Gene*, 33, 103–119 (1985).

Yugari, Y., et al., "Coordinated End–Product Inhibition in Lysine Synthesis in *Escherichia coli*," *Biochem. Biophys. Acta.*, 62, 612–614 (1962).

Polylinker1:
0.10/Apa I, Xba I, Nsi I, Sph I, Xho I

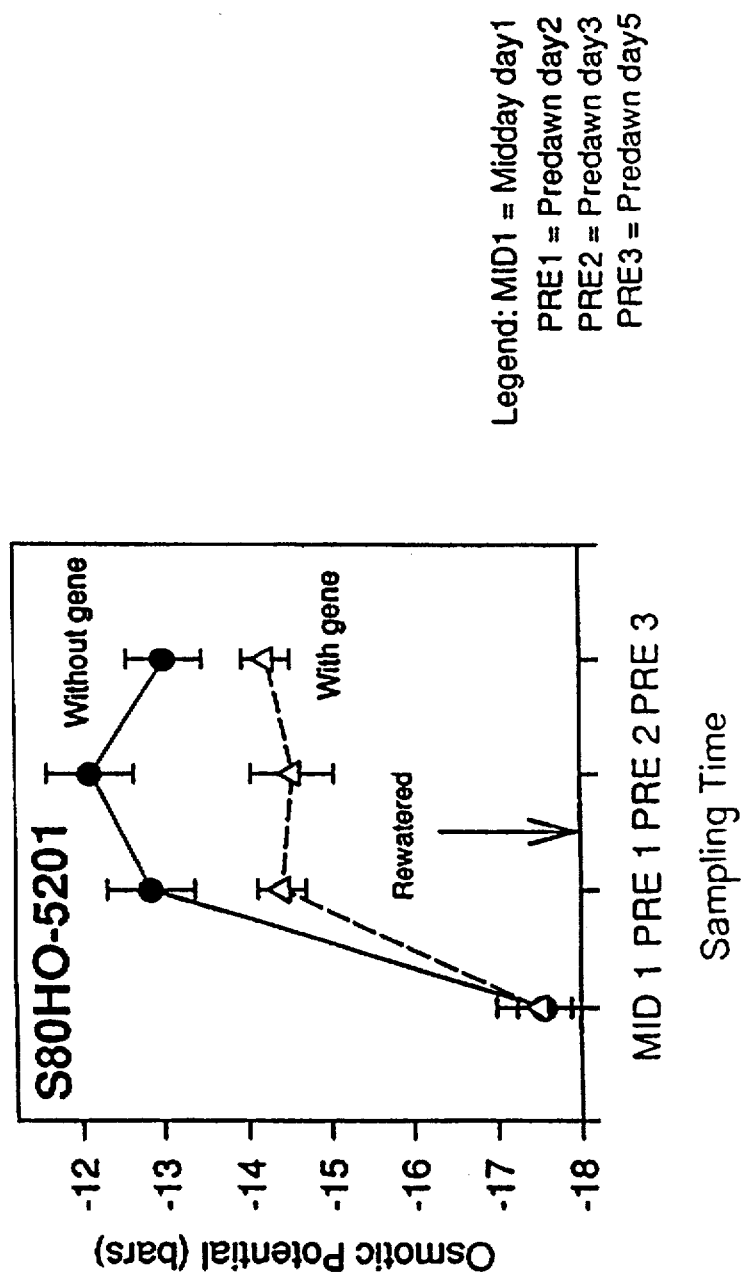

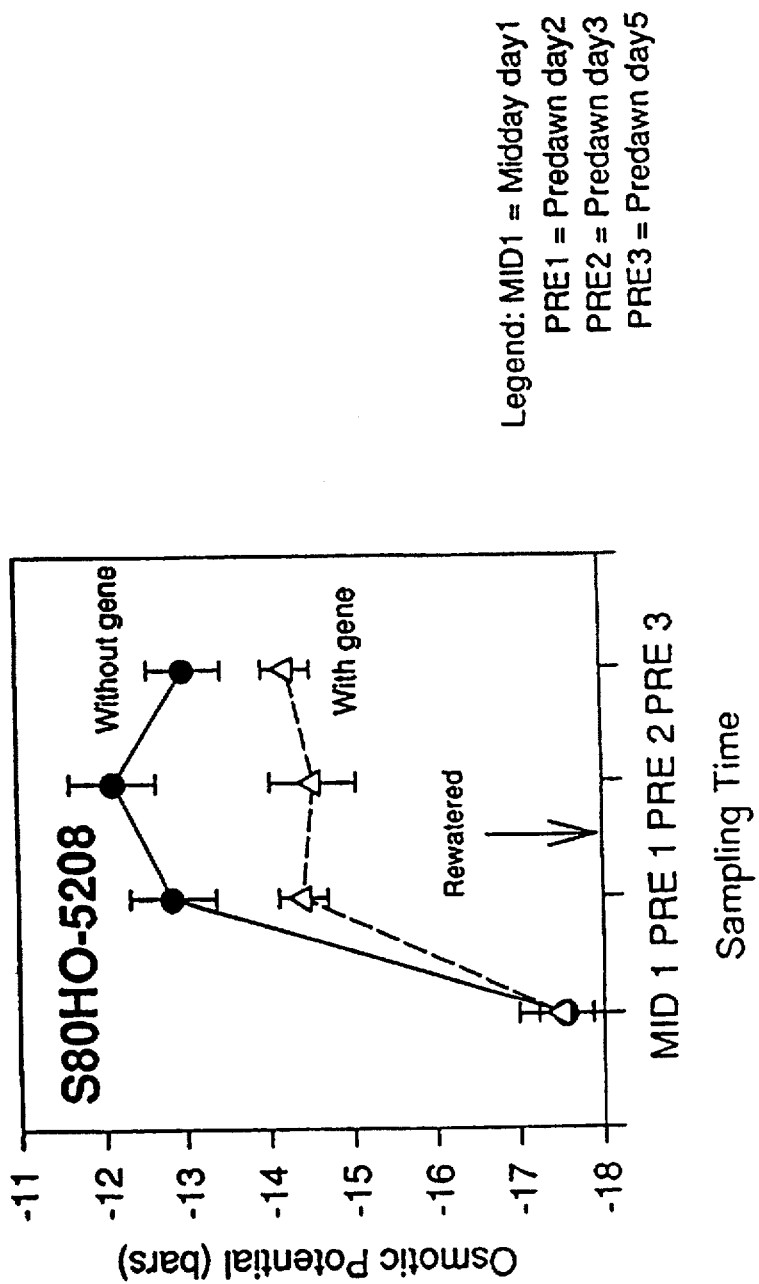

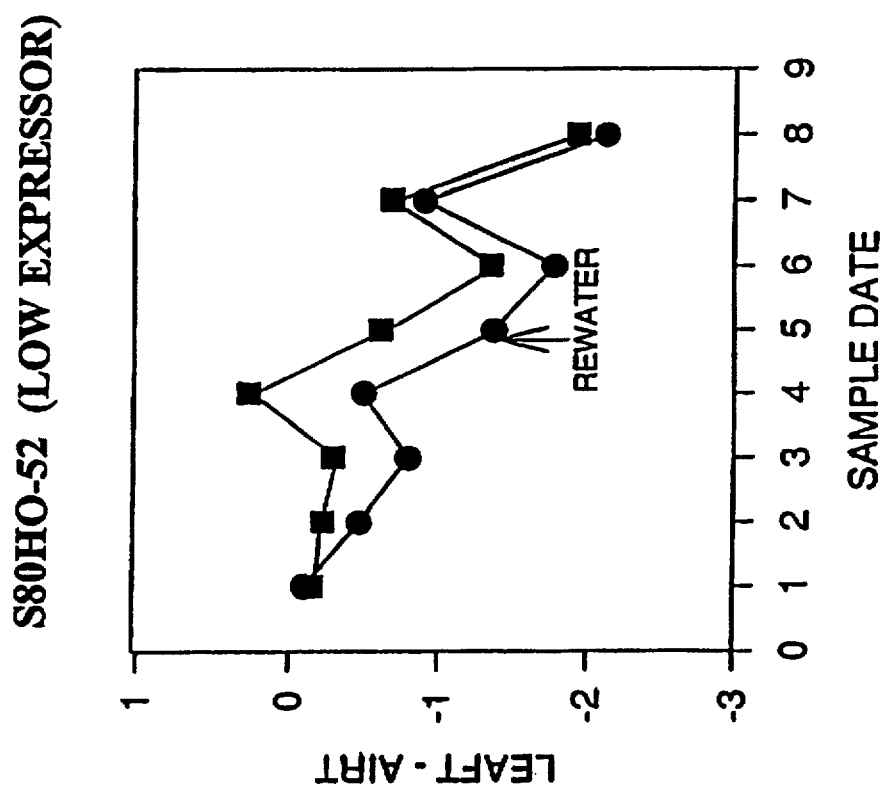

TRANSGENIC MAIZE WITH INCREASED MANNITOL CONTENT

CROSS-REFERENCE TO RELATED APPLICATIONS

This application is a continuation-in-part application of currently U.S. application Ser. No. 08/113,561, filed Aug. 25, 1993, which is incorporated by reference herein.

BACKGROUND OF THE INVENTION

Unpredictable rainfall, increases in soil salinity, and low temperature at the beginning or end of the growing season often result in decreased plant growth and crop productivity. These three environmental factors share at least one element of stress and that is water deficit or dehydration.

Drought is a significant problem in agriculture today. Over the last 40 years, for example, drought accounted for 74% of the total U.S. crop losses of corn (Agriculture, U. S. Department of, 1990. Agricultural Statistics. US Government Printing Office, Washington, D.C.). To sustain productivity under adverse environmental conditions, it is important to provide crops with a genetic basis for coping with water deficit, for example by breeding water retention and tolerance mechanisms into crops so that they can grow and yield under these adverse conditions.

When the rate of transpiration exceeds that of water uptake or supply, water deficit occurs and wilting symptoms appear. The responses of plants to water deficits include leaf rolling and shedding, stomata closure, leaf temperature increases, and wilting. Metabolism is also profoundly affected. General protein synthesis is inhibited and significant increases in certain amino acid pools, such as proline, become apparent (Barnett et al., Plant Physiol. 41, 1222 (1966)). During these water deficit periods, the photosynthetic rate decreases with the ultimate result of loss in yield (Boyer, J. S., In: Water deficits and plant growth, T. T. Kozlowski (ed.)., Academic Press, New York., pp. 154–190 (1976)). If carried to an extreme, severe water deficits result in death of the plant.

Several mechanisms appear to enable water deficit-tolerant plants to survive and produce. For example, a comparison of drought-resistant and drought-sensitive lines of Zea mays indicates that higher levels of abscisic acid (ABA), which is known to regulate stomata opening and perhaps other signal responses are correlated with resistance (Milborrow, B. V., In: The physiology and biochemistry of drought resistant plants, Paleg and Aspinall (eds.), Academic Press, N.Y., pp.348–388 (1981)). In addition, ABA-insensitive mutants and ABA-deficient mutants of Arabidopsis are prone to wilting (Koorneef et al., Theoret Appl Genet., 61, 385 (1982); Finkelstein et al., Plant Physiol. 94, 1172 (1990)).

Of the mechanisms employed by water deficit-tolerant plants to grow and yield, those with major impact on plant productivity are osmotic adjustment through the increased synthesis of osmoprotective metabolites, control over ion uptake and partitioning within the plant, ability to increase water intake, and acceleration of ontogeny. Examples of osmoprotective metabolites include sugars, such as sugar alcohols, proline, and glycine-betaine (Bohnert et al., The Plant Cell, 7, 1099 (1995); McCue et al., Tibtech, 8, 358 (1990)). Sugar alcohols, or polyols, such as mannitol and sorbitol, are major photosynthetic products of, and are known to accumulate to high levels in, various higher plant species. While mannitol is the most abundant sugar alcohol in at least 70 plant families, it is not produced at detectable levels in any important agricultural field or vegetable crop, other than celery (Apiaceae), coffee (Rubiaceae), and olive (Oleacea). Other sugar alcohols, such as ononitol and pinitol, are known to be produced in some plants under conditions of stress from drought, salt, or low temperature.

To produce a plant with a genetic basis for coping with water deficit, Tarczynski et al. (Proc. Natl. Acad. Sci. USA, 89, 2600 (1992); WO 92/19731, published No. 12, 1992; Science, 259, 508 (1993)) introduced the bacterial mannitol-1-phosphate dehydrogenase gene, mtlD, into tobacco cells via Agrobacterium-mediated transformation. Root and leaf tissues from transgenic plants regenerated from these transformed tobacco cells contained up to 100 mM mannitol. Control plants contained no detectable mannitol. To determine whether the transgenic tobacco plants exhibited increased tolerance to water deficit, Tarczynski et al. compared the growth of transgenic plants to that of untransformed control plants in the presence of 250 mM NaCl. After 30 days of exposure to 250 mM NaCl, transgenic plants had decreased weight loss and increased height relative to their untransformed counterparts. The authors concluded that the presence of mannitol in these transformed tobacco plants contributed to water deficit tolerance at the cellular level.

While Tarczynski et al. (WO 92/19731, published Nov. 12, 1992)) disclose that the same methodology might be applied to other higher plants, such as field crops, the introduction of exogenous DNA into monocotyledonous species and subsequent regeneration of transformed plants expressing useful phenotypic properties has proven much more difficult than transformation and regeneration of dicotyledonous plants.

Thus, there is a need for transgenic monocot plants that are resistant or tolerant to a reduction in water availability. Also, a method to produce transgenic monocot plants with increased levels of osmoprotectants is needed.

SUMMARY OF THE INVENTION

The present invention provides a method to increase water stress resistance or tolerance in a monocot plant cell or monocot plant, comprising introducing an expression cassette into the cells of a monocot plant to yield transformed monocot plant cells. Monocot plant cells include cells of monocotyledenous plants such as cereals, including corn (Zea mays), wheat, oats, rice, barley, millet and the like. The expression cassette comprises a preselected DNA segment encoding an enzyme which catalyzes the synthesis of an osmoprotectant, operably linked to a promoter functional in the monocot plant cell. The enzyme encoded by the DNA segment is expressed in the transformed monocot plant cells to increase the level of the osmoprotectant so as to render the transformed cells substantially tolerant or resistant to a reduction in water availability that inhibits the growth of untransformed cells of the plant.

As used herein, an "osmoprotectant" is an osmotically active molecule which, when that molecule is present in an effective amount in a cell or plant, confers water stress tolerance or resistance, or salt stress tolerance or resistance, to the cell or plant. Osmoprotectants include sugars such as monosaccharides, disaccharides, oligosaccharides, polysaccharides, sugar alcohols, and sugar derivatives, as well as proline and glycine-betaine. A preferred embodiment of the invention is an osmoprotectant that is a sugar. A more preferred embodiment of the invention is an osmoprotectant that is a sugar alcohol. Thus, useful osmoprotectants include fructose, erythritol, sorbitol, dulcitol, glucoglycerol, sucrose, stachyose, raffinose, ononitol, mannitol, inositol, methyl-inositol, galactol, hepitol, ribitol, xylitol, arabitol, trehalose, and pinitol. A preferred osmoprotectant of the invention is mannitol.

Genes which encode an enzyme that catalyzes the synthesis of an osmoprotectant include genes encoding mannitol dehydrogenase (Lee and Saier, *J. Bacteriol.*, 153 (1982)) and trehalose-6-phosphate synthase (Kaasen et al., *J. Bacteriol.*, 174, 889 (1992)). Through the subsequent action of native phosphatases in the cell or by the introduction and coexpression of a specific phosphatase, these introduced genes result in the accumulation of either mannitol or trehalose, respectively, both of which have been well documented as protective compounds able to mitigate the effects of stress. Mannitol accumulation in transgenic tobacco has been verified and preliminary results indicate that plants expressing high levels of this metabolite are able to tolerate an applied osmotic stress (Tarczynski et al., cited supra (1992), (1993)).

Also provided is an isolated transformed monocot plant cell and an isolated transformed monocot plant comprising said transformed cells, which cell and plant are substantially tolerant or resistant to a reduction in water availability. The cells of the transformed monocot plant comprise a recombinant DNA segment comprising a preselected DNA segment encoding an enzyme which catalyzes the synthesis of an osmoprotectant. The preselected DNA segment is present in the cells of the transformed plant and the enzyme encoded by the preselected DNA segment is expressed in those cells to yield an amount of osmoprotectant effective to confer tolerance or resistance to said cells to a reduction in water availability that inhibits the growth of the corresponding cells of the untransformed plant. A preferred embodiment of the invention includes a transformed monocot plant that has an improved osmotic potential when the total water potential of the transformed plant approaches zero relative to the osmotic potential of a corresponding untransformed plant.

Another preferred embodiment of the invention is an isolated transgenic *Zea mays* cell or plant, comprising a recombinant DNA segment comprising a promoter operably linked to a first DNA segment encoding an amino terminal chloroplast transit peptide operably linked to a second DNA segment encoding an enzyme which catalyzes the synthesis of an osmoprotectant. The enzyme encoded by the DNA sequence is expressed in the transgenic *Zea mays* plant or cell so that the level of the osmoprotectant in the cells of the transgenic *Zea mays* plant is substantially increased above the level in the cells of a *Zea mays* plant which only differ from the cells of the transgenic *Zea mays* plant in that the DNA segment is absent. The DNA segment is transmitted through a complete normal sexual cycle of the transgenic plant to its progeny and to further generations.

A further embodiment of the invention is a method for altering the sugar content in a monocot plant, such as a *Zea mays* plant, or monocot cell. The method comprises introducing an expression cassette into the cells of a monocot plant so as to yield transformed monocot plant cells. The expression cassette comprises a preselected DNA segment encoding an enzyme which catalyzes the synthesis of a sugar, operably linked to a promoter functional in the plant cells. A differentiated plant is regenerated from the transformed plant cells. The enzyme encoded by the preselected DNA segment is expressed in the cells of the differentiated plant in an amount effective to increase the sugar content in the cells of the differentiated plant relative to the sugar content in the cells of the untransformed differentiated plant.

Yet another embodiment of the invention is an isolated transformed monocot plant cell or transformed monocot plant, having an altered sugar cellular content. The transformed monocot comprises a recombinant DNA segment comprising a preselected DNA segment encoding an enzyme which catalyzes the synthesis of a sugar. The enzyme encoded by the DNA segment is expressed in an amount effective to alter the sugar content of the cells of the plant.

The present invention also provides an isolated transgenic *Zea mays* cell or plant, comprising a recombinant DNA segment comprising a promoter operably linked to a preselected DNA segment encoding an enzyme which catalyzes the synthesis of a sugar. The enzyme encoded by the recombinant DNA segment is expressed so that the level of sugar in the cells of the transgenic *Zea mays* plant is substantially increased above the level in the cells of a *Zea mays* plant which only differ from the cells of the transgenic *Zea mays* plant in which the recombinant DNA segment is absent. The recombinant DNA segment is transmitted through a complete normal sexual cycle of the transgenic plant to its progeny and further generations.

A preferred embodiment of the invention is a method for altering the mannitol content in a monocot plant cell or plant, such as a *Zea mays* plant. The method comprises introducing an expression cassette into the cells of the monocot plant so as to yield transformed plant cells. The expression cassette comprises a preselected DNA segment encoding an enzyme which catalyzes the synthesis of mannitol, operably linked to a promoter functional in the plant cell. A differentiated plant is regenerated from the transformed plant cells. The enzyme encoded by the DNA segment is expressed in the cells of the differentiated plant in an amount effective to increase the mannitol content in the cells of the differentiated plant relative to the mannitol content in the cells of an untransformed differentiated monocot plant.

Also provided is an isolated transformed monocot plant comprising an altered mannitol cellular content. The plant comprises a recombinant DNA segment comprising a preselected DNA segment encoding an enzyme which catalyzes the synthesis of mannitol. The enzyme encoded by the DNA is expressed in an amount effective to alter the mannitol content of the cells of the plant.

Another embodiment of the invention is a method to increase salt stress resistance or tolerance in a monocot plant. The method comprises introducing an expression cassette into the cells of a monocot plant. The expression cassette comprises a preselected DNA segment encoding an enzyme which catalyzes the synthesis of an osmoprotectant, operably linked to a promoter functional in a monocot plant cell, to yield transformed monocot plant cells. These transformed cells are regenerated to form a differentiated monocot plant. The enzyme encoded by the DNA segment is expressed so as to render the transformed monocot plant substantially resistant to an amount of salt that inhibits the growth of an untransformed monocot plant. Also provided is a transformed monocot plant which is salt stress tolerant or resistant. The cells of the plant comprise a recombinant DNA segment comprising a preselected DNA segment encoding an enzyme which catalyzes the synthesis of an osmoprotectant. The enzyme is expressed in the cells of the plant in an amount effective to confer tolerance or resistance to the transformed plant to an amount of salt that inhibits the growth of the corresponding untransformed plant.

As used herein, the term "salt" includes, but is not limited to, salts of agricultural fertilizers and salts associated with alkaline or acid soil conditions. A preferred salt of the invention is sodium chloride (NaCl).

The present invention also provides an expression cassette comprising a preselected DNA segment encoding an enzyme which catalyzes the synthesis of an osmoprotectant, operably linked to a promoter functional in a host cell. The promoter in the expression cassette is selected from, but not limited to, the group consisting of the Glb promoter, the AdhI promoter, and the ActI promoter.

Also provided is an expression cassette comprising a preselected first DNA segment encoding an enzyme which catalyzes the synthesis of an osmoprotectant, operably linked to a promoter functional in a host cell, wherein a second DNA segment separates the first preselected DNA segment encoding the enzyme from the promoter. A preferred second DNA segment is the AdhI intron 1.

Further provided is an expression cassette comprising a preselected first DNA segment encoding an enzyme which catalyzes the synthesis of an osmoprotectant, operably linked to a promoter functional in a host cell, wherein a second DNA segment encoding a maize chloroplast transit peptide is operably linked to the preselected first DNA segment encoding the enzyme.

As used herein, a "preselected" DNA sequence or segment is an exogenous or recombinant DNA sequence or segment that encodes an enzyme which catalyzes the synthesis of an osmoprotectant, such as a sugar. The enzyme preferably utilizes a substrate that is abundant in the plant cell. More preferably, the substrate is present in either, or both, the cytosol and chloroplasts of the plant cell. It is also preferred that the preselected DNA segment or sequence encode an enzyme that is active without a co-factor, or with a readily available co-factor. For example, the mtlD gene of E. Coli encodes a mannitol-1-phosphate dehydrogenase (M1PD). The only co-factor necessary for the enzymatic activity of M1PD in plants is NADH and the substrate for M1PD in plants is fructose-6-phosphate. Both NADH and fructose-6-phosphate are plentiful in higher plant cells.

As used herein, "substantially increased" or "elevated" levels of an osmoprotectant in a transformed plant cell, plant tissue, plant part, or plant, are greater than the levels in an untransformed plant cell, plant part, plant tissue, or plant, i.e., one where the genome has not been altered by the presence of a preselected DNA sequence. In the alternative, "substantially increased" or "elevated" levels of an osmoprotectant in a water-stressed transformed plant cell, plant tissue, plant part, or plant, are levels that are at least about 1.1 to 50 times, preferably at least about 2 to 30 times, and more preferably about 5–20 times, greater than the levels in a non-water-stressed transformed plant cell, plant tissue, plant part or plant.

For example, the levels of mannitol in a monocot plant transformed with a preselected DNA sequence encoding an enzyme which catalyzes the synthesis of mannitol, are compared to the levels in an untransformed plant. In the alternative, the levels of mannitol in a homozygous backcross converted inbred plant transformed with a preselected DNA sequence encoding an enzyme which catalyzes the synthesis of mannitol, are compared to the levels in a recurrent inbred plant. A homozygous backcross converted inbred transformed plant is a transformed plant which has been repeatedly crossed to the recurrent inbred parent until the transformed plant is substantially isogenic with the recurrent inbred parent except for the presence of the preselected DNA sequence, and is then self-pollinated (selfed) at least once, and preferably 5 or more times.

As used herein, "substantially isogenic" means that the genomic DNA content of a homozygous backcross converted inbred transformed plant is at least about 92%, preferably at least about 98%, and most preferably at least about 99%, identical to the genomic DNA content of a recurrent inbred parent of the transformed plant.

As used herein, a plant cell, plant part, plant tissue or plant that is "substantially resistant or tolerant" to a reduction in water availability is a plant cell, plant part, plant tissue, or plant that grows under water-stress conditions, e.g., high salt, low temperatures, or decreased water availability, that normally inhibit the growth of the untransformed plant cell, plant tissue, plant part, or plant, as determined by methodologies known to the art. Methodologies to determine plant growth or response to stress include, but are not limited to, height measurements, weight measurements, leaf area, plant water relations, ability to flower, ability to generate progeny, and yield. For example, a homozygous backcross converted inbred transformed plant of the invention has a superior osmotic potential during a water deficit relative to the corresponding, i.e., substantially isogenic, recurrent inbred plant.

As used herein, an "exogenous" gene or "recombinant" DNA is a DNA sequence or segment that has been isolated from a cell, purified, and amplified.

As used herein, the term "isolated" means either physically isolated from the cell or synthesized in vitro in the basis of the sequence of an isolated DNA segment.

As used herein, a "native" gene means a DNA sequence or segment that has not been manipulated in vitro, i.e., has not been isolated, purified, and amplified.

As used herein, "altered" levels of an osmoprotectant in a transformed plant, plant tissue, plant part, or plant cell are levels which are different, preferably greater, than the levels found in the corresponding untransformed plant, plant tissue, plant part, or plant cells. In the alternative, altered levels of the osmoprotectant in a backcross converted inbred transformed plant are different, preferably greater, than the levels found in the corresponding recurrent inbred plant.

DETAILED DESCRIPTION OF THE INVENTION

Figure 1:
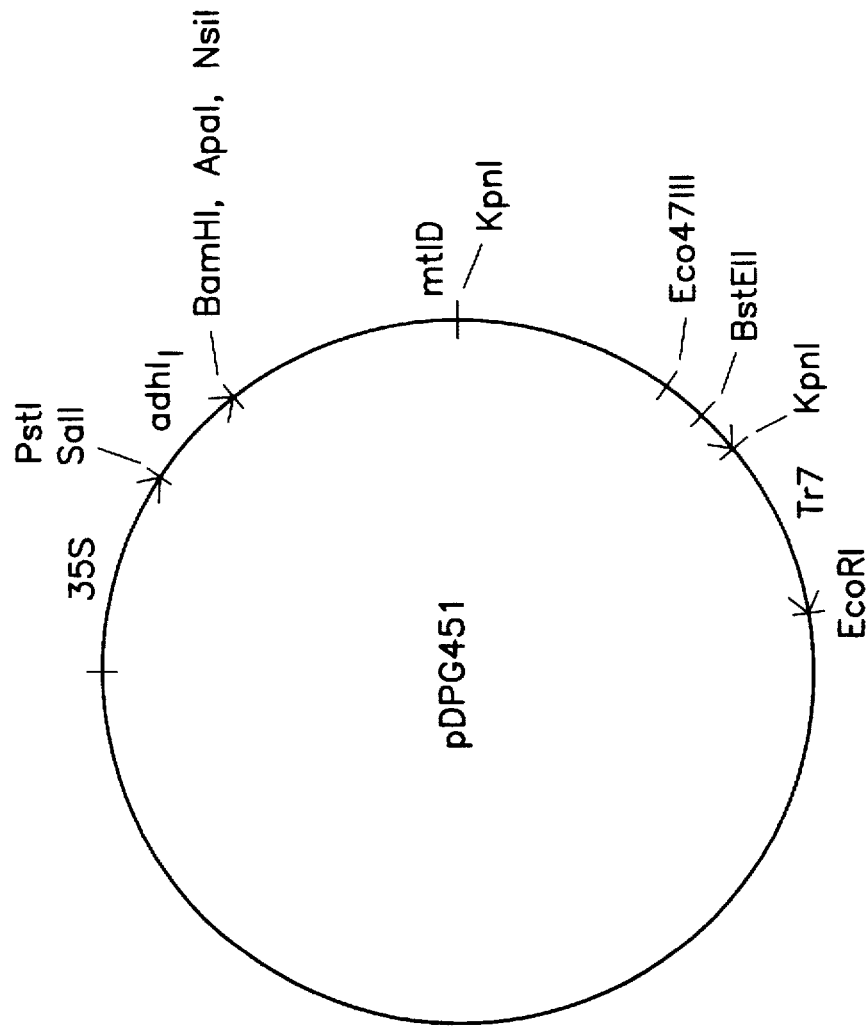
FIG. 1. A schematic diagram of plasmid pDPG451.

The identification and characterization of plants that are resistant or tolerant to water deprivation has long been a goal of agronomy. However, it has not been possible to accomplish the identification and isolation of genes that can provide resistance or tolerance to water stress. The insertion of such genes into monocots has the potential for long term improvement in, and expansion of, agriculture world-wide.

The ability of a plant to adapt to changes in water and salt concentrations is dependent on the ability of the plant to osmotically adjust its intracellular environment by altering the concentration of osmoprotectants within the cells of the plant. These osmoprotectants include, but are not limited to, various sugar molecules, such as monosaccharides, disaccharides, oligosaccharides, polysaccharides, sugar alcohols, and sugar derivatives. Thus, to provide a plant that is tolerant or resistant to a reduction in water availability, a preselected DNA segment or "gene" or "transgene" encoding an enzyme which catalyzes the synthesis of a particular osmoprotectant can be introduced into the genome of the plant. The osmoprotectant may be one that is not normally synthesized by the plant, but one which can be synthesized from a substrate that is abundant in the cells of the plant after the introduction of the preselected DNA segment. In the alternative, the osmoprotectant may be one that is naturally synthesized by the plant but the levels of the osmoprotectant in the plant are insufficient to render the plant tolerant to a reduction in water availability.

The accumulation of a non-naturally occurring osmoprotectant in a plant, plant cell, plant part, or plant tissue, could result in a detrimental effect because the substrate employed to synthesize the osmoprotectant is being depleted and a non-naturally occurring product is produced, which most likely would not be degraded. Moreover, a single introduced preselected DNA segment in the transgenic maize plant resulted in a beneficial effect to the transgenic maize plant when it is placed under water stress, i.e., the plant became more water stress-tolerant than its untransformed counterpart. Furthermore, the expression of the preselected DNA segment in the transgenic plant did not substantially affect the reproduction or growth of the plant, relative to its untransformed counterpart.

Thus, the present invention provides a method of genetically engineering monocot plants so as to produce altered agronomic or physiologic changes in the plants by the alteration in the levels of an osmoprotectant, such as a sugar, or more preferably a sugar alcohol, within the tissues of the plant. Alterations in these levels result in more negative osmotic water potentials in transformed plant tissues under either, or both, water stress or non-water stress conditions relative to the osmotic potentials in untransformed plant tissues.

Yet another embodiment of the invention is a method to confer tolerance or resistance to a reduction in water availability to a monocot plant, plant tissue, plant part or plant cell. Methods and compositions are provided for producing callus cultures, plant tissues, plants and seeds that are tolerant and/or resistant to a reduction in water availability under conditions that normally inhibit the function or growth of these cultures, tissues, plants or seeds. Such plants and seeds sexually can transmit this trait to their progeny.

The methods provided in the present invention may be used to produce increased levels of osmoprotectants, such as a sugar in monocots and other cereal crops including, but not limited to, maize, rice, rye, millet, wheat, barley, sorghum, and oats.

In accord with the present invention, a preselected DNA segment is identified, isolated, and combined with at least a promoter functional in a plant cell to provide a recombinant expression cassette. Once formed, an expression cassette comprising a preselected DNA segment can be subcloned into a known expression vector. Suitable known expression vectors include plasmids that autonomously replicate in prokaryotic and/or eukaryotic cells. Specific examples include plasmids such as pUC, pSK, pGEM, pBS and pSP-derived vectors, the pBI121 or pBI221 plasmid constructed as described by Jefferson (*Pl. Mol. Biol. Repr,* 5, 387 (1987)), or a binary Ti plasmid vector such as pG582 as described by An (*Plant Cell,* 1, 115 (1989)), and the like.

An expression cassette of the invention can be subcloned into an expression vector by standard methods. The expression vector can then be introduced into prokaryotic or eukaryotic cells by currently available methods including, but not limited to, protoplast transformation, *Agrobacterium*-mediated transformation, electroporation, microprojectile bombardment, tungsten whiskers (Coffee et al., U.S. Pat. No. 5,302,523, issued Apr. 12, 1994) and liposomes.

The vector can be introduced into prokaryotic cells such as *E. coil* or *Agrobacterium*. Transformed cells can be selected typically using a selectable or screenable marker encoded on the expression vector.

The expression cassette or vector can be introduced into monocot plant cells. Plant cells useful for transformation include callus, immature embryos, meristematic tissue, gametic tissue, or cultured suspension cells. Optionally, other preselected DNA segments encoding enzymes which catalyze the synthesis of osmoprotectants can be introduced into the plant cell. The transformed plant cell can then be regenerated into a plant and the plant tested for its ability to grow or thrive under stress conditions, such as high salinity or reduced water availability. Depending on the type of plant, the level of gene expression, and the activity of the enzyme encoded by the preselected DNA segment, introduction of the preselected DNA into the plant can confer the phenotype of tolerance or resistance to water deficit to the plant.

The introduced preselected DNA segments can be expressed in the transformed monocot plant cells and stably transmitted (somatically and sexually) to the next generation of cells produced. The vector should be capable of introducing, maintaining, and expressing a preselected DNA segment in plant cells, wherein the preselected DNA can be obtained from a variety of sources, including but not limited to plants and animals, bacteria, fungi, yeast or virus. Additionally, it should be possible to introduce the vector into a wide variety of cells of monocot plants. The preselected DNA segment is passed on to progeny by normal sexual transmission.

Introduction and expression of foreign genes in dicotyledonous (broad-leafed) plants such as tobacco, potato and alfalfa has been shown to be possible using the T-DNA of the tumor-inducing (Ti) plasmid of *Agrobacterium tumefaciens*. Using recombinant DNA techniques and bacterial genetics, a wide variety of foreign DNAs can be inserted into T-DNA in *Agrobacterium*. Following infection by the bacterium containing the recombinant Ti plasmid, the foreign DNA is inserted into the host plant chromosomes, thus producing a genetically engineered cell and eventually a genetically engineered plant. A second approach is to introduce root-inducing (Ri) plasmids as the gene vectors.

While *Agrobacterium* appear to attack only dicots, many important crop plants including maize, wheat, rice, barley, oats, sorghum, millet, and rye are monocots and are not known to be susceptible to transformation by *Agrobacterium*. The Ti plasmid, however, may be manipulated in the future to act as a vector for monocot plants. Additionally, using the Ti plasmid as a model system, it may be possible to artificially construct transformation vectors for monocot plants. Ti-plasmids might also be introduced into monocots by artificial methods such as microinjection, or fusion between monocot protoplasts and bacterial spheroplasts containing the T-region, which can then be integrated into the plant nuclear DNA.

Transformation of plant cells with a preselected DNA segment may also be accomplished by introducing a preselected DNA into other nucleic acid molecules that can transfer the inserted DNA into a plant genome, e.g., plant pathogens such as DNA viruses like CaMV or geminiviruses, RNA viruses, and viroids; DNA molecules derived from unstable plant genome components like extrachromosomal DNA elements in organelles (e.g., chloroplasts or mitochondria), or nuclearly encoded controlling elements; DNA molecules from stable plant genome components (e.g., origins of replication and other DNA sequences which allow introduced DNA to integrate into the organellar or nuclear genomes and to replicate normally, to autonomously replicate, to segregate normally during cell division and sexual reproduction of the plant and to be inherited in succeeding generations of plants) or transposons.

A preselected DNA may be delivered into plant cells or tissues directly by microorganisms with infectious plasmids, infectious viruses, the use of liposomes, microinjection by mechanical or laser beam methods, by whole chromosomes or chromosome fragments, electroporation, and microprojectile bombardment.

I. Recipient Cells

Practicing the present invention includes the generation and use of recipient cells. As used herein, the term "recipient cells" refers to monocot cells that are receptive to transformation and subsequent regeneration into stably transformed, fertile monocot plants.

A. Sources of Cells

Recipient cell targets include, but are not limited to, meristem cells, Type I, Type II, and Type III callus, immature embryos and gametic cells such as microspores pollen, sperm and egg cells. Type I, Type II, and Type III callus may be initiated from tissue sources including, but not limited to, immature embryos, seedling apical meristems, microspores and the such. Those cells which are capable of proliferating as callus are also recipient cells for genetic transformation. The present invention provides techniques for transforming immature embryos followed by initiation of callus and subsequent regeneration of fertile transgenic plants. Direct transformation of immature embryos obviates the need for long term development of recipient cell cultures. Pollen, as well as its precursor cells, microspores, may be capable of functioning as recipient cells for genetic transformation, or as vectors to carry foreign DNA for incorporation during fertilization. Direct pollen transformation would obviate the need for cell culture. Meristematic cells (i.e., plant cells capable of continual cell division and characterized by an undifferentiated cytological appearance, normally found at growing points or tissues in plants such as root tips, stem apices, lateral buds, etc.) may represent another type of recipient plant cell. Because of their undifferentiated growth and capacity for organ differentiation and totipotency, a single transformed meristematic cell could be recovered as a whole transformed plant. In fact, it is proposed that embryogenic suspension cultures may be an in vitro meristematic cell system, retaining an ability for continued cell division in an undifferentiated state, controlled by the media environment.

In certain embodiments, cultured plant cells that can serve as recipient cells for transforming with desired DNA segments include maize cells, and more specifically, cells from *Zea mays* L. Somatic cells are of various types. Embryogenic cells are one example of somatic cells which may be induced to regenerate a plant through embryo formation. Non-embryogenic cells are those which will typically not respond in such a fashion. An example of non-embryogenic cells are certain Black Mexican Sweet (BMS) maize cells. These cells have been transformed by microprojectile bombardment using the neo gene followed by selection with the aminoglycoside, kanamycin (Klein et al., *Plant Physiol.*, 91, 440 (1989)). However, this BMS culture was not found to be regenerable.

The development of embryogenic maize calli and suspension cultures useful in the context of the present invention, e.g., as recipient cells for transformation, has been described in Gordon et al. (U.S. Pat. No. 5,134,074, issued Jul. 28, 1992, incorporated herein by reference).

The present invention also provides certain techniques that may enrich recipient cells within a cell population. For example, Type II callus development, followed by manual selection and culture of friable, embryogenic tissue, generally results in an enrichment of recipient cells for use in, e.g., microprojectile transformation. Suspension culturing, particularly using the media disclosed herein, may also improve the ratio of recipient to non-recipient cells in any given population. Manual selection techniques which employed to select recipient cells may include, e.g., assessing cell morphology and differentiation, or may use various physical or biological means. Cryopreservation is also contemplated as a possible method of selecting for recipient cells.

Manual selection of recipient cells, e.g., by selecting embryogenic cells from the surface of a Type II callus, is one means employed in an attempt to enrich for recipient cells prior to culturing (whether cultured on solid media or in suspension). The preferred cells may be those located at the surface of a cell cluster, and may further be identifiable by their lack of differentiation, their size and dense cytoplasm. The preferred cells will generally be those cells which are less differentiated, or not yet committed to differentiation. Thus, one may wish to identify and select those cells which are cytoplasmically dense, relatively unvacuolated with a high nucleus to cytoplasm ratio (e.g., determined by cytological observations), small in size (e.g., 10–20 µm), and capable of sustained divisions and somatic proembryo formation.

It is proposed that other means for identifying such cells may also be employed. For example, through the use of dyes, such as Evan's blue, which are excluded by cells with relatively non-permeable membranes, such as embryogenic cells, and taken up by relatively differentiated cells such as root-like cells and snake cells (so-called due to their snake-like appearance).

Other possible means of identifying recipient cells include the use of isozyme markers of embryogenic cells, such as glutamate dehydrogenase, which can be detected by cytochemical stains (Fransz et al., *Plant Cell Rep.*, 8, 67 (1989)). However, it is cautioned that the use of isozyme markers such as glutamate dehydrogenase may lead to some degree of false positives from non-embryogenic cells such as rooty cells which nonetheless have a relatively high metabolic activity.

B. Media

In certain embodiments, recipient cells are selected following growth in culture. Where employed, cultured cells will preferably be grown either on solid supports or in the form of liquid suspensions. In either instance, nutrients may be provided to the cells in the form of media, and environmental conditions controlled. There are many types of tissue culture media comprised of amino acids, salts, sugars, growth regulators and vitamins. Most of the media employed in the practice of the invention will have some similar components (see, e.g., Table 1 hereinbelow), the media differ in the composition and proportions of their ingredients depending on the particular application envisioned. For example, various cell types usually grow in more than one type of media, but will exhibit different growth rates and different morphologies, depending on the growth media. In some media, cells survive but do not divide.

Various types of media suitable for culture of plant cells have been previously described. Examples of these media include, but are not limited to, the N6 medium described by Chu et al. (*Scientia Sinica*, 18, 659 (1975)) and MS media described by Murashige & Skoog (*Plant Physiol.*, 15, 473 (1962)). Media such as MS which have a high ammonia/nitrate ratio are counterproductive to the generation of recipient cells in that they promote loss of morphogenic capacity. N6 media, on the other hand, has a somewhat lower ammonia/nitrate ratio, and is contemplated to promote the generation of recipient cells by maintaining cells in a proembryonic state capable of sustained divisions.

C. Cell Cultures

1. Initiation

In the practice of the invention it is sometimes, but not always, necessary to develop cultures which contain recipient cells. Suitable cultures can be initiated from a number of whole plant tissue explants including, but not limited to, immature embryos, leaf bases, immature tassels, anthers, microspores, and other tissues containing cells capable of in vitro proliferation and regeneration of fertile plants. In one exemplary embodiment, recipient cell cultures are initiated from immature embryos of *Zea mays* L. by growing excised immature embryos on a solid culture medium containing growth regulators including, but not limited to, dicamba, 2,4-D, NAA, and IAA. In some instances it will be preferred to add silver nitrate to culture medium for callus initiation as this compound has been reported to enhance culture initiation (Vain et al., *Plant Cell, tissue and Organ Culture.*, 18 143 (1989)). Embryos will produce callus that varies greatly in morphology including from highly unorganized cultures containing very early embryogenic structures (such as, but not limited to, type II cultures in maize), to highly organized cultures containing large late embryogenic structures (such as, but not limited to, type I cultures in maize). This variation in culture morphology may be related to genotype, culture medium composition, size of the initial embryos and other factors. Each of these types of culture morphologies is a source of recipient cells.

The development of suspension cultures capable of plant regeneration may be used in the context of the present invention. Suspension cultures may be initiated by transferring callus tissue to liquid culture medium containing growth regulators. Addition of coconut water or other substances to suspension culture medium may enhance growth and culture morphology, but the utility of suspension cultures is not limited to those containing these compounds. In some embodiments of this invention, the use of suspension cultures will be preferred as these cultures grow more rapidly and are more easily manipulated than callus cells growing on solid culture medium.

When immature embryos or other tissues directly removed from a whole plant are used as the target tissue for DNA delivery, it will only be necessary to initiate cultures of cells insofar as is necessary for identification and isolation of transformants. In an illustrative embodiment, DNA is introduced by particle bombardment into immature embryos following their excision from the plant. Embryos are transferred to a culture medium that will support proliferation of tissues and allow for selection of transformed sectors, at about 0–14 days following DNA delivery. In this embodiment of the invention it is not necessary to establish stable callus cultures capable of long term maintenance and plant regeneration.

2. Maintenance

The method of maintenance of cell cultures may contribute to their utility as sources of recipient cells for transformation. Manual selection of cells for transfer to fresh culture medium, frequency of transfer to fresh culture medium, composition of culture medium, and environment factors including, but not limited to, light quality and quantity and temperature are all important factors in maintaining callus and/or suspension cultures that are useful as sources of recipient cells. It is contemplated that alternating callus between different culture conditions may be beneficial in enriching for recipient cells within a culture. For example, it is proposed that cells may be cultured in suspension culture, but transferred to solid medium at regular intervals. After a period of growth on solid medium cells can be manually selected for return to liquid culture medium. It is proposed that by repeating this sequence of transfers to fresh culture medium it is possible to enrich for recipient cells. It is also contemplated that passing cell cultures through a sieve, e.g., a 1.9 mm sieve, is useful in maintaining the friability of a callus or suspension culture and may be beneficial is enriching for transformable cells.

3. Cryopreservation

Additionally, cryopreservation may effect the development of, or perhaps select for, recipient cells. Cryopreservation selection may operate due to a selection against highly vacuolated, non-embryogenic cells, which may be selectively killed during cryopreservation. There is a temporal window in which cultured cells retain their regenerative ability, thus, it is believed that they must be preserved at or before that temporal period if they are to be used for future transformation and regeneration.

For use in transformation, suspension or callus culture cells may be cryopreserved and stored for periods of time, thawed, then used as recipient cells for transformation. An illustrative embodiment of cryopreservation methods comprises the steps of slowly adding cryoprotectants to suspension cultures to give a final concentration of 10% dimethyl sulfoxide, 10% polyethylene glycol (6000 MW), 0.23 M proline and 0.23 M glucose. The mixture is then cooled to −35° C. at 0.5° C. per minute. After an isothermal period of 45 minutes, samples are placed in liquid $N_2$ (modification of methods of Withers et al., *Plant Physiol.*, 64, 675 (1979); and Finkle et al., *Plant Sci.*, 42, 133 (1985)). To reinitiate suspension cultures from cryopreserved material, cells may be thawed rapidly and pipetted onto feeder plates similar to those described by Vaeck et al. (*Nature*, 328, 33 (1987)).

II. DNA Sequences

Virtually any DNA composition may be used for delivery to recipient monocotyledonous cells to ultimately produce fertile transgenic plants in accordance with the present invention. For example, a preselected DNA segment encoding a gene product whose expression confers an increase in intracellular mannitol levels, or drought resistance, in the form of vectors and plasmids, or linear DNA fragments, in some instances containing only the DNA element to be expressed in the plant, and the like, may be employed.

In certain embodiments, it is contemplated that one may wish to employ replication-competent viral vectors in monocot transformation. Such vectors include, for example, wheat dwarf virus (WDV) "shuttle" vectors, such as pW1-11 and PW1-GUS (Ugaki et al., *Nucl. Acid Res.*, 19, 391 (1991)). These vectors are capable of autonomous replication in maize cells as well as *E. coli*, and as such may provide increased sensitivity for detecting DNA delivered to transgenic cells. A replicating vector may also be useful for delivery of genes flanked by DNA sequences from transposable elements such as Ac, Ds, or Mu. It has been proposed (Laufs et al., *Proc. Natl. Acad. Sci. USA*, 87, 7752 (1990)) that transposition of these elements within the maize genome requires DNA replication. It is also contemplated that transposable elements would be useful for introducing DNA fragments lacking elements necessary for selection and maintenance of the plasmid vector in bacteria, e.g., antibiotic resistance genes and origins of DNA replication. It is also proposed that use of a transposable element such as Ac, Ds, or Mu would actively promote integration of the desired DNA and hence increase the frequency of stably transformed cells.

Vectors, plasmids, cosmids, YACs (yeast artificial chromosomes) and DNA segments for use in transforming such cells will, of course, generally comprise the preselected cDNA(s), preselected DNA(s) or genes which one desires to introduce into the cells. These DNA constructs can further include structures such as promoters, enhancers, polylinkers, or even regulatory genes as desired. The DNA segment or gene chosen for cellular introduction will often encode a protein which will be expressed in the resultant recombinant cells, such as will result in a screenable or selectable trait and/or which will impart an improved phenotype to the regenerated plant. However, this may not always be the case, and the present invention also encompasses transgenic plants incorporating non-expressed transgenes related to drought-resistance or mannitol expression.

DNA useful for introduction into maize cells includes that which has been derived or isolated from any source, that may be subsequently characterized as to structure, size and/or function, chemically altered, and later introduced into maize. An example of DNA "derived" from a source, would be a DNA sequence or segment that is identified as a useful fragment within a given organism, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g. amplified, for use in the invention, by the methodology of genetic engineering. Such DNA is commonly referred to as "recombinant DNA."

Therefore useful DNA includes completely synthetic DNA, semi-synthetic DNA, DNA isolated from biological sources, and DNA derived from RNA. It is within the scope of the invention to isolate a preselected DNA segment from a given maize genotype, and to subsequently introduce multiple copies of the preselected DNA segment into the same genotype, e.g., to enhance production of a given gene product such as a protein that confers tolerance or resistance to water deficit.

The introduced DNA includes, but is not limited to, DNA from plant genes, and non-plant genes such as those from bacteria, yeasts, animals or viruses. The introduced DNA can include modified genes, portions of genes, or chimeric genes, including genes from the same or different maize genotype. The term "chimeric gene" or "chimeric DNA" is defined as a gene or DNA sequence or segment comprising at least two DNA sequences or segments from species which do not combine DNA under natural conditions, or which DNA sequences or segments are positioned or linked in a manner which does not normally occur in the native genome of untransformed maize, or other monocot.

The introduced DNA used for transformation herein may be circular or linear, double-stranded or single-stranded. Generally, the DNA is in the form of chimeric DNA, such as plasmid DNA, that can also contain coding regions flanked by regulatory sequences which promote the expression of the recombinant DNA present in the resultant maize plant. For example, the DNA may itself comprise or consist of a promoter that is active in maize which is derived from a non-maize source, or may utilize a promoter already present in the maize genotype that is the transformation target.

Generally, the introduced DNA will be relatively small, i.e., less than about 30 kb to minimize any susceptibility to physical, chemical, or enzymatic degradation which is known to increase as the size of the DNA increases. As noted above, the number of proteins, RNA transcripts or mixtures thereof which is introduced into the maize genome is preferably preselected and defined, e.g., from one to about 5–10 such products of the introduced DNA may be formed.

A. Regulatory Elements

The construction of vectors which may be employed in conjunction with the present invention will be known to those of skill of the art in light of the present disclosure.

Ultimately, the most desirable DNA segments for introduction into a monocot genome may be homologous genes or gene families which encode a desired trait (e.g., increased yield per acre) and which are introduced under the control of novel promoters or enhancers, etc., or perhaps even homologous or tissue-specific (e.g., root-, collar/sheath-, whorl-, stalk-, earshank-, kernel- or leaf-specific) promoters or control elements. Indeed, it is envisioned that a particular use of the present invention will be the targeting of a preselected DNA segment in a tissue- or organelle- or turgor- specific manner.

Vectors for use in tissue-specific targeting of a preselected DNA segment in transgenic plants will typically include tissue-specific promoters and may also include other tissue-specific control elements such as enhancer sequences. Promoters which direct specific or enhanced expression in certain plant tissues will be known to those of skill in the art in light of the present disclosure. These include, for example, the rbcS promoter, specific for green tissue; the ocs, nos and mas promoters which have higher activity in roots or wounded leaf tissue; a truncated (−90 to +8) 35S promoter which directs enhanced expression in roots, an α-tubulin gene that directs expression in roots and promoters derived from zein storage protein genes which direct expression in endosperm. It is particularly contemplated that one may advantageously use the 16 bp ocs enhancer element from the octopine synthase (ocs) gene (Ellis et al., supra (1987); Bouchez et al., supra (1989)), especially when present in multiple copies, to achieve enhanced expression in roots.

B. Marker Genes

In order to improve the ability to identify transformants, one may desire to employ a selectable or screenable marker gene as, or in addition to, the expressible preselected DNA segment. "Marker genes" are genes that impart a distinct phenotype to cells expressing the marker gene and thus allow such transformed cells to be distinguished from cells that do not have the marker. Such genes may encode either a selectable or screenable marker, depending on whether the marker confers a trait which one can 'select' for by chemical means, i.e., through the use of a selective agent (e.g., a herbicide, antibiotic, or the like), or whether it is simply a trait that one can identify through observation or testing, i.e., by 'screening' (e.g., the R-locus trait). Of course, many examples of suitable marker genes are known to the art and can be employed in the practice of the invention.

Included within the terms selectable or screenable marker genes are also genes which encode a "secretable marker" whose secretion can be detected as a means of identifying or selecting for transformed cells. Examples include markers which encode a secretable antigen that can be identified by antibody interaction, or even secretable enzymes which can be detected by their catalytic activity. Secretable proteins fall into a number of classes, including small, diffusible proteins detectable, e.g., by ELISA; and proteins that are inserted or trapped in the cell wall (e.g., proteins that include a leader sequence such as that found in the expression unit of extensin or tobacco PR-S).

With regard to selectable secretable markers, the use of a gene that encodes a protein that becomes sequestered in the cell wall, and which protein includes a unique epitope is considered to be particularly advantageous. Such a secreted antigen marker would ideally employ an epitope sequence that would provide low background in plant tissue, a promoter-leader sequence that would impart efficient expression and targeting across the plasma membrane, and would produce protein that is bound in the cell wall and yet accessible to antibodies. A normally secreted wall protein modified to include a unique epitope would satisfy all such requirements.

One example of a protein suitable for modification in this manner is extensin, or hydroxyproline rich glycoprotein (HPRG). The use of the maize HPRG (Steifel et al., *The Plant Cell*, 2, 785 (1990)) is preferred as this molecule is well characterized in terms of molecular biology, expression, and protein structure. However, any one of a variety of extensins and/or glycine-rich wall proteins (Keller et al., *EMBO J.*, 8, 1309 (1989)) could be modified by the addition of an antigenic site to create a screenable marker.

Elements of the present disclosure are exemplified in detail through the use of particular marker genes, however in light of this disclosure, numerous other possible selectable and/or screenable marker genes will be apparent to those of skill in the art in addition to the one set forth hereinbelow. Therefore, it will be understood that the following discussion is exemplary rather than exhaustive. In light of the techniques disclosed herein and the general recombinant techniques which are known in the art, the present invention renders possible the introduction of any gene, including marker genes, into a recipient cell to generate a transformed monocot.

1. Selectable Markers

Possible selectable markers for use in connection with the present invention include, but are not limited to, a neo gene (Potrykus et al., *Mol. Gen. Genet.*, 199, 183 (1985)) which codes for kanamycin resistance and can be selected for using kanamycin, G418, and the like; a bar gene which codes for bialaphos resistance; a gene which encodes an altered EPSP synthase protein (Hinchee et al., *Biotech.*, 6, 915 (1988)) thus conferring glyphosate resistance; a nitrilase gene such as bxn from *Klebsiella ozaenae* which confers resistance to bromoxynil (Stalker et al., *Science*, 242, 419 (1988)); a mutant acetolactate synthase gene (ALS) which confers resistance to imidazolinone, sulfonylurea or other ALS-inhibiting chemicals (European Patent Application 154,204, 1985); a methotrexate-resistant DHFR gene (Thillet et al., *J. Biol. Chem.*, 263, 12500 (1988)); a dalapon dehalogenase gene that confers resistance to the herbicide dalapon; or a mutated anthranilate synthase gene that confers resistance to 5-methyl tryptophan. Where a mutant EPSP synthase gene is employed, additional benefit may be realized through the incorporation of a suitable chloroplast transit peptide, CTP (European Patent Application 0,218,571, 1987).

An illustrative embodiment of a selectable marker gene capable of being used in systems to select transformants is the genes that encode the enzyme phosphinothricin acetyltransferase, such as the bar gene from *Streptomyces hygroscopicus* or the pat gene from *Streptomyces viridochromogenes* (U.S. patent application Ser. No. 07/565,844, which is incorporated by reference herein). The enzyme phosphinothricin acetyl transferase (PAT) inactivates the active ingredient in the herbicide bialaphos, phosphinothricin (PPT). PPT inhibits glutamine synthetase, (Murakami et al., *Mol. Gen. Genet.*, 205, 42 (1986); Twell et al., *Plant Physiol.*, 91, 1270 (1989)) causing rapid accumulation of ammonia and cell death. The success in using this selective system in conjunction with monocots was particularly surprising because of the major difficulties which have been reported in transformation of cereals (Potrykus, *Trends Biotech.*, 7, 269 (1989)).

2. Screenable Markers

Screenable markers that may be employed include, but are not limited to, a β-glucuronidase or uidA gene (GUS) which encodes an enzyme for which various chromogenic substrates are known; an R-locus gene, which encodes a product that regulates the production of anthocyanin pigments (red color) in plant tissues (Dellaporta et al., in *Chromosome Structure and Function*, pp. 263–282 (1988)); a β-lactamase gene (Sutcliffe, *PNAS USA*, 75, 3737 (1978)), which encodes an enzyme for which various chromogenic substrates are known (e.g., PADAC, a chromogenic cephalosporin); a xylE gene (Zukowsky et al., *PNAS USA*, 80, 1101 (1983)) which encodes a catechol dioxygenase that can convert chromogenic catechols; an α-amylase gene (Ikuta et al., *Biotech.*, 8, 241 (1990)); a tyrosinase gene (Katz et al., *J. Gen. Microbiol.*, 129, 2703 (1983)) which encodes an enzyme capable of oxidizing tyrosine to DOPA and dopaquinone which in turn condenses to form the easily detectable compound melanin; a β-galactosidase gene, which encodes an enzyme for which there are chromogenic substrates; a luciferase (lux) gene (Ow et al., *Science*, 234, 856 (1986)), which allows for bioluminescence detection; or even an aequorin gene (Prasher et al., *Biochem. Biophys. Res. Comm.*, 126, 1259 (1985)), which may be employed in calcium-sensitive bioluminescence detection, or a green fluorescent protein gene (Niedz et al., *Plant Cell Reports*, 14, 403 (1995)).

Genes from the maize R gene complex are contemplated to be particularly useful as screenable markers. The R gene complex in maize encodes a protein that acts to regulate the production of anthocyanin pigments in most seed and plant tissue. Maize strains can have one, or as many as four, R alleles which combine to regulate pigmentation in a developmental and tissue specific manner. A gene from the R gene complex was applied to maize transformation, because the expression of this gene in transformed cells does not harm the cells. Thus, an R gene introduced into such cells will cause the expression of a red pigment and, if stably incorporated, can be visually scored as a red sector. If a maize line is carries dominant alleles for genes encoding the enzymatic intermediates in the anthocyanin biosynthetic pathway (C2, A1, A2, Bz1 and Bz2), but carries a recessive allele at the R locus, transformation of any cell from that line with R will result in red pigment formation. Exemplary lines include Wisconsin 22 which contains the rg-Stadler allele and TR112, a K55 derivative which is r-g, b, P1. Alternatively any genotype of maize can be utilized if the C1 and R alleles are introduced together.

It is further proposed that R gene regulatory regions may be employed in chimeric constructs in order to provide mechanisms for controlling the expression of chimeric genes. More diversity of phenotypic expression is known at the R locus than at any other locus (Coe et al., In: *Corn and Corn Improvement*, Sprague et al. (eds.) pp. 81–258 (1988)). It is contemplated that regulatory regions obtained from regions 5' to the structural R gene would be valuable in directing the expression of genes, e.g., insect resistance, drought resistance, herbicide tolerance or other protein coding regions. For the purposes of the present invention, it is believed that any of the various R gene family members may be successfully employed (e.g., P, S, Lc, etc.). However, the most preferred will generally be Sn (particularly Sn:bol3). Sn is a dominant member of the R gene complex and is functionally similar to the R and B loci in that Sn controls the tissue specific deposition of anthocyanin pigments in certain seedling and plant cells, therefore, its phenotype is similar to R.

A further screenable marker contemplated for use in the present invention is firefly luciferase, encoded by the lux gene. The presence of the lux gene in transformed cells may be detected using, for example, X-ray film, scintillation counting, fluorescent spectrophotometry, low-light video cameras, photon counting cameras or multiwell luminometry. It is also envisioned that this system may be developed for populational screening for bioluminescence, such as on tissue culture plates, or even for whole plant screening.

C. Transgenes for Maize Modification

Improvement of the ability of maize to tolerate various environmental stresses including, but not limited to, drought, excess moisture, chilling, freezing, high temperature, salt, and oxidative stress, can be effected through expression of heterologous, or overexpression of homologous, genes.

Expression of novel preselected DNA segments that favorably effect plant water content, total water potential, osmotic potential, and turgor can enhance the ability of the plant to tolerate drought. As used herein, the terms "drought resistance" and "drought tolerance" are used to refer to a plants increased resistance or tolerance to stress induced by a reduction in water availability, as compared to normal circumstances, and the ability of the plant to function and survive in lower-water environments, and perform in a relatively superior manner. In this aspect of the invention it is proposed, for example, that the expression of a preselected DNA segment encoding the biosynthesis of osmotically-active solutes can impart protection against drought. Within this class of preselected DNA segments are DNAs encoding mannitol dehydrogenase (Lee and Saier, *J. Bacteriol.*, 153 (1982)) and trehalose-6-phosphate synthase (Kaasen et al., *J. Bacteriol.*, 174, 889 (1992)). Through the subsequent action of native phosphatases in the cell or by the introduction and coexpression of a specific phosphatase, these introduced preselected DNAs will result in the accumulation of either mannitol or trehalose, respectively, both of which have been well documented as protective compounds able to mitigate the effects of stress. Mannitol accumulation in transgenic tobacco has been verified and preliminary results indicate that plants expressing high levels of this metabolite are able to tolerate an applied osmotic stress (Tarczynski et al., cited supra (1992), (1993)).

Similarly, the efficacy of other metabolites in protecting either enzyme function (e.g. alanopine or propionic acid) or membrane integrity (e.g., alanopine) has been documented (Loomis et al., *J. Expt. Zool.*, 252, 9 (1989)), and therefore expression of a preselected DNA segment encoding the biosynthesis of these compounds can confer drought resistance in a manner similar to or complimentary to mannitol. Other examples of naturally occurring metabolites that are osmotically active and/or provide some direct protective effect during drought and/or desiccation include sugars and sugar derivatives such as fructose, erythritol (Coxson et al., *Biotropica*, 24, 121 (1992)), sorbitol, dulcitol (Karsten et al., *Botanica Marina*, 35, 11 (1992)), glucosylglycerol (Reed et al., *J. Gen. Microbiol.*, 130, 1 (1984); Erdmann et al., *J. Gen. Microbiol.*, 138, 363 (1992)), sucrose, stachyose (Koster and Leopold, *Plant Physiol.*, 88, 829 (1988); Blackman et al., *Plant Physiol.*, 100, 225 (1992)), ononitol and pinitol (Vernon and Bohnert, *EMBO J.*, 11, 2077 (1992)), and raffinose (Bernal-Lugo and Leopold, *Plant Physiol.*, 98, 1207 (1992)). Other osmotically active solutes which are not sugars include, but are not limited to, proline (Rensburg et al., 1993) and glycine-betaine (Wyn-Jones and Storey, In: *Physiology and Biochemistry of Drought Resistance in Plants*, Paleg et al. (eds.), pp. 171–204 (1981)). Continued canopy growth and increased reproductive fitness during times of stress can be augmented by introduction and expression of preselected DNA segments such as those controlling the osmotically active compounds discussed above and other such compounds, as represented in one exemplary embodiment by the enzyme myoinositol 0-methyltransferase.

It is contemplated that the expression of specific proteins may also increase drought tolerance. Three classes of Late Embryogenic Proteins have been assigned based on structural similarities (see Dure et al., *Plant Mol. Biol.*, 12, 475 (1989)). All three classes of these proteins have been demonstrated in maturing (i.e., desiccating) seeds. Within these 3 types of proteins, the Type-II (dehydrin-type) have generally been implicated in drought and/or desiccation tolerance in vegetative plant parts (i.e. Mundy and Chua, *EMBO J.*, 7, 2279 (1988); Piatkowski et al., *Plant Physiol.*, 94, 1682 (1990); Yamaguchi-Shinozaki et al., *Plant Cell Physiol.*, 33, 217 (1992)). Recently, expression of a Type-III LEA (HVA-1) in tobacco was found to influence plant height, maturity and drought tolerance (Fitzpatrick, *Gen. Engineering News*, 22, 7 (1993)). Expression of structural genes from all three groups may therefore confer drought tolerance. Other types of proteins induced during water stress include thiol proteases, aldolases and transmembrane transporters (Guerrero et al., *Plant Mol. Biol.*, 15, 11 (1990)), which may confer various protective and/or repair-type functions during drought stress. The expression of a preselected DNA segment that effects lipid biosynthesis and hence membrane composition can also be useful in conferring drought resistance on the plant.

Many genes that improve drought resistance have complementary modes of action. Thus, combinations of these genes might have additive and/or synergistic effects in improving drought resistance in maize. Many of these genes also improve freezing tolerance (or resistance); the physical stresses incurred during freezing and drought are similar in nature and may be mitigated in similar fashion. Benefit may be conferred via constitutive expression of these genes, but the preferred means of expressing these novel genes may be through the use of a turgor-induced promoter (such as the promoters for the turgor-induced genes described in Guerrero et al. (*Plant Molecular Biology*, 15, 11 (1990)) and Shagan et al., *Plant Physiol.*, 101, 1397 (1993), which are incorporated herein by reference). Spatial and temporal expression patterns of these genes may enable maize to better withstand stress.

It is proposed that expression of genes that are involved with specific morphological traits that allow for increased water extractions from drying soil would be of benefit. For example, introduction and expression of genes that alter root characteristics may enhance water uptake. It is also contemplated that expression of DNAs that enhance reproductive fitness during times of stress would be of significant value. For example, expression of DNAs that improve the synchrony of pollen shed and receptiveness of the female flower parts, i.e., silks, would be of benefit. In addition it is proposed that expression of genes that minimize kernel abortion during times of stress would increase the amount of grain to be harvested and hence be of value. It is further contemplated that regulation of cytokinin levels in monocots, such as maize, by introduction and expression of an isopentenyl transferase gene with appropriate regulatory sequences can improve monocot stress resistance and yield (Gan et al., *Science*, 270, 1986 (1995)).

Given the overall role of water in determining yield, it is contemplated that enabling maize to utilize water more efficiently, through the introduction and expression of novel genes, will improve overall performance even when soil water availability is not limiting. By introducing genes that improve the ability of maize to maximize water usage across a full range of stresses relating to water availability, yield stability or consistency of yield performance may be realized.

D. Preparation of an Expression Cassette

An expression cassette of the invention can comprise a recombinant DNA molecule containing a preselected DNA segment operably linked to a promoter functional in a host cell. A preselected DNA segment can be identified and isolated by standard methods, as described by Sambrook et al., *Molecular Cloning: A Laboratory Manual*, Cold Spring Harbor, N.Y. (1989). The preselected DNA segment can also be obtained from water stress-tolerant cell lines. The preselected DNA segment can be identified by screening of a DNA or cDNA library generated from nucleic acid derived from a particular cell type, cell line, primary cells, or tissue. Screening for DNA fragments that encode all or a portion of the preselected DNA segment can be accomplished by screening plaques from a genomic or cDNA library for hybridization to a probe of the DNA from other organisms or by screening plaques from a cDNA expression library for binding to antibodies that specifically recognize the protein encoded by the preselected DNA segment. DNA fragments that hybridize to a preselected DNA segment probe from other organisms and/or plaques carrying DNA fragments that are immunoreactive with antibodies to the protein encoded by the preselected DNA segment can be subcloned into a vector and sequenced and/or used as probes to identify other cDNA or genomic sequences encoding all or a portion of the preselected DNA segment.

Portions of the genomic copy or copies of the preselected DNA segment can be sequenced and the 5' end of the DNA identified by standard methods including either DNA sequence homology to other homologous genes or by RNAase protection analysis, as described by Sambrook et al., *Molecular Cloning: A Laboratory Manual*, Cold Spring Harbor Press, Cold Spring Harbor, N.Y. (1989). Once portions of the 5' end of the preselected DNA segment are identified, complete copies of the preselected DNA segment can be obtained by standard methods, including cloning or polymerase chain reaction (PCR) synthesis using oligonucleotide primers complementary to the preselected DNA segment at the 5' end of the DNA. The presence of an isolated full-length copy of the preselected DNA can be verified by hybridization, partial sequence analysis, or by expression of the preselected DNA segment.

The construction of such expression cassettes which may be employed in conjunction with the present invention will be known to those of skill in the art in light of the present disclosure (see, e.g., Sambrook et al., *Molecular Cloning: A Laboratory Manual*, Cold Spring Harbor, N.Y. (1989); Gelvin et al., *Plant Molecular Biology Manual*, (1990)).

1. Promoters

Once a preselected DNA segment is obtained and amplified, it is operably combined with a promoter to form an expression cassette.

Most genes have regions of DNA sequence that are known as promoters and which regulate gene expression. Promoter regions are typically found in the flanking DNA sequence upstream from the coding sequence in both prokaryotic and eukaryotic cells. A promoter sequence provides for regulation of transcription of the downstream gene sequence and typically includes from about 50 to about 2,000 nucleotide base pairs. Promoter sequences also contain regulatory sequences such as enhancer sequences that can influence the level of gene expression. Some isolated promoter sequences can provide for gene expression of heterologous DNAs, that is a DNA different from the native or homologous DNA. Promoter sequences are also known to be strong or weak or inducible. A strong promoter provides for a high level of gene expression, whereas a weak promoter provides for a very low level of gene expression. An inducible promoter is a promoter that provides for turning on and off of gene expression in response to an exogenously added agent or to an environmental or developmental stimulus. Promoters can also provide for tissue specific or developmental regulation. An isolated promoter sequence that is a strong promoter for heterologous DNAs is advantageous because it provides for a sufficient level of gene expression to allow for easy detection and selection of transformed cells and provides for a high level of gene expression when desired.

The promoter in an expression cassette of the invention can provide for expression of the preselected DNA segment. Preferably, the preselected DNA segment is expressed so as to result in an increase in tolerance of the plant cells to water deficit, or to increase the content of an osmoprotectant in the plant cells. The promoter can also be inducible so that gene expression can be turned on or off by an exogenously added agent. For example, a bacterial promoter such as the $P_{tac}$ promoter can be induced to varying levels of gene expression depending on the level of isothiopropylgalactoside added to the transformed bacterial cells. It may also be preferable to combine the preselected DNA segment with a promoter that provides tissue specific expression or developmentally regulated gene expression in plants.

Preferred constructs will generally include, but are not limited to, a plant promoter such as the CaMV 35S promoter (Odell et al., *Nature*, 313, 810 (1985)), or others such as CaMV 19S (Lawton et al., *Plant Mol. Biol.*, 9, 31F (1987)), nos (Ebert et al., *PNAS USA*, 84, 5745 (1987)), Adh (Walker et al., *PNAS USA*, 84, 6624 (1987)), sucrose synthase (Yang et al., *PNAS USA*, 87, 4144 (1990)), α-tubulin, ubiquitin, actin (Wang et al., *Mol. Cell. Biol.*, 12, 3399 (1992)), cab (Sullivan et al., *Mol. Gen. Genet.*, 215, 431 (1989)), PEP-Case (Hudspeth et al., *Plant Mol. Biol.*, 12, 579 (1989)) or those associated with the R gene complex (Chandler et al., *The Plant Cell*, 1, 1175 (1989)). Other promoters useful in the practice of the invention are known to those of skill in the art, including, but not limited to, water-stress, ABA and turgor-inducible promoters.

A preselected DNA segment can be combined with the promoter by standard methods as described in Sambrook et al., cited supra. Briefly, a plasmid containing a promoter such as the 35S CaMV promoter can be constructed as described in Jefferson, *Plant Molecular Biology Reporter*, 5, 387 (1987) or obtained from Clontech Lab in Palo Alto, Calif. (e.g., pBI121 or pBI221). Typically, these plasmids are constructed to provide for multiple cloning sites having specificity for different restriction enzymes downstream from the promoter. The preselected DNA segment can be subcloned downstream from the promoter using restriction enzymes to ensure that the DNA is inserted in proper orientation with respect to the promoter so that the DNA can be expressed. In a preferred version, a bacterial MIPD gene is operably linked to a 35S CaMV promoter in a plasmid. Once the preselected DNA segment is operably linked to a promoter, the expression cassette so formed can be subcloned into a plasmid or other vectors.

2. Optional Sequences in the Expression Cassette

The expression cassette can also optionally contain other DNA sequences. Transcription enhancers or duplications of enhancers can be used to increase expression from a particular promoter. Examples of such enhancers include, but are not limited to, elements from the CaMV 35S promoter and octopine synthase genes (Last et al., U.S. Pat. No. 5,290,924, issued Mar. 1, 1994). For example, it is contemplated that vectors for use in accordance with the present invention may be constructed to include the ocs enhancer element. This element was first identified as a 16 bp palindromic enhancer from the octopine synthase (ocs) gene of *Agrobacterium* (Ellis et al., *EMBO J.*, 6, 3203 (1987)), and is present in at least 10 other promoters (Bouchez et al., *EMBO J.*, 8, 4197 (1989)). It is proposed that the use of an enhancer element, such as the ocs element and particularly multiple copies of the element, will act to increase the level of transcription from adjacent promoters when applied in the context of monocot transformation. Tissue-specific promoters, including but not limited to, root-cell promoters (Conkling et al., *Plant Physiol.*, 93, 1203 (1990)), and tissue-specific enhancers (Fromm et al., *The Plant Cell*, 1, 977 (1989)) are also contemplated to be particularly useful, as are inducible promoters such as water-stress-, ABA- and turgor-inducible promoters (Guerrero et al., Plant Molecular Biology 15: 11–26), and the like.

Tissue specific expression may be functionally accomplished by introducing a constitutively expressed gene (all tissues) in combination with an antisense gene that is expressed only in those tissues where the gene product is not desired. For example, a preselected DNA segment encoding an enzyme which catalyzes the synthesis of an osmoprotectant, may be introduced so that it is expressed in all tissues using the 35S promoter from Cauliflower Mosaic Virus. Expression of an antisense transcript of this preselected DNA segment in a maize kernel, using, for example, a zein promoter, would prevent accumulation of the gene product in seed. Hence the protein encoded by the preselected DNA would be present in all tissues except the kernel.

Alternatively, one may wish to obtain novel tissue-specific promoter sequences for use in accordance with the present invention. To achieve this, one may first isolate cDNA clones from the tissue concerned and identify those clones which are expressed specifically in that tissue, for example, using Northern blotting. Ideally, one would like to identify a gene that is not present in a high copy number, but which gene product is relatively abundant in specific tissues. The promoter and control elements of corresponding genomic clones may then be localized using the techniques of molecular biology known to those of skill in the art.

Expression of some genes in transgenic plants will occur only under specified conditions. For example, it is an object of the present invention that expression of preselected DNA segment that confer resistance to environmental stress factors such as drought will occur only under actual stress conditions. Expression of such genes throughout a plants development may have detrimental effects. It is known that a large number of genes exist that respond to the environment. For example, expression of some genes such as rbcS, encoding the small subunit of ribulose bisphosphate carboxylase, is regulated by light as mediated through phytochrome. Other genes are induced by secondary stimuli. For example, synthesis of abscisic acid (ABA) is induced by certain environmental factors, including, but not limited to, water stress. A number of genes have been shown to be induced by ABA (Skriver et al., *Plant Cell*, 2, 503 (1990)). Therefore, inducible expression of a preselected DNA segment in transgenic plants can occur.

In some embodiments of the present invention expression of a preselected DNA segment in a transgenic plant will occur only in a certain time period during the development of the plant. Developmental timing is frequently correlated with tissue specific gene expression. For example, expression of zein storage proteins is initiated in the endosperm about 15 days after pollination.

As the DNA sequence inserted between the transcription initiation site and the start of the coding sequence, i.e., the untranslated leader sequence, can influence gene expression, one can also employ a particular leader sequence. Preferred leader sequence include those which comprise sequences selected to direct optimum expression of the attached gene, i.e., to include a preferred consensus leader sequence which can increase or maintain mRNA stability and prevent inappropriate initiation of translation (Joshi, *Nucl. Acid Res.*, 15, 6643 (1987)). Such sequences are known to those of skill in the art. Sequences that are derived from genes that are highly expressed in plants, and in maize in particular, will be most preferred.

Regulatory elements such as Adh intron 1 (Callis et al., *Genes Develop.*, 1, 1183 (1987)), sucrose synthase intron (Vasil et al., *Plant Physiol.*, 91, 5175 (1989)) or TMV omega element (Gallie et al., *The Plant Cell*, 1, 301 (1989)) can also be included where desired. Other such regulatory elements useful in the practice of the invention are known to those of skill in the art.

Additionally, expression cassettes can be constructed and employed to target the gene product of the preselected DNA segment to an intracellular compartment within plant cells or to direct a protein to the extracellular environment. This can generally be achieved by joining a DNA sequence encoding a transit or signal peptide sequence to the coding sequence of the preselected DNA segment. The resultant transit, or signal, peptide will transport the protein to a particular intracellular, or extracellular destination, respectively, and can then be post-translationally removed. Transit or signal peptides act by facilitating the transport of proteins through intracellular membranes, e.g., vacuole, vesicle, plastid and mitochondrial membranes, whereas signal peptides direct proteins through the extracellular membrane. By facilitating transport of the protein into compartments inside or outside the cell, these sequences can increase the accumulation of gene product.

The preselected DNA segment can be directed to a particular organelle, such as the chloroplast rather than to the cytoplasm. Thus, the expression cassette can further be comprised of a chloroplast transit peptide encoding DNA sequence operably linked between a promoter and the preselected DNA segment (for a review of plastid targeting peptides, see Heijne et al., *Eur. J. Biochem.*, 180, 535 (1989); Keegstra et al., *Ann. Rev. Plant Physiol. Plant Mol. Biol.*, 40, 471 (1989)). This is exemplified by the use of the rbcS (RuBISCO) transit peptide which targets proteins specifically to plastids.

An exogenous chloroplast transit peptide can be used. A chloroplast transit peptide is typically 40 to 70 amino acids in length and functions post-translationally to direct a protein to the chloroplast. The transit peptide is cleaved either during or just after import into the chloroplast to yield the mature protein. The complete copy of the preselected DNA segment may contain a chloroplast transit peptide sequence. In that case, it may not be necessary to combine an exogenously obtained chloroplast transit peptide sequence into the expression cassette.

Exogenous chloroplast transit peptide encoding sequences can be obtained from a variety of plant nuclear genes, so long as the products of the genes are expressed as preproteins comprising an amino terminal transit peptide and transported into chloroplast. Examples of plant gene products known to include such transit peptide sequences include, but are not limited to, the small subunit of ribulose biphosphate carboxylase, ferredoxin, chlorophyll a/b binding protein, chloroplast ribosomal proteins encoded by nuclear genes, certain heatshock proteins, amino acid biosynthetic enzymes such as acetolactate acid synthase, 3-enolpyruvylphosphoshikimate synthase, dihydrodipicolinate synthase, and the like. Alternatively, the DNA fragment coding for the transit peptide may be chemically synthesized either wholly or in part from the known sequences of transit peptides such as those listed above.

Regardless of the source of the DNA fragment coding for the transit peptide, it should include a translation initiation codon and an amino acid sequence that is recognized by and will function properly in chloroplasts of the host plant. Attention should also be given to the amino acid sequence at the junction between the transit peptide and the protein encoded by the preselected DNA segment where it is cleaved to yield the mature enzyme. Certain conserved amino acid sequences have been identified and may serve as a guideline. Precise fusion of the transit peptide coding sequence with the preselected DNA segment coding sequence may require manipulation of one or both DNA sequences to introduce, for example, a convenient restriction site. This may be accomplished by methods including site-directed mutagenesis, insertion of chemically synthesized oligonucleotide linkers, and the like.

Once obtained, the chloroplast transit peptide sequence can be appropriately linked to the promoter and the preselected DNA segment in an expression cassette using standard methods. Briefly, a plasmid containing a promoter functional in plant cells and having multiple cloning sites downstream can be constructed as described in Jefferson, cited supra. The chloroplast transit peptide sequence can be inserted downstream from the promoter using restriction enzymes. The preselected DNA segment can then be inserted immediately downstream from and in frame with the 3' terminus of the chloroplast transit peptide sequence so that the chloroplast transit peptide is linked to the amino terminus of the protein encoded by the preselected DNA segment. Once formed, the expression cassette can be subcloned into other plasmids or vectors.

Targeting of the gene product to an intracellular compartment within plant cells may also be achieved by direct delivery of a preselected DNA segment to the intracellular compartment. For example, an expression cassette encoding a protein, the presence of which is desired in the chloroplast, may be directly introduced into the chloroplast genome using the method described in Maliga et al., U.S. Pat. No. 5,451,513, issued Sep. 19, 1995, incorporated herein by reference.

It may be useful to target DNA itself within a cell. For example, it may be useful to target an introduced preselected DNA to the nucleus as this may increase the frequency of transformation. Within the nucleus itself, it would be useful to target a gene in order to achieve site-specific integration. For example, it would be useful to have a gene introduced through transformation replace an existing gene in the cell.

When the expression cassette is to be introduced into a plant cell, the expression cassette can also optionally include 3' nontranslated plant regulatory DNA sequences that act as a signal to terminate transcription and allow for the polyadenylation of the resultant mRNA. The 3' nontranslated regulatory DNA sequence preferably includes from about 300 to 1,000 nucleotide base pairs and contains plant transcriptional and translational termination sequences.

Preferred 3' elements are derived from those from the nopaline synthase gene of *Agrobacterium tumefaciens* (Bevan et al., *Nucl. Acid Res.*, 11, 369 (1983)), the terminator for the T7 transcript from the octopine synthase gene of *Agrobacterium tumefaciens*, and the 3' end of the protease inhibitor I or II genes from potato or tomato, although other 3' elements known to those of skill in the art can also be employed. These 3' nontranslated regulatory sequences can be obtained as described in An, *Methods in Enzymology*, 153, 292 (1987) or are already present in plasmids available from commercial sources such as Clontech, Palo Alto, Calif. The 3' nontranslated regulatory sequences can be operably linked to the 3' terminus of the preselected DNA segment by standard methods.

An expression cassette of the invention can also be further comprise plasmid DNA. Plasmid vectors include additional DNA sequences that provide for easy selection, amplification, and transformation of the expression cassette in prokaryotic and eukaryotic cells, e.g., pUC-derived vectors such as pUC8, pUC9, pUC 18, pUC 19, pUC23, pUC 119, and pUC 120, pSK-derived vectors, pGEM-derived vectors, pSP-derived vectors, or pBS-derived vectors. The additional DNA sequences include origins of replication to provide for autonomous replication of the vector, selectable marker genes, preferably encoding antibiotic or herbicide resistance, unique multiple cloning sites providing for multiple sites to insert DNA sequences or genes encoded in the expression cassette, and sequences that enhance transformation of prokaryotic and eukaryotic cells.

Another vector that is useful for expression in both plant and prokaryotic cells is the binary Ti plasmid (as disclosed in Schilperoort et al., U.S. Pat. No. 4,940,838, issued Jul. 10, 1990) as exemplified by vector pGA582. This binary Ti plasmid vector has been previously characterized by An, cited supra, and is available from Dr. An. This binary Ti vector can be replicated in prokaryotic bacteria such as *E. coli* and *Agrobacterium*. The *Agrobacterium* plasmid vectors can be used to transfer the expression cassette to plant cells. The binary Ti vectors preferably include the nopaline T DNA right and left borders to provide for efficient plant cell transformation, a selectable marker gene, unique multiple cloning sites in the T border regions, the colE1 replication of origin and a wide host range replicon. The binary Ti vectors carrying an expression cassette of the invention can be used to transform both prokaryotic and eukaryotic cells, but is preferably used to transform plant cells.

III. DNA Delivery

Following the generation of recipient cells, the present invention generally next includes steps directed to introducing a preselected DNA segment or segment, such as a preselected cDNA, into a recipient cell to create a transformed cell. The frequency of occurrence of cells receiving DNA is believed to be low. Moreover, it is most likely that not all recipient cells receiving DNA segments or sequences will result in a transformed cell wherein the DNA is stably integrated into the plant genome and/or expressed. Some may show only initial and transient gene expression. However, certain cells from virtually any monocot species may be stably transformed, and these cells developed into transgenic plants, through the application of the techniques disclosed herein.

An expression cassette of the invention can be introduced by methods of transformation especially effective for monocots, including, but not limited to, microprojectile bombardment of immature embryos (U.S. patent application Ser. No. 08/249,458, filed May 26, 1994, incorporated by reference herein; U.S. patent application Ser. No. 08/112,245, filed Aug. 25, 1993, incorporated by reference herein) or Type II embryogenic callus cells as described by W. J. Gordon-Kamm et al. (*Plant Cell*, 2, 603 (1990)), M. E. Fromm et al. (*Bio/Technology*, 8, 833 (1990)) and D. A. Walters et al. (*Plant Molecular Biology*, 18, 189 (1992)), or by electroporation of type I embryogenic calluses described by D'Halluin et al. (*The Plant Cell*, 4, 1495 (1992)), or by Krzyzek et al. (U.S. Pat. No. 5,384,253, issued Jan. 24, 1995).

A. Electroporation

Where one wishes to introduce DNA by means of electroporation, it is contemplated that the method of Krzyzek et al. (U.S. Pat. No. 5,384,253, issued Jan. 24, 1995, incorporated herein by reference) will be particularly advantageous. In this method, certain cell wall-degrading enzymes, such as pectin-degrading enzymes, are employed to render the target recipient cells more susceptible to transformation by electroporation than untreated cells. Alternatively, recipient cells are made more susceptible to transformation, by mechanical wounding.

To effect transformation by electroporation one may employ either friable tissues such as a suspension culture of cells, or embryogenic callus, or alternatively, one may transform immature embryos or other organized tissues directly. One would partially degrade the cell walls of the chosen cells by exposing them to pectin-degrading enzymes (pectolyases) or mechanically wounding in a controlled manner. Such cells would then be recipient to DNA transfer by electroporation, which may be carried out at this stage, and transformed cells then identified by a suitable selection or screening protocol dependent on the nature of the newly incorporated DNA.

B. Microprojectile Bombardment

A further advantageous method for delivering transforming DNA segments to plant cells is microprojectile bombardment. In this method, particles may be coated with nucleic acids and delivered into cells by a propelling force. Exemplary particles include those comprised of tungsten, gold, platinum, and the like.

It is contemplated that in some instances DNA precipitation onto metal particles would not be necessary for DNA delivery to a recipient cell using microprojectile bombardment. In an illustrative embodiment, non-embryogenic BMS cells were bombarded with intact cells of the bacteria *E. coli* or *Agrobacterium tumefaciens* containing plasmids with either the β-glucoronidase or bar gene engineered for expression in maize. Bacteria were inactivated by ethanol dehydration prior to bombardment. A low level of transient expression of the β-glucoronidase gene was observed 24–48 hours following DNA delivery. In addition, stable transformants containing the bar gene were recovered following bombardment with either *E. Coli* or *Agrobacterium tumefaciens* cells. It is contemplated that particles may contain DNA rather than be coated with DNA. Hence it is proposed that DNA-coated particles may increase the level of DNA delivery via particle bombardment but are not, in and of themselves, necessary.

An advantage of microprojectile bombardment, in addition to it being an effective means of reproducibly stably transforming monocots, is that neither the isolation of protoplasts (Cristou et al., *Plant Physiol.*, 87, 671 (1988)) nor the susceptibility to *Agrobacterium* infection is required. An illustrative embodiment of a method for delivering DNA into maize cells by acceleration is a Biolistics Particle Delivery System, which can be used to propel particles coated with DNA or cells through a screen, such as a stainless steel or Nytex screen, onto a filter surface covered with maize cells cultured in suspension (Gordon-Kamm et al., *The Plant Cell*, 2, 603 (1990)). The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing damage inflicted on the recipient cells by projectiles that are too large.

For the bombardment, cells in suspension are preferably concentrated on filters or solid culture medium. Alternatively, immature embryos or other target cells may be arranged on solid culture medium. The cells to be bombarded are positioned at an appropriate distance below the macroprojectile stopping plate. If desired, one or more screens are also positioned between the acceleration device and the cells to be bombarded. Through the use of techniques set forth herein one may obtain up to 1000 or more foci of cells transiently expressing a marker gene. The number of cells in a focus which express the exogenous gene product 48 hours post-bombardment often range from about 1 to 10 and average about 1 to 3.

In bombardment transformation, one may optimize the prebombardment culturing conditions and the bombardment parameters to yield the maximum numbers of stable transformants. Both the physical and biological parameters for bombardment are important in this technology. Physical factors are those that involve manipulating the DNA/microprojectile precipitate or those that affect the flight and velocity of either the macro- or microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmids. It is believed that pre-bombardment manipulations are especially important for successful transformation of immature embryos.

Accordingly, it is contemplated that one may wish to adjust various of the bombardment parameters in small scale studies to fully optimize the conditions. One may particularly wish to adjust physical parameters such as gap distance, flight distance, tissue distance, and helium pressure. One may also minimize the trauma reduction factors (TRFs) by modifying conditions which influence the physiological state of the recipient cells and which may therefore influence transformation and integration efficiencies. For example, the osmotic state, tissue hydration and the subculture stage or cell cycle of the recipient cells may be adjusted for optimum transformation. Results from such small scale optimization studies are disclosed herein and the execution of other routine adjustments will be known to those of skill in the art in light of the present disclosure.

IV. Production and Characterization of Stable Transgenic Maize

After effecting delivery of a preselected DNA segment to recipient cells by any of the methods discussed above, the next steps of the invention generally concern identifying the transformed cells for further culturing and plant regeneration. As mentioned above, in order to improve the ability to identify transformants, one may desire to employ a selectable or screenable marker gene as, or in addition to, the expressible preselected DNA segment. In this case, one would then generally assay the potentially transformed cell population by exposing the cells to a selective agent or agents, or one would screen the cells for the desired marker gene trait.

A. Selection

An exemplary embodiment of methods for identifying transformed cells involves exposing the bombarded cultures to a selective agent, such as a metabolic inhibitor, an antibiotic, herbicide or the like. Cells which have been transformed and have stably integrated a marker gene conferring resistance to the selective agent used, will grow and divide in culture. Sensitive cells will not be amenable to further culturing.

To use the bar-bialaphos or the EPSPS-glyphosate selective system, bombarded tissue is cultured for about 0–28 days on nonselective medium and subsequently transferred to medium containing from about 1–3 mg/l bialaphos or about 1–3 mM glyphosate, as appropriate. While ranges of about 1–3 mg/l bialaphos or about 1–3 mM glyphosate will typically be preferred, it is proposed that ranges of at least about 0.1–50 mg/l bialaphos or at least about 0.1–50 mM glyphosate will find utility in the practice of the invention. Tissue can be placed on any porous, inert, solid or semi-solid support for bombardment, including but not limited to filters and solid culture medium. Bialaphos and glyphosate are provided as examples of agents suitable for selection of transformants, but the technique of this invention is not limited to them.

An example of a screenable marker trait is the red pigment produced under the control of the R-locus in maize. This pigment may be detected by culturing cells on a solid support containing nutrient media capable of supporting growth at this stage and selecting cells from colonies (visible aggregates of cells) that are pigmented. These cells may be cultured further, either in suspension or on solid media. The R-locus is useful for selection of transformants from bombarded immature embryos. In a similar fashion, the introduction of the C1 and B genes will result in pigmented cells and/or tissues.

The enzyme luciferase is also useful as a screenable marker in the context of the present invention. In the presence of the substrate luciferin, cells expressing luciferase emit light which can be detected on photographic or x-ray film, in a luminometer (or liquid scintillation counter), by devices that enhance night vision, or by a highly light sensitive video camera, such as a photon counting camera. All of these assays are nondestructive and transformed cells may be cultured further following identification. The photon counting camera is especially valuable as it allows one to identify specific cells or groups of cells which are expressing luciferase and manipulate those in real time.

It is further contemplated that combinations of screenable and selectable markers will be useful for identification of transformed cells. In some cell or tissue types a selection agent, such as bialaphos or glyphosate, may either not provide enough killing activity to clearly recognize transformed cells or may cause substantial nonselective inhibition of transformants and nontransformants alike, thus causing the selection technique to not be effective. It is proposed that selection with a growth inhibiting compound, such as bialaphos or glyphosate at concentrations below those that cause 100% inhibition followed by screening of growing tissue for expression of a screenable marker gene such as luciferase would allow one to recover transformants from cell or tissue types that are not amenable to selection alone. In an illustrative embodiment embryogenic type II callus of *Zea mays* L. was selected with sub-lethal levels of bialaphos. Slowly growing tissue was subsequently screened for expression of the luciferase gene and transformants were identified. In this example, neither selection nor screening conditions employed were sufficient in and of themselves to identify transformants. Therefore it is proposed that combinations of selection and screening will enable one to identify transformants in a wider variety of cell and tissue types.

B. Regeneration and Seed Production

Cells that survive the exposure to the selective agent, or cells that have been scored positive in a screening assay, may be cultured in media that supports regeneration of plants. In an exemplary embodiment, MS and N6 media have been modified (see Table 1) by including further substances such as growth regulators. A preferred growth regulator for such purposes is dicamba or 2,4-D. However, other growth regulators may be employed, including NAA, NAA+2,4-D or perhaps even picloram. Media improvement in these and like ways was found to facilitate the growth of cells at specific developmental stages. Tissue is preferably maintained on a basic media with growth regulators until sufficient tissue is available to begin plant regeneration efforts, or following repeated rounds of manual selection, until the morphology of the tissue is suitable for regeneration, at least two weeks, then transferred to media conducive to maturation of embryoids. Cultures are transferred every two weeks on this medium. Shoot development will signal the time to transfer to medium lacking growth regulators.

The transformed cells, identified by selection or screening and cultured in an appropriate medium that supports regeneration, will then be allowed to mature into plants. Developing plantlets are transferred to soilless plant growth mix, and hardened, e.g., in an environmentally controlled chamber at about 85% relative humidity, about 600 ppm $CO_2$, and at about 25–250 microeinsteins $m^{-2} -s^{-1}$ of light. Plants are preferably matured either in a growth chamber or greenhouse. Plants are regenerated from about 6 weeks to 10 months after a transformant is identified, depending on the initial tissue. During regeneration, cells are grown on solid media in tissue culture vessels. Illustrative embodiments of such vessels are petri dishes and Plant Con®s. Regenerating plants are preferably grown at about 19° to 28° C. After the regenerating plants have reached the stage of shoot and root development, they may be transferred to a greenhouse for further growth and testing.

Mature plants are then obtained from cell lines that are known to express the trait. If possible, the regenerated plants are self pollinated. In addition, pollen obtained from the regenerated plants is crossed to seed grown plants of agronomically important inbred lines. In some cases, pollen from plants of these inbred lines is used to pollinate regenerated plants. The trait is genetically characterized by evaluating the segregation of the trait in first and later generation progeny. The heritability and expression in plants of traits selected in tissue culture are of particular importance if the traits are to be commercially useful.

Regenerated plants can be repeatedly crossed to inbred maize plants in order to introgress the preselected DNA segment into the genome of the inbred maize plants. This process is referred to as backcross conversion. When a sufficient number of crosses to the recurrent inbred parent have been completed in order to produce a product of the backcross conversion process that is substantially isogenic with the recurrent inbred parent except for the presence of the introduced preselected DNA segment, the plant is self-pollinated at least once in order to produce a homozygous backcross converted inbred containing the preselected DNA segment. Progeny of these plants are true breeding and the level of an osmoprotectant, or the degree of resistance or tolerance to a reduction in water availability, in these progeny are compared to the level of the osmoprotectant, or the degree of resistance or tolerance to a reduction in water availability, in the recurrent parent inbred, in the field under a range of environmental conditions (see below). The determination of the level of tolerance or resistance to a reduction in water availability are well known in the art.

Alternatively, seed from transformed monocot plants regenerated from transformed tissue cultures is grown in the field and self-pollinated to generate true breeding plants. Progenies from these plants become true breeding lines which are evaluated for resistance or tolerance to reduced water availability, or production of an osmoprotectant, in the field under a range of environmental conditions.

Progeny and subsequent generations are grown in the field and assayed for their performance under a range of water availability conditions. Both qualitative and quantitative measures of the plant's ability to withstand water stress are made. Seeds are germinated in the greenhouses, growth chambers and field conditions under ample water supply. At one or more times during the plant's life cycle, water availability is reduced in order to identify plants that exhibit tolerance or resistance to a reduction in water availability. In addition to the visual signs of wilting, which may only be observed under more pronounced drought stress, measures of plant water status are made. These measures include, but are not limited to, total water potential, osmotic potential and turgor potential are quantitatively measured and detection of differences in turgor or the ability of the plants not to wilt. These measurements can be made even when no signs of plant stress are visible to the eye. Plants expressing the most favorable water status result in superior growth under water stress. Different measures of growth are used to document this superior performance including, but not limited to, measures of cell and leaf area expansion.

The physiological and biochemical activity of the transformed plant tissue is indicative of its improved stress tolerance. Such screening of plants with the measurement of photosynthetic activity or transpirational activity are only two examples of the types of measurement that can be done to identify the superiority of the transgenic plants compared to non-transformed plants. Measurements of reproductive capacity including, but not limited to, the synchrony of pollen shed and silk emergence are indicators of improved stress tolerance when the preselected DNA segment is expressed. It is contemplated that barrenness will not be a problem.

Once the initial breeding lines are selected by criteria, which may include the criteria described above, test crosses are made and hybrid seed is produced. The testcross hybrids and breeding populations are planted in several different arrays in the field. One scheme of evaluation is to grow populations of hybrid plants containing the preselected DNA segment in many different locations and measure the performance of the plants at these different locations. Given the variability of rainfall distribution, the different locations receive different quantities of rainfall and in some locations, the plants will receive stress. Yield information as well as measures which quantify plant response to stress as described earlier, are made. The information regarding the performance of these hybrids along with that of the performance of non-transformed hybrids is compared. It is anticipated that the hybrids expressing the preselected DNA segment will be higher in yield performance and stability at a given level of water availability than the controls.

Where irrigation is available, more controlled comparisons are made through the establishment of differential irrigation treatments. The same entries of hybrids or lines are grown under contrasting irrigation treatments. Such an approach limits the number of variables at work in the evaluation. Aside from the same types of measurements as defined above, differential responses are calculated because of the contrast in the data. It is anticipated that preselected DNA segment expressing hybrids will have less yield reduction when grown under irrigated versus non-irrigated conditions when compared to hybrids without the gene.

Upon the identification of the superior performance of transgenic plants, the parent selections are advanced and inbred lines are produced through conventional breeding techniques. Hybrid plants having one or more parents containing the preselected DNA segment are tested in commercial testing and evaluation programs and performance documented. This testing includes performance trials over a wide geographical area as well as dedicated trials where water availability is varied to reveal performance advantage and hence value.

An additional advantage of the expression of the preselected DNA segment is the superior performance of the parental inbred lines in production of hybrids. Less stress related parent yield loss is associated with higher green seed yield and thereby higher economic margins.

It is anticipated that the performance advantage will not only be present under stress conditions. Given the overall role of water in determining yield, it is contemplated that maize plants expressing the preselected DNA segment may utilize water more efficiently. This will improve overall performance even when soil water availability is not limiting. Through the introduction of the preselected DNA segment(s) and the improved ability of maize to maximize water usage across a full range of conditions relating to water availability (i.e., including normal and stressed conditions), yield stability or consistency of yield performance will be achieved. These studies are conducted in maize and other monocots.

C. Characterization

To confirm the presence of the preselected DNA segment (s) or "transgene(s)" in the regenerating plants, a variety of assays may be performed. Such assays include, for example, "molecular biological" assays well known to those of skill in the art, such as Southern and Northern blotting and PCR; "biochemical" assays, such as detecting the presence of a protein product, e.g., by immunological means (ELISAs and Western blots) or by enzymatic function; plant part assays, such as leaf or root assays; and also, by analyzing the phenotype of the whole regenerated plant.

1. DNA Integration, RNA Expression and Inheritance

Genomic DNA may be isolated from callus cell lines or any plant parts to determine the presence of the preselected DNA segment through the use of techniques well known to those skilled in the art. Note that intact sequences will not always be present, presumably due to rearrangement or deletion of sequences in the cell.

The presence of DNA elements introduced through the methods of this invention may be determined by polymerase chain reaction (PCR). Using this technique discreet fragments of DNA are amplified and detected by gel electrophoresis. This type of analysis permits one to determine whether a preselected DNA segment is present in a stable transformant, but does not prove integration of the introduced preselected DNA segment into the host cell genome. In addition, it is not possible using PCR techniques to determine whether transformants have exogenous genes introduced into different sites in the genome, i.e., whether transformants are of independent origin. It is contemplated that using PCR techniques it would be possible to clone fragments of the host genomic DNA adjacent to an introduced preselected DNA segment.

Positive proof of DNA integration into the host genome and the independent identities of transformants may be determined using the technique of Southern hybridization. Using this technique specific DNA sequences that were introduced into the host genome and flanking host DNA sequences can be identified. Hence the Southern hybridization pattern of a given transformant serves as an identifying characteristic of that transformant. In addition it is possible through Southern hybridization to demonstrate the presence of introduced preselected DNA segments in high molecular weight DNA, i.e., confirm that the introduced preselected DNA segment has been integrated into the host cell genome. The technique of Southern hybridization provides information that is obtained using PCR, e.g., the presence of a preselected DNA segment, but also demonstrates integration into the genome and characterizes each individual transformant.

It is contemplated that using the techniques of dot or slot blot hybridization which are modifications of Southern hybridization techniques one could obtain the same information that is derived from PCR, e.g., the presence of a preselected DNA segment.

Both PCR and Southern hybridization techniques can be used to demonstrate transmission of a preselected DNA segment to progeny. In most instances the characteristic Southern hybridization pattern for a given transformant will segregate in progeny as one or more Mendelian genes (Spencer et al., *Plant Mol. Biol.*, 18, 201 (1992); Laursen et al., *Plant Mo. Biol.*, 24, 51 (1994)) indicating stable inheritance of the gene. For example, in one study, of 28 progeny ($R_1$) plants tested, 50% (N=14) contained bar, confirming transmission through the germline of the marker gene. The nonchimeric nature of the callus and the parental transformants ($R_0$) was suggested by germline transmission and the identical Southern blot hybridization patterns and intensities of the transforming DNA in callus, $R_0$ plants and $R_1$ progeny that segregated for the transformed gene.

Whereas DNA analysis techniques may be conducted using DNA isolated from any part of a plant, RNA may only be expressed in particular cells or tissue types and hence it will be necessary to prepare RNA for analysis from these tissues. PCR techniques may also be used for detection and quantitation of RNA produced from introduced preselected DNA segments. In this application of PCR it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by Northern blotting. This technique will demonstrate the presence of an RNA species and give information about the integrity of that RNA. The presence or absence of an RNA species can also be determined using dot or slot blot Northern hybridizations. These techniques are modifications of Northern blotting and will only demonstrate the presence or absence of an RNA species.

2. Gene Expression

While Southern blotting and PCR may be used to detect the preselected DNA segment in question, they do not provide information as to whether the preselected DNA segment is being expressed. Expression may be evaluated by specifically identifying the protein products of the introduced preselected DNA segments or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focussing, or by chromatographic techniques such as ion exchange or gel exclusion chromatography. The unique structures of individual proteins offer opportunities for use of specific antibodies to detect their presence in formats such as an ELISA assay. Combinations of approaches may be employed with even greater specificity such as western blotting in which antibodies are used to locate individual gene products that have been separated by electrophoretic techniques. Additional techniques may be employed to absolutely confirm the identity of the product of interest such as evaluation by amino acid sequencing following purification. Although these are among the most commonly employed, other procedures may be additionally used.

Assay procedures may also be used to identify the expression of proteins by their functionality, especially the ability of enzymes to catalyze specific chemical reactions involving specific substrates and products. These reactions may be followed by providing and quantifying the loss of substrates or the generation of products of the reactions by physical or chemical procedures. Examples are as varied as the enzyme to be analyzed and may include assays for PAT enzymatic activity by following production of radiolabelled acetylated phosphinothricin from phosphinothricin and $^{14}$C-acetyl CoA or for anthranilate synthase activity by following loss of fluorescence of anthranilate, to name two.

Very frequently the expression of a gene product is determined by evaluating the phenotypic results of its expression. These assays also may take many forms including but not limited to analyzing changes in the chemical composition, morphology, or physiological properties of the plant. Chemical composition may be altered by expression of preselected DNA segments encoding enzymes or storage proteins which change amino acid composition and may be detected by amino acid analysis, or by enzymes which change starch quantity which may be analyzed by near infrared reflectance spectrometry. Morphological changes may include greater stature or thicker stalks. Most often changes in response of plants or plant parts to imposed treatments are evaluated under carefully controlled conditions termed bioassays.

D. Establishment of the Introduced DNA in Other Maize Varieties

Fertile, transgenic plants may then be used in a conventional maize breeding program in order to incorporate the preselected DNA segment into the desired lines or varieties. Methods and references for convergent improvement of maize are given by Hallauer et al. (In: *Corn and Corn Improvement*, Sprague et al. (eds.), pp. 463–564 (1988)), incorporated herein by reference. Among the approaches that conventional breeding programs employ is a conversion process (backcrossing). Briefly, conversion is performed by crossing the initial transgenic fertile plant to elite inbred lines. The progeny from this cross will segregate such that some of the plants will carry the preselected DNA segment whereas some will not. The plants that do carry the preselected DNA segment are then crossed again to the elite inbred lines resulting in progeny which segregate once more. This backcrossing process is repeated until the original elite inbred has been converted to a line containing the preselected DNA segment, yet possessing all important attributed originally found in the parent. Generally, this will require about 6–8 generations. A separate backcrossing program will be generally used for every elite line that is to be converted to a genetically engineered elite line.

Generally, the commercial value of the transformed maize produced herein will be greatest if the preselected DNA segment can be incorporated into many different hybrid combinations. A farmer typically grows several hybrids based on differences in maturity, standability, and other agronomic traits. Also, the farmer must select a hybrid based upon his or her geographic location since hybrids adapted to one region are generally not adapted to another because of differences in such traits as maturity, disease, drought and insect resistance. As such, it is necessary to incorporate the gene into a large number of parental lines so that many hybrid combinations can be produced containing the preselected DNA segment.

Maize breeding and the techniques and skills required to transfer genes from one line or variety to another are well known to those skilled in the art. Thus, introducing a preselected DNA segment, preferably in the form of recombinant DNA, into any other line or variety can be accomplished by these breeding procedures.

E. Uses of Transgenic Plants

The transgenic plants produced herein are expected to be useful for a variety of commercial and research purposes. Transgenic plants can be created for use in traditional agriculture to possess traits beneficial to the grower (e.g., agronomic traits such as resistance to water deficit, pest resistance, herbicide resistance or increased yield), beneficial to the consumer of the grain harvested from the plant (e.g., improved nutritive content in human food or animal feed), or beneficial to the food processor (e.g., improved processing traits). In such uses, the plants are generally grown for the use of their grain in human or animal foods. However, other parts of the plants, including stalks, husks, vegetative parts, and the like, may also have utility, including use as part of animal silage or for ornamental purposes. Often, chemical constituents (e.g., oils or starches) of maize and other crops are extracted for foods or industrial use and transgenic plants may be created which have enhanced or modified levels of such components.

Transgenic plants may also find use in the commercial manufacture of proteins or other molecules, where the molecule of interest is extracted or purified from plant parts, seeds, and the like. Cells or tissue from the plants may also be cultured, grown in vitro, or fermented to manufacture such molecules.

The transgenic plants may also be used in commercial breeding programs, or may be crossed or bred to plants of related crop species. Improvements encoded by the preselected DNA segment may be transferred, e.g., from maize cells to cells of other species, e.g., by protoplast fusion.

The transgenic plants may have many uses in research or breeding, including creation of new mutant plants through insertional mutagenesis, in order to identify beneficial mutants that might later be created by traditional mutation and selection. An example would be the introduction of a recombinant DNA sequence encoding a transposable element that may be used for generating genetic variation. The methods of the invention may also be used to create plants having unique "signature sequences" or other marker sequences which can be used to identify proprietary lines or varieties.

Success in producing fertile transgenic monocot plants (maize) has now been achieved where others have failed by methods described herein. Aspects of the methods of the present invention for producing the fertile, transgenic maize plants comprise, but are not limited to, isolation of recipient cells using media conducive to specific growth patterns, choice of selective systems that permit efficient detection of transformation; modifications of DNA delivery methods to introduce genetic vectors with exogenous or recombinant DNA into cells; invention of methods to regenerate plants from transformed cells at a high frequency; and the production of fertile transgenic plants capable of surviving and reproducing.

F. Preferred Methods of Delivering DNA to Cells

Preferred DNA delivery systems do not require protoplast isolation or use of *Agrobacterium* DNA. There are several potential cellular targets for DNA delivery to produce fertile transgenic plants: pollen, microspores, meristems, immature embryos and cultured embryogenic cells are but a few examples.

One of the newly emerging techniques for the introduction of preselected DNA segments into plant cells involves the use of microprojectile bombardment. The details of this technique and its use to introduce preselected DNA segment into various plant cells are discussed in Klein et al. (*Plant Physiol.*, 91, 440 (1989)), Wang et al. (*Plant Mol. Biol.*, 11, 433 (1988)) and Christou et al. (*Plant Physiol.*, 87, 671 (1988)). One method of determining the efficiency of DNA delivery into the cells via microprojectile bombardment employs detection of transient expression of the enzyme β-glucuronidase (GUS) in bombarded cells. For this method, plant cells are bombarded with a DNA construct which directs the synthesis of the GUS enzyme.

Apparati are available which perform microprojectile bombardment. A commercially available source is an apparatus made by Biolistics, Inc. (now DuPont), but other microprojectile or acceleration methods are within the scope of this invention. Of course, other "gene guns" may be used to introduce DNA into cells.

Several modifications of the microprojectile bombardment method were made. For example, stainless steel mesh screens were introduced below the stop plate of the bombardment apparatus, i.e., between the gun and the cells. Furthermore, modifications to existing techniques were developed for precipitating DNA onto the microprojectiles.

Another newly emerging technique for the introduction of preselected DNA segment into plant cells is electroporation of intact cells. The details of this technique are described in Krzyzek et al. (U.S. Pat. No. 5,324,253, issued Jan. 24, 1995). Similar to particle bombardment, the efficiency of DNA delivery into cells by electroporation can be determined by using the β-glucuronidase gene. The method of electroporation of intact cells and by extension intact tissues, e.g., immature embryos, were developed by Krzyzek et al., and represent improvements over published procedures. Generation of fertile plants using these techniques were described by Spencer et al. (cited supra (1993)) and Laursen et al. (cited supra (1994)).

Other methods may also be used for introduction of DNA into plants cells, e.g., agitation of cells with DNA and silicon carbide fibers.

Histological analysis of stressed and unstressed tissue from transformed and untransformed plants are performed (Sylvester et al., *Light Microscopy I: Dissection and Microtechnique*, In: The Maize Handbook, pp. 83–95, Springer-Verlag, N.Y. (1994)). Cross sections through the appropriate tissues (e.g. leaves or roots) reveal any structural aberrations. Transmission and scanning electron microscopy are used to characterize transformed and untransformed cell structure and epidermal surfaces. Leaf surfaces are also examined for normal stomate structure and density using epidermal peels (Ristic et al., *Bot. Gaz.*, 152, 173 (1991)).

The invention has been described with reference to various specific and preferred embodiments and will be further described by reference to the following detailed examples. It is understood, however, that there are many extensions, variations, and modifications on the basic theme of the present invention beyond that shown in the examples and description, which are within the spirit and scope of the present invention.

EXAMPLE I

Because a link was observed between (1) the maintenance of turgor level via shifts in osmotic potential and yield of hybrids under stress conditions, and (2) more negative osmotic potentials and increased yield levels in hybrids under irrigated conditions, monocot cells were transformed with a preselected DNA segment encoding an enzyme which catalyzes the synthesis of an osmoprotectant so as to result in a transformed monocot plant with improved cellular osmotic relations. The expression of the preselected DNA segment includes expression in the cytosol or the chloroplast, or both. In addition to constitutive gene expression, differential expression in shoots, roots and reproductive tissues, developmental, temporal, as well as inducible expression of a preselected DNA segment, is within the scope of the invention.

Monocot plant cells can be transformed with more than one preselected DNA segment, so as to result in a synergistic effect for plant performance, under either, or both, water-stress and non water-stress conditions. Thus, it is also contemplated that expression of a preselected DNA segment in plants, when those plants are grown under relatively non-stress conditions or typical conditions, can result in a yield performance over plants which do not express the preselected DNA segment, or do not express the DNA at altered, increased or elevated levels.

Construction of mtlD Vectors

One embodiment of the invention is a vector constructed to direct constitutive expression of the preselected DNA segment. For example, a preferred embodiment of the invention is an expression cassette comprising the Cauliflower Mosaic Virus 35S promoter (Odell et al., *Nature* (1985)) 5' to the mtlD gene. Alternatively the rice actin gene promoter (Wang et al., *Mol. Cell. Biol.*, 12, 3399 (1992)) is placed 5' of the mtlD gene. It is anticipated that all promoters which direct constitutive gene expression in maize will be useful when operably linked to a mtlD gene. Sequences which direct polyadenylation are preferably linked 3' to the mtlD gene. These sequences include, but are not limited to, DNA sequences isolated from the 3' region of *Agrobacterium tumefaciens* nopaline synthase, octopine synthase or transcript 7, or potato proteinase inhibitor II genes. It is anticipated that constitutive expression of the mtlD gene in all tissues of a monocot plant, such as maize, will enhance the ability of the plant to maintain water turgor under conditions of decreased water availability.

It is further contemplated that tissue specific expression of a preselected DNA segment, e.g., mtlD, will enhance the agronomic performance of a monocot plant, such as maize. Vectors for use in tissue-specific targeting of mtlD genes in transgenic plants will typically include tissue-specific promoters and may also include other tissue-specific control elements such as enhancer sequences. Promoters which direct specific or enhanced expression in certain plant tissues will be known to those of skill in the art in light of the present disclosure. These include, for example, the rbcS promoter, specific for green tissue; the ocs, nos and mas promoters which have higher activity in roots or wounded leaf tissue; a truncated (−90 to +8) 35S promoter which directs enhanced expression in roots, an α-tubulin gene that directs expression in roots and promoters derived from zein storage protein genes which direct expression in endosperm. It is particularly contemplated that one may advantageously use the 16 bp ocs enhancer element from the octopine synthase (ocs) gene (Ellis et al., *EMBO J.*, 6, 3203 (1987)); Bouchez et al., *EMBO J.*, 8, 4197 (1989)), especially when present in multiple copies, to achieve enhanced expression in roots.

Expression of mtlD in transgenic plants may be desired under specified conditions. For example, the expression of mtlD genes may be desired only under actual stress conditions. It is known that a large number of genes exist that respond to the environment. For example, expression of some genes such as rbcS, encoding the small subunit of ribulose bisphosphate carboxylase, is regulated by light as mediated through phytochrome. Other genes are induced by secondary stimuli. For example, synthesis of abscisic acid (ABA) is induced by certain environmental factors, including but not limited to water stress. A number of genes have been shown to be induced by ABA (Skriver et al., *Plant Cell*, 2, 503 (1990)). Promoter regions that regulate expression of these genes will be useful when operably linked to mtlD.

It is proposed that in some embodiments of the present invention expression of mtlD in a transgenic plant will be desired only in a certain time period during the development of the plant. Developmental timing is frequently correlated with tissue specific gene expression. For example, expression of zein storage proteins is initiated in the endosperm about 15 days after pollination.

To provide a transgenic monocot plant that is substantially resistant or tolerant to a reduction in water availability, several vectors were constructed containing a gene that encodes an enzyme which catalyzes the synthesis of an osmoprotectant. Such genes include, but are not limited to, the mtlD gene from *E. coli* and the HVA-1 gene from barley. The mannitol operon was originally cloned and characterized by Lee et al. (*J. Bacteriol.*, 153, 685 (1983)). The mtlD gene has been shown to confer water stress resistance on transgenic tobacco plants (Tarczynski et al., *Science*, 259, 508 (1993)).

*Construction of vector pDPG451.* The mannitol operon (mtlC, mtlA, mtlD) was obtained as a plasmid in C600 *E. coli* from Malthius Muller, Univ. of Freiburg (pDPG409). To isolate the plasmid DNA, the plasmid was first amplified using chloramphenicol and then isolated using Qiagen large-scale plasmid preparation. The mtlD gene was excised from the pDPG409 plasmid by digesting the DNA with restriction enzymes NsiI and PstI. The digested DNA was run on a 1.1% SeaKem agarose gel in TAE buffer (see Sambrook et al., *Molecular Cloning*: A Laboratory Manual (1989)) to separate the fragments by size and the appropriate fragment was isolated from the gel using S&S NA45 membrane (Schleicher & Schuell, Keene, N.H.).

The mtlD gene fragment was next cloned into the maize expression vector pDPG431 (35S promoter-adh1 Intron1-Tr7 3' end). Vector pDPG431 DNA was digested with restriction enzymes NsiI and PstI to open up the backbone and the mtlD fragment inserted by ligation. The ligated DNA was transformed into DH5α cells and the resulting colonies screened by mini-preps to identified those containing the correct gene construct. The new vector was designated pDPG451. A map of the plasmid is shown in FIG. 1.

Construction of vector pDPG480. The NsiI-PstI fragment from vector pDPG409 containing the mtlD gene used to construct pDPG451 was cut with restriction enzymes AvaI and HindIII. This removed about 122 bp of untranslated sequence from the 5' end of the mtlD fragment and about 69 bp of untranslated sequence from the 3' end of the fragment. The AvaI—HindIII fragment was ligated into pUC19 DNA that had previously been digested with AvaI and HindIII to open up the plasmid backbone in the region of the multiple cloning sites. The pUC19/mtlD construct was then digested with restriction enzymes SacI and HindIII to release a fragment containing the mtlD gene. This fragment was isolated by running the digestion reaction on an agarose gel and the appropriately-sized fragment extracted from the gel using a S&S Elu-Quik DNA purification kit, per the manufacturer's instructions.

Figure 3:
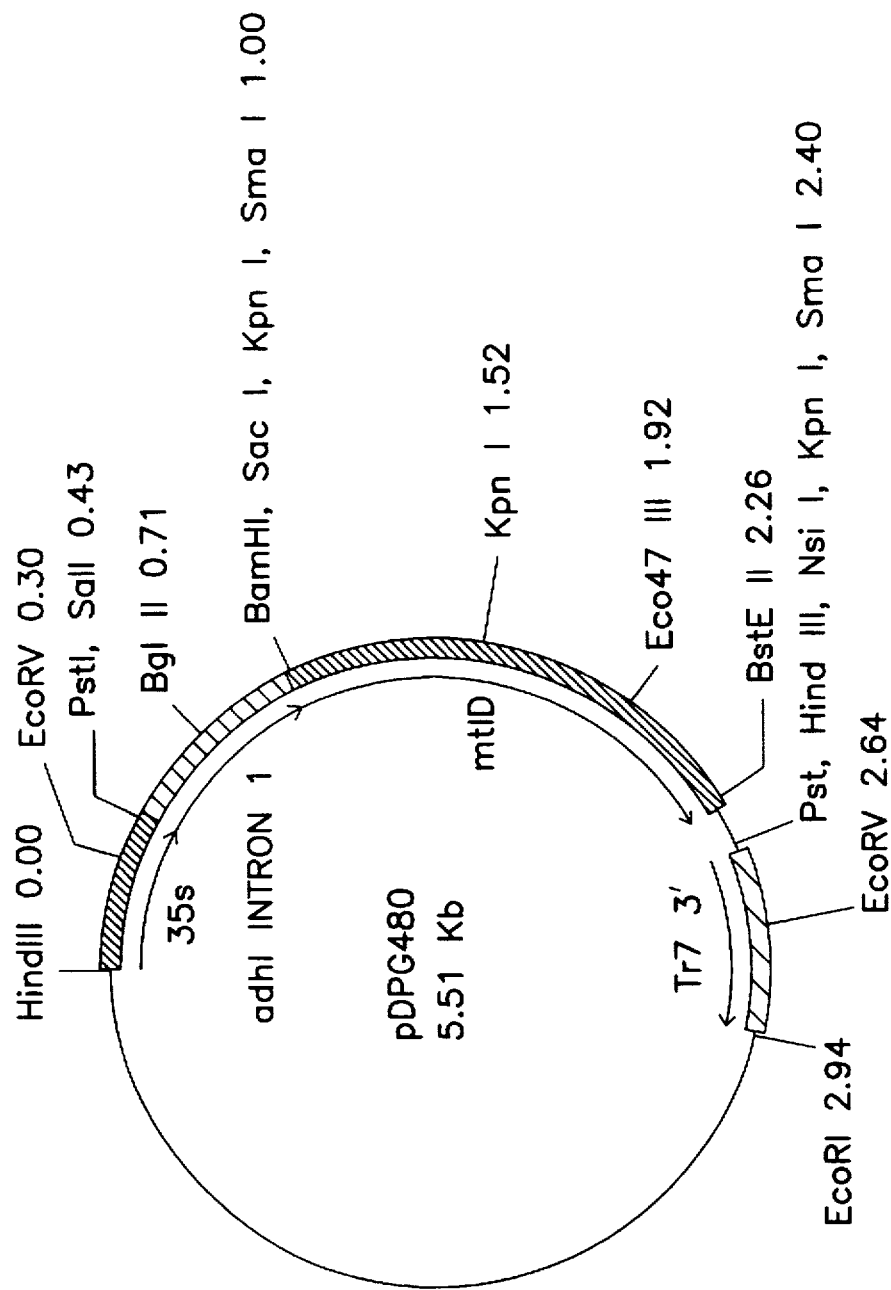
FIG. 3. A schematic diagram of plasmid pDPG480.

The DNA fragment was next ligated into pcDNAII DNA that had previously been digested with SacI and HindIII to open up the plasmid backbone in the region of the multiple cloning sites. The pcDNAII/mtlD vector was then digested with restriction enzymes BamHI and PstI to release a fragment containing the mtlD gene. This fragment was isolated by running the digestion reaction on an agarose gel and the appropriately-sized fragment extracted from the gel using a S&S Elu-Quik DNA purification kit, per the manufacturer's instructions. The DNA fragment was next ligated into pDPG431 DNA that had previously been digested with the restriction enzymes BamHI and PstI and the backbone fragment containing the 35S promoter-adhI Intron1 and Tr7 3' end isolated by gel purification. The resulting maize expression vector was designated pDPG480. A map of the plasmid is shown in FIG. 3.

Construction of vector pDPG493. DNA from vector pDPG480 was modified to remove approximately 120 bp of untranslated DNA from the 3' end of the mtlD gene fragment. To modify the 3' region, two oligonucleotides were made (DNA International, Inc.) to anneal together and then used to replace about 150 bp of the 3' end of the mtlD gene fragment. The first oligonucleotide (mtlD-B1) had a sequence of: 5' GTA ACC GCT TAT AAA GCA ATG CAA TAA TGA GTA CTC TGC AG 3' (SEQ ID NO: 1). The second oligonucleotide (mtlD-B2) had a sequence of: 5' GAG TAC TCA TTA TTG CAT TGC TTT ATA AGC G 3' (SEQ ID NO: 2). The annealed oligos duplicated the last twenty base pairs of the mtlD gene starting at the BstEII restriction site and running up to and including the stop codon and created a new sequence after the stop codon. This new sequence created new ScaI and PstI sites.

Figure 4:
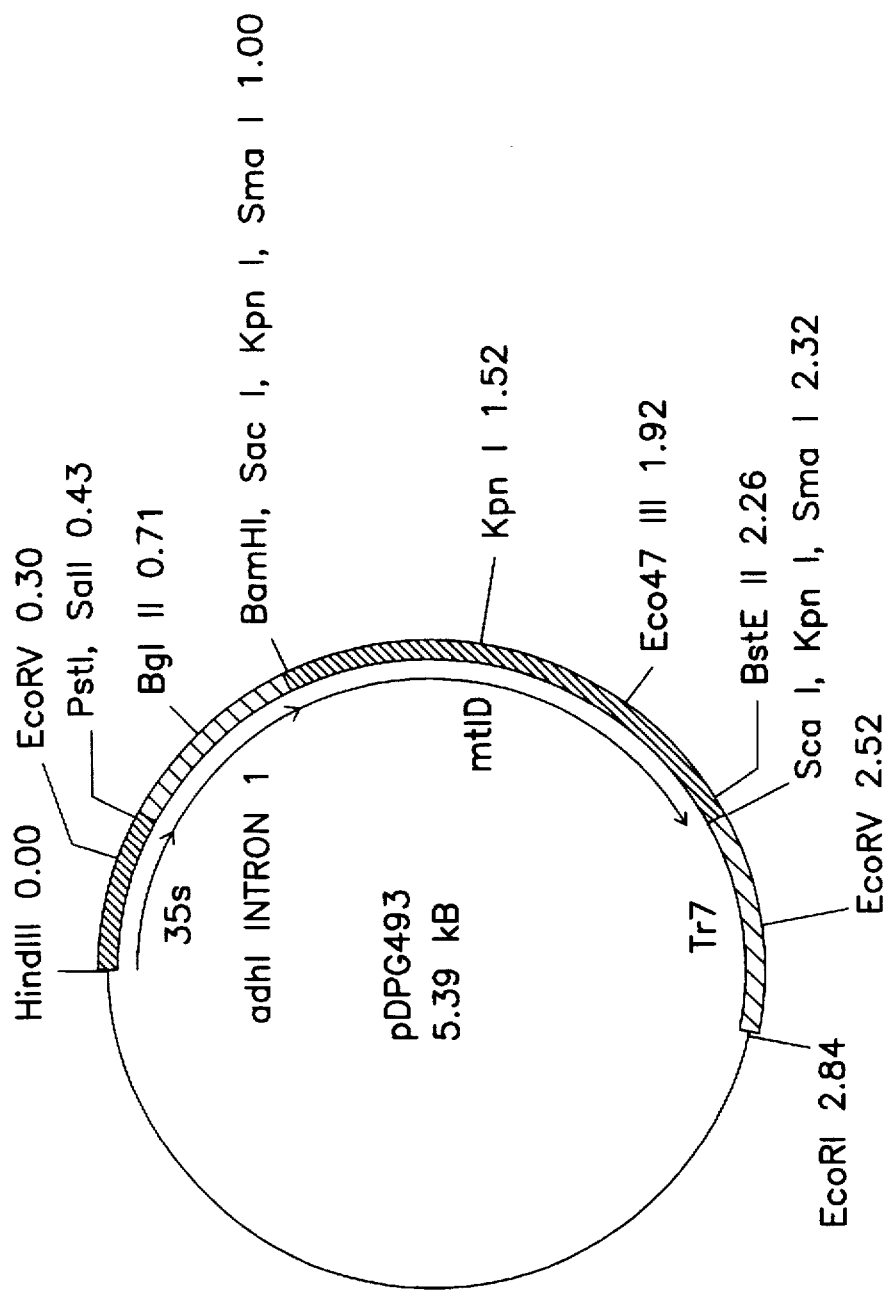
FIG. 4. A schematic diagram of plasmid pDPG493.

The new vector was constructed in the following manner. Vector pDPG480 plasmid DNA was digested with restriction enzymes BstEII and NsiI to remove the 3' end of the gene fragment. The digested DNA was run on an agarose gel to size separate the fragments and the appropriately-sized vector fragment was extracted from the gel using a S&S Elu-Quik DNA purification kit, per the manufacturer's instructions. Oligonucleotides mtlD-B1 and mtlD-B2 were annealed together and ligated into the digested pDPG480 DNA fragment. The resulting vector was designated pDPG493. A map of the plasmid is shown in FIG. 4.

Figure 5:
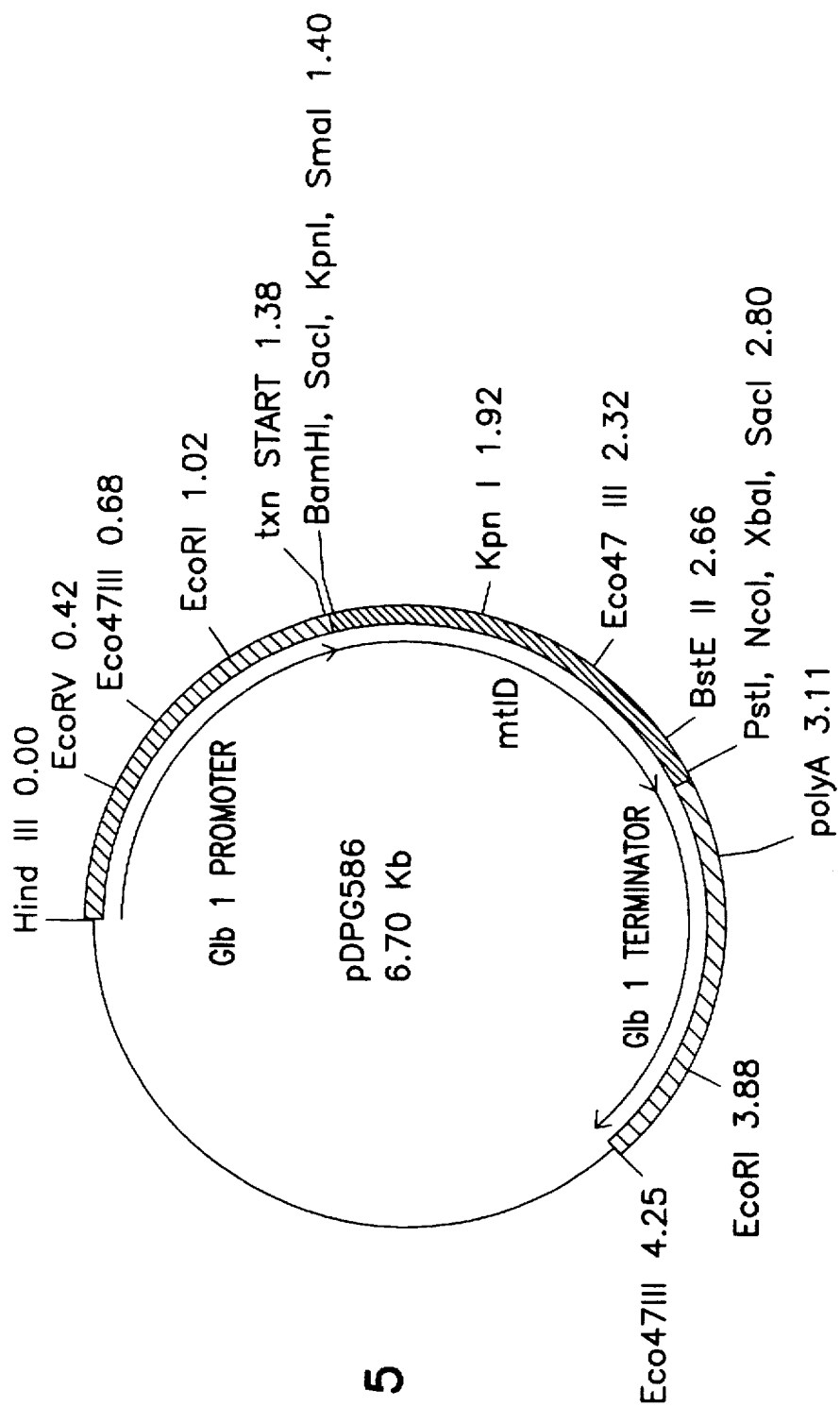
FIG. 5. A schematic diagram of plasmid pDPG586.

Construction of vector pDPG586. A DNA fragment containing the mtlD gene was removed from vector pDPG480 by digesting the plasmid DNA with restriction enzymes BamHII and PstI. The DNA fragment containing the gene was isolated by gel purification and extraction from the gel using a S&S Elu-Quik DNA purification kit per the manufacturer's instructions. A DNA fragment containing the Glb1 promoter and Glb1 terminator was isolated by digesting vector pDPG423 DNA with restriction enzymes BamHI and PstI to open up the backbone in the polylinker region. The two fragments were then ligated together to create vector pDPG586. A map of the plasmid is shown in FIG. 5.

Construction of vector pDPG587. Vector pDPG411 was digested with restriction enzymes XhoI and SacI to release a DNA fragment containing the 35S promoter and a maize transit peptide sequence (MZTP). This DNA fragment was isolated by gel purification and extraction from the gel using a S&S Elu-Quik DNA purification kit per the manufacturer's instructions. A DNA backbone fragment containing the mtlD gene was generated by digesting the pcDNAII/mtlD vector described above with restriction enzymes XhoI and NsiI to open up the vector in the polylinker region. These two fragments along with a Nsi-StuI-SacI linker (Keystone Laboratories, Inc.) were ligated together to create a vector designated MZTP/mtlD. Plasmid DNA of this vector was digested with restriction enzyme PstI to open up the vector at the 3' end of the mtlD gene sequence.

Figure 6:
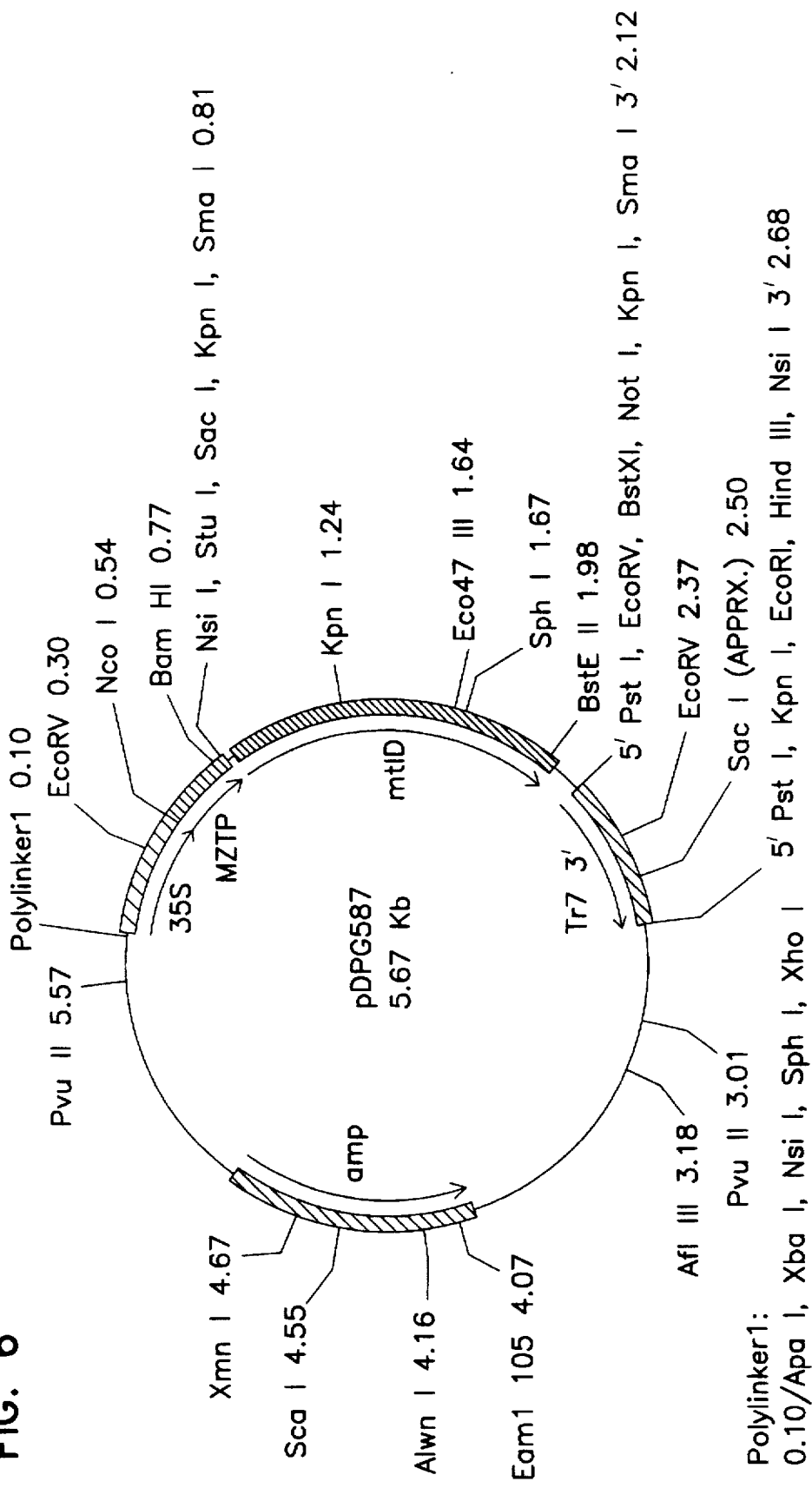
FIG. 6. A schematic diagram of plasmid pDPG587.

A DNA fragment containing the Tr7 terminator was isolated from plasmid DNA of vector pDPG527 by digesting with restriction enzyme PstI. This DNA fragment was isolated by gel purification and extraction from the gel using a S&S Elu-Quik DNA purification kit per the manufacturer's instructions. The MZTP/mtlD and Tr7 terminator DNA fragments were ligated together to create the maize expression vector pDPG587. The region from the end of the 35S promoter, through the MZTP sequence and into the mtlD gene was sequenced by dideoxy DNA sequencing to confirm the correct composition of this region and to ensure that the MZTP and mtlD gene are in frame with one another. A map of the plasmid is shown in FIG. 6.

An additional expression vector for the mtlD gene was created by removing the bar gene from pDPG182 using SmaI. After blunting the ends of the mtlD gene, it was ligated into the pUC-based vector; between the maize AdhI promoter/AdhI, intron and the transcript 7 3' end from *Agrobacterium tumefaciens* (provided in pCEV5 from Calgene, Inc., Davis, Calif.). This plasmid vector was designated pDPG469.

EXAMPLE II

Preparation of Type II Callus for Transformation Initiation and Maintenance of Cell Line AT824

Immature embryos (0.5–1.0 mm) were excised from the B73-derived inbred line AT and cultured on N6 medium with 100 μM silver nitrate, 3.3 mg/L dicamba, 3% sucrose and 12 mM proline (Medium 2004, see Table 1). Six months after initiation, type I callus was transferred to Medium 2008. Two months later type I callus was transferred to a medium with a lower concentration of sucrose (Medium 279). A sector of type II callus was identified 17 months later and was transferred to Medium 279. This cell line is uniform in nature, unorganized, rapid growing, and embryogenic. This culture is easily adaptable to culture in liquid or on solid medium.

The first suspension cultures of AT824 were initiated 31 months after culture initiation. Suspension cultures were initiated in a variety of culture media including media containing 2,4-D as well as dicamba as the auxin source, e.g., media designated 210, 401, 409, 279. Cultures were maintained by transfer of approximately 2 ml packed cell volume (PCV) to 20 ml fresh culture medium at 3.5 day intervals. AT824 was routinely transferred between liquid and solid culture media with no effect on growth or morphology.

Suspension cultures of AT824 were initially cryopreserved 33–37 months after culture initiation. The survival rate of this culture was improved when it was cryopreserved following three months in suspension culture. AT824 suspension cultures have been cryopreserved and reinitiated from cryopreservation at regular intervals since the initial date of freezing. Repeated cycles of freezing have not affected the growth or transformability of this culture.

TABLE 1

Illustrative Embodiments of Tissue Culture Media Which are Used for Type II Callus Development, Development of Suspension Cultures and Regeneration of Plant Cells (Specifically Maize Cells)

| MEDIA NO. | BASAL MEDIUM | SUCROSE | pH | OTHER COMPONENTS** (Amount/L) |
|---|---|---|---|---|
| 101 | MS | 3% | 6.0 | MS vitamins<br>100 mg myo-inositol<br>Bactoagar |
| 189 | MS | — | 5.8 | 3 mg BAP<br>.04 mg NAA<br>.5 mg niacin<br>800 mg L-asparagine<br>100 mg casaminoacids<br>20 g sorbitol<br>1.4 g L-proline<br>100 mg myo-inositol<br>Gelgro |
| 201 | N6 | 2% | 5.8 | N6 vitamins<br>2 mg L-glycine<br>1 mg 2,4-D<br>100 mg casein hydrolysate<br>2.9 g L-proline<br>Gelgro |
| 210 | N6 | 3% | 5.5 | N6 vitamins<br>2 mg 2,4-D<br>250 mg Ca pantothenate<br>100 mg myo-inositol<br>790 mg L-asparagine<br>100 mg casein hydrolysate<br>1.4 g L-proline<br>2 mg glycine<br>Hazelton agar |
| 223 | N6 | 2% | 5.8 | 3.3 mg dicamba<br>1 mg thiamine<br>0.5 mg niacin<br>800 mg L-asparagine<br>100 mg casein hydrolysate<br>100 mg myo-inositol<br>1.4 g proline<br>Gelgro<br>3 mg bialaphos |
| 227 | N6 | 2% | 5.8 | 2 mg L-glycine<br>100 mg casein hydrolysate<br>2.9 g L-proline<br>Gelgro |
| 279 | N6 | 2% | 5.8 | 3.3 mg dicamba<br>1 mg thiamine<br>0.5 mg niacin<br>800 mg L-asparagine<br>100 mg casein hydrolysate<br>100 mg myo-inositol<br>1.4 g proline<br>Gelgro |
| 401 | MS | 3% | 6.0 | 3.73 mg Na$_2$EDTA<br>0.25 mg thiamine<br>1 mg 2,4-D<br>2 mg NAA<br>200 mg casein hydrolysate<br>500 mg K$_2$SO$_4$<br>400 mg KH$_2$PO$_4$<br>100 mg myo-inositol |
| 409 | MS | 3% | 6.0 | 3.73 mg Na$_2$EDTA<br>0.25 mg thiamine<br>9.9 mg dicamba<br>200 mg casein hydrolysate<br>500 mg K$_2$SO$_4$<br>400 mg KH$_2$PO$_4$<br>100 mg myo-inositol |
| 425 | MS | 3% | 6.0 | 3.73 mg Na$_2$EDTA<br>0.25 mg thiamine<br>9.9 mg dicamba<br>200 mg casein hydrolysate<br>500 mg K$_2$SO$_4$<br>400 mg KH$_2$PO$_4$<br>100 mg myo-inositol<br>3 mg bialaphos |
| 501 | Clark's Medium* | 2% | 5.7 | |
| 607 | 0.5x MS | 3% | 5.8 | 0.5 mg thiamine<br>0.5 mg niacin<br>Gelrite |
| 734 | N6 | 2% | 5.8 | N6 vitamins<br>2 mg L-glycine<br>1.5 mg 2,4-D<br>14 g Fe sequestrene<br>200 mg casein hydrolysate<br>0.69 g L-proline<br>Gelrite |
| 735 | N6 | 2% | 5.8 | 1 mg 2,4-D<br>0.5 mg niacin<br>0.91 g L-asparagine<br>100 mg myo-inositol<br>1 mg thiamine<br>0.5 g MES<br>0.75 g MgCl$_2$<br>100 mg casein hydrolysate<br>0.69 g L-proline<br>Gelgro |
| 739 | N6 | 2% | 5.8 | 1 mg 2,4-D<br>0.5 mg niacin<br>0.91 g L-asparagine<br>100 mg myo-inositol<br>1 mg thiamine<br>0.5 g MES |

TABLE 1-continued

Illustrative Embodiments of Tissue Culture Media Which are Used for Type II Callus Development, Development of Suspension Cultures and Regeneration of Plant Cells (Specifically Maize Cells)

| MEDIA NO. | BASAL MEDIUM | SUCROSE | pH | OTHER COMPONENTS** (Amount/L) |
|---|---|---|---|---|
| 750 | N6 | 2% | 5.8 | 0.75 g MgCl$_2$<br>100 mg casein hydrolysate<br>0.69 g L-proline<br>Gelgro<br>1 mg bialaphos<br>1 mg 2,4-D<br>0.5 mg niacin<br>0.91 g L-asparagine<br>100 mg myo-inositol<br>1 mg thiamine<br>0.5 g MES |
| 758 | N6 | 2% | 5.8 | 0.75 g MgCl$_2$<br>100 mg casein hydrolysate<br>0.69 g L-proline<br>Gelgro<br>0.2 M mannitol<br>1 mg bialaphos<br>1 mg 2,4-D<br>0.5 mg niacin<br>0.91 g L-asparagine<br>100 mg myo-inositol<br>1 mg thiamine<br>0.5 g MES |
| 2004 | N6 | 3% | 5.8 | 0.75 g MgCl$_2$<br>100 mg casein hydrolysate<br>0.69 g L-proline<br>Gelgro<br>3 mg bialaphos<br>1 mg thiamine<br>0.5 mg niacin<br>3.3 mg dicamba<br>17 mg AgNO3<br>1.4 g L-proline<br>0.8 g L-asparagine<br>100 mg casein hydrolysate<br>100 mg myo-inositol<br>Gelrite |
| 2008 | N6 | 3% | 5.8 | 1 mg thiamine<br>0.5 mg niacin<br>3.3 mg dicamba<br>1.4 g L-proline<br>0.8 g L-asparagine |

Basic MS medium described in Murashige et al., (cited supra (1962)). This medium is typically modified by decreasing the NH$_4$NO$_3$ from 1.64 g/l to 1.55 g/l, and omitting the pyridoxine HCl, nicotinic acid, myo-inositol and glycine. N6 medium described in Chu et al., *Scientia Sinica*, 18, 659 (1975).
NAA = Napthol Acetic Acid
IAA = Indole Acetic Acid
2-IP = 2, isopentyl adenine
2,4-D = 2,4-Dichlorophenoxyacetic Acid
BAP = 6-benzyl aminopurine
ABA = abscisic acid
*Basic medium described in Clark, J. Plant Nutrition, 5, 1039 (1982)

Initiation and Maintenance of Type II callus of the genotype Hi-II.

The Hi-II genotype of corn was developed from an A188 x B73 cross. This genotype was developed specifically for a high frequency of initiation of type II cultures (100% response rate, Armstrong et al., *Maize Genetics Coop Newsletter*, 65, 92 (1991)). Immature embryos (8–12 days post-pollination, 1 to 1.2 mm) were excised and cultured embryonic axis down on N6 medium containing 1 mg/L 2,4-D, 25 mM L-proline (Medium 201) or N6 medium containing 1.5 mg/L 2,4-D, 6 mM L-proline (Medium 734).

Type II callus was initiated either with or without the presence of 100 µM AgNO$_3$. Cultures initiated in the presence of AgNO$_3$ were transferred to medium lacking this compound about 14–28 days after culture initiation. Callus cultures were incubated in the dark at about 23°–28° C. and transferred to fresh culture medium at about 14–21 day intervals.

Hi-II type II callus was maintained by manual selection of callus at each transfer. Alternatively, callus was resuspended in liquid culture medium, passed through a 1.9 mm sieve and replated on solid culture medium at the time of transfer. This sequence of manipulations enriches for recipient cell types. Regenerable Type II callus that is suitable for transformation was routinely developed from the Hi-II genotype and hence new cultures were developed every 6–9 months. Routine generation of new cultures reduces the period of time over which each culture is maintained and hence insures reproducible, highly regenerable, cultures that routinely produce fertile plants.

Initiation of embryos of the genotype Hi-II.

Immature embryos of the Hi-II genotype (8–12 days post pollination, 1.0–2.5 mm) were excised and cultured embryonic axis down on Medium 201, or other equivalent or similar medias, with or without the addition of 100 µM AgNO$_3$. Immature embryos were cultured in the dark at about 23°–28° C. for about 0–14, preferably about 2–4, days prior to transformation.

EXAMPLE III

Transformation of Cell Cultures
Microprojectile Bombardment: AT824.

AT824 suspension culture cells were subcultured to fresh Medium 401, at about 0–3, preferably at about 2, days prior to particle bombardment. Cells were plated on to solid Medium 279, or other similar medias, at about 0–24, preferably about 4, hours before bombardment of about 0.5–1.0 ml packed cell volume per filter. Tissue can be treated with or without the addition of about 200 mOsm sorbitol or mannitol for about 0–5, preferably about 3, hours prior to bombardment.

DNA was precipitated on to gold particles as follows. A stock solution of gold particles was prepared by adding 60 mg of 1 µm gold particles to 1000 µl absolute ethanol and incubating for at least 3 hours at room temperature followed by storage at about −20° C. Twenty to thirty-five µl sterile gold particles are centrifuged in a microcentrifuge for 1 minute. The supernatant is removed and one ml sterile water is added to the tube, followed by centrifugation at 2000 rpm for 5 minutes. Microprojectile particles are resuspended in 30 µg total DNA containing a selectable marker, such as bar, EPSPS, or deh, and the mtlD gene which is operably linked to a promoter. Approximately 220 µl sterile water, 250 µl 2.5 M CaCl$_2$, and 50 ul spermidine stock are then added. The mixture is thoroughly mixed and placed on ice, followed by vortexing at 4° C. for 10 minutes and centrifugation at 500 rpm for 5 minutes. The supernatant is removed and the pellet resuspended in 600 µl absolute ethanol. Following centrifugation at 500 rpm for 5 minutes the pellet is resuspended in 36 µl of absolute ethanol.

Approximately 5–10 µl of the particle preparation was dispensed on the surface of the flyer disk and the ethanol was allowed to dry completely. DNA was introduced into cells using the DuPont Biolistics PDS1000He particle bombardment device. Particles were accelerated by a helium blast of approximately 1100 psi. Zero to seven, preferably about 1–4, days following bombardment, cells were transferred to 10–20 mls liquid Medium 401, or other similar medias.

Tissue was subcultured twice per week. In most cases, during the first week there was no selection pressure applied. Microprojectile Bombardment: Type II callus from the genotype Hi-II.

Hi-II callus cultures are bombarded similarly to AT824 suspension cultures. Approximately 0.5–1.0 ml packed cell volume was plated on to Whatman filters after a brief liquid phase. Cells were either plated on to solid media or left on a bed of wet filters prior to bombardment. Cells can be bombarded with or without the addition of an osmoticum before bombardment (liquid or solid) in a manner similar to that described above for AT824. Following particle bombardment cells remained on solid Medium 201, or other similar medias, in the absence of selection for about 0–2 weeks, preferably for about 1 week. At this time cells were removed from solid medium, resuspended in liquid Medium 201, or other similar medias, replated on Whatman filters at about 0.1–1.0 ml PCV per filter, and transferred to Medium 201, or other similar medias, containing about 0.5–3.0 mg/L bialophos.

Bombardment of Immature Embryos.

Immature embryos (1.0–2.5 mm in length) were excised from surface-sterilized, greenhouse-grown ears of Hi-II about 10–12 days post-pollination. Approximately 30 embryos per petri dish were plated axis side down on Medium 201, or other similar medias. Embryos were cultured in the dark for about 1–14 days at about 23°–28° C.

Approximately four hours prior to bombardment, embryos were transferred to Medium 201 with the sucrose concentration increased from about 3% to 12%. When embryos were transferred to the high osmoticum medium they were arranged in concentric circles on the plate, starting 2 cm from the center of the dish, positioned such that their coleorhizal end was orientated toward the center of the dish. Usually two concentric circles were formed with about 25–35 embryos per plate.

Preparation of gold particles carrying plasmid DNA was performed as described above. The plates containing embryos were then placed on the third shelf from the bottom, at about 5 cm below the stopping screen. The 1100 psi rupture discs were used. Each plate of embryos was bombarded once. Embryos were allowed to recover about 0–7, preferably about 1, days on high osmotic strength medium prior to initiation of selection.

Stable Transformation of SC716 and AT824 Cells Using pDPG165 and pDPG208 by Electroporation Maize suspension culture cells were enzyme treated and electroporated using conditions described in Krzyzek et al. (PCT Publication WO 92/12250, incorporated by reference herein). SC716 or AT824 suspension culture cells, three days post subculture, were sieved through 1000 μm stainless steel mesh and washed, 1.5 ml packed cells per 10 ml, in incubation buffer (0.2 M mannitol, 0.1% bovine serum albumin, 80 mM calcium chloride, and 20 mM 2-(N-morpholino)-ethane sulfonic acid (MES), pH 5.6). Cells were then treated for 90 minutes in incubation buffer containing 0.5% pectolyase Y-23 (Seishin Pharmaceutical, Tokyo, Japan) at a density of 1.5 ml packed cells per 5 ml of enzyme solution. During the enzyme treatment, cells were incubated in the dark at approximately 25° C. on a rotary shaker at 60 rpm. Following pectolyase treatment, cells were washed once with 10 ml of incubation buffer followed by three washes with electroporation buffer (10 mM 4-(2-Hydroxyethyl)-1-piperazineethanesulfonic acid (HEPES), 0.4 mM mannitol). Cells were resuspended in electroporation buffer at a density of 1.5 ml packed cells in a total volume of 3 ml.

Linearized plasmid DNA. 100 μg of EcoRI digested pDPG165 and 100 μg of EcoRI digested pDPG208, was added to 1 ml aliquots of electroporation buffer. The DNA/electroporation buffer was incubated at room temperature for approximately 10 minutes. To these aliquots, 1 ml of suspension culture cells/electroporation buffer (containing approximately 0.5 ml packed cells) were added. Cells and DNA in electroporation buffer were incubated at room temperature for approximately 10 minutes. One half ml aliquots of this mixture were transferred to the electroporation chamber (Puite, Plant Cell Rep., 4, 274 (1985)) which was placed in a sterile 60×15 mm petri dish. Cells were electroporated with a 70, 100, or 140 volt (V) pulse discharged from a 140 microfarad (μf) capacitor.

Approximately 10 minutes post-electroporation, cells were diluted with 2.5 ml Medium 409 containing 0.3 M mannitol. Cells were then separated from most of the liquid medium by drawing the suspension up in a pipet, and expelling the medium with the tip of the pipet placed against the petri dish to retain the cells. The cells, and a small amount of medium (approximately 0.2 ml) were dispensed onto a filter (Whatman #1, 4.25 cm) overlaying solid Medium 227 (Table 1) containing 0.3 M mannitol. After five days, the tissue and the supporting filters were transferred to Medium 227 containing 0.2 M mannitol. After seven days, tissue and supporting filters were transferred to Medium 227 without mannitol.

Electroporation of Immature embryos

Immature embryos (0.4–1.8 mm in length) were excised from a surface-sterilized, greenhouse-grown ear of the genotype H99 11 days post-pollination. Embryos were plated axis side down on a modified N6 medium containing 3.3 mg/l dicamba, 100 mg/l casein hydrolysate, 12 mM L-proline, and 3% sucrose solidified with 2 g/l Gelgro®, p5.8 (Medium 726), with about 30 embryos per dish. Embryos were cultured in the dark for two days at about 24° C.

Immediately prior to electroporation, embryos were enzymatically treated with 0.5% Pectolyase Y-23 (Seishin Pharmaceutical Co.) in a buffer containing 0.2 M mannitol, 0.2% bovine serum albumin, 80 mM calcium chloride and 20 mM 2-(N-morpholino)-ethane sulfonic acid (MES) at pH 5.6. Enzymatic digestion was carried out for 5 minutes at room temperature. Approximately 140 embryos were treated in batch in 2 ml of enzyme and buffer. The embryos were washed two times with 1 ml of 0.2 M mannitol, 0.2% bovine serum albumin, 80 mM calcium chloride and 20 mM MES at pH 5.6 followed by three rinses with electroporation buffer consisting of 10 mM HEPES and 0.4 M mannitol at pH 7.5. For the electroporations, the final rinse of electroporation buffer was removed and the embryos were incubated with 0.33 mg/ml linearized pDPG165, 0.33 mg/ml supercoiled pDPG215, or 0.33 mg/ml linearized pDPG344 in electroporation buffer. One half ml aliquots of DNA in electroporation buffer and twenty embryos were transferred to the electroporation chamber that was placed in a sterile 60×15 mm petri dish. An electrical pulse was passed through the cells from a 500 μf capacitor that was charged to 100 volts (400 V/cm field strength, 160 ms pulse decay time; exponential pulse).

Immediately following electroporation, embryos were diluted 1:10 with Medium 726 containing 0.3 M mannitol. Embryos were then transferred to Gelgro® solidified Medium 726 containing 0.3 M mannitol. Embryos were incubated in the dark at about 24° C. After five days embryos were transferred to Gelgro solidified Medium 726 containing 0.2 M mannitol. Two days later embryos were transferred to selection medium.

EXAMPLE IV

Identification of Transformed Cells Using Selectable Markers

In order to provide a more efficient system for identification of those cells receiving DNA and integrating it into their genomes, it is desirable to employ a means for selecting those cells that are stably transformed. One exemplary embodiment of such a method is to introduce into the host cell a marker gene which confers resistance to some normally inhibitory agent, e.g., an antibiotic or herbicide. The potentially transformed cells are then exposed to the agent. In the population of surviving cells are those cells wherein generally the resistance-conferring gene has been integrated and expressed at sufficient levels to permit cell survival. Cells may be tested further to confirm stable integration of the exogenous DNA. Using embryogenic suspension cultures, stable transformants are recovered at a frequency of approximately 1 per 1000 transiently expressing foci.

One of the difficulties in cereal transformation, e.g., corn, has been the lack of an effective selective agent for transformed cells, from totipotent cultures (Potrykus, *Trends Biotech*, 7, 269 (1989)). Stable transformants were recovered from bombarded nonembryogenic Black Mexican Sweet (BMS) maize suspension culture cells, using the neo gene and selection with the aminoglycoside, kanamycin (Klein et al., *Plant Physiol.*, 91, 440 (1989). This approach, while applicable to the present invention, is not preferred because many monocots are insensitive to high concentrations of aminoglycosides (Dekeyser et al., *Plant Physiol.*, 90, 21-7 (1989); Hauptmann et al., *Plant Physiol.*, 86, 602 (1988)). The stage of cell growth, duration of exposure and concentration of the antibiotic, may be critical to the successful use of aminoglycosides as selective agents to identify transformants (Lyznik et al., *Plant Mol. Biol.*, 13, 151 (1989)); Yang et al., *Plant Cell Rep.*, 7, 421 (1988); Zhang et al., *Plant Cell Rep.*, 7, 379 (1988)). For example, D'Halluin et al. (*The Plant Cell*, 4, 1495 (1992)) demonstrated that using the neo gene and selecting with kanamycin transformants could be isolated following electroporation of immature embryos of the genotype H99 or type I callus of the genotype PA91. In addition, use of the aminoglycosides, kanamycin or G418, to select stable transformants from embryogenic maize cultures can result in the isolation of resistant calli that do not contain the neo gene.

One herbicide which has been suggested as a desirable selection agent is the broad spectrum herbicide bialaphos. Bialaphos is a tripeptide antibiotic produced by *Streptomyces hygroscopicus* and is composed of phosphinothricin (PPT), an analogue of L-glutamic acid, and two L-alanine residues. Upon removal of the L-alanine residues by intracellular peptidases, the PPT is released and is a potent inhibitor of glutamine synthetase (GS), a pivotal enzyme involved in ammonia assimilation and nitrogen metabolism (Ogawa et al., *Sci. Rep.*, *Mejia Seika* 13, 42 (1973)). Synthetic PPT, also known as Glufosinate®, the active ingredient in the herbicides Basta® or Liberty® is also effective as a selection agent. Inhibition of GS in plants by PPT causes the rapid accumulation of ammonia and death of the plant cells.

The organism producing bialaphos and other species of the genus *Streptomyces* also synthesizes an enzyme phosphinothricin acetyl transferase (PAT) which is encoded by the bar gene in *Streptomyces hygroscopicus* and the pat gene in *Streptomyces viridochromogenes*. The use of the herbicide resistance gene encoding phosphinothricin acetyl transferase (PAT) is referred to in DE 3642 829 A wherein the gene is isolated from *Streptomyces viridochromogenes*. In the bacterial source organism, this enzyme acetylates the free amino group of PPT preventing auto-toxicity (Thompson et al., *EMBO J.*, 6, 2519 (1987)). The bar gene has been cloned (Murakami et al., *Mol. Gen. Genetics*, 205, 42 (1986); Thompson et al., supra) and expressed in transgenic tobacco, tomato and potato plants (De Block, *EMBO J.*, 6, 2513 (1987)) and Brassica (De Block et al., *Plant Physiol.*, 91, 694 (1989)). In previous reports, some transgenic plants which expressed the resistance gene were completely resistant to commercial formulations of PPT and bialaphos in greenhouses.

EP patent 0 242 236 refers to the use of a process for protecting plant cells and plants against the action of glutamine synthetase inhibitors. This application also refers to the use of such of a process to develop herbicide resistance in determined plants. The gene encoding resistance to the herbicide LIBERTY (Hoechst, phosphinothricin or Glufosinate®) or Herbiace (Meiji Seika, bialaphos) was said to be introduced by *Agrobacterium* infection into tobacco (*Nicotiana tabacum* cv Petit Havan SR1), potato (*Solanum tuberosum* cv Benolima) and tomato (*Lycopersicum esculentum*), and conferred on these plants resistance to application of herbicides.

Another herbicide which is useful for selection of transformed cell lines in the practice of this invention is the broad spectrum herbicide glyphosate. Glyphosate inhibits the action of the enzyme EPSPS which is active in the aromatic amino acid biosynthetic pathway. Inhibition of this enzyme leads to starvation for the amino acids phenylalanine, tyrosine, and tryptophan and secondary metabolites derived thereof. Comai et al., U.S. Pat. No. 4,535,060, issued Aug. 13, 1985 describe the isolation of EPSPS mutations which infer glyphosate resistance on the *Salmonella typhimurium* gene for EPSPS, aroA. The EPSPS gene was cloned from *Zea mays* and mutations similar to those found in a glyphosate resistant aroA gene were introduced in vitro. The mutant gene encodes a protein with amino acid changes at residues 102 and 106. Although these mutations confer resistance to glyphosate on the enzyme EPSPS, it is anticipated that other mutations confer the same phenotype.

Figure 2:
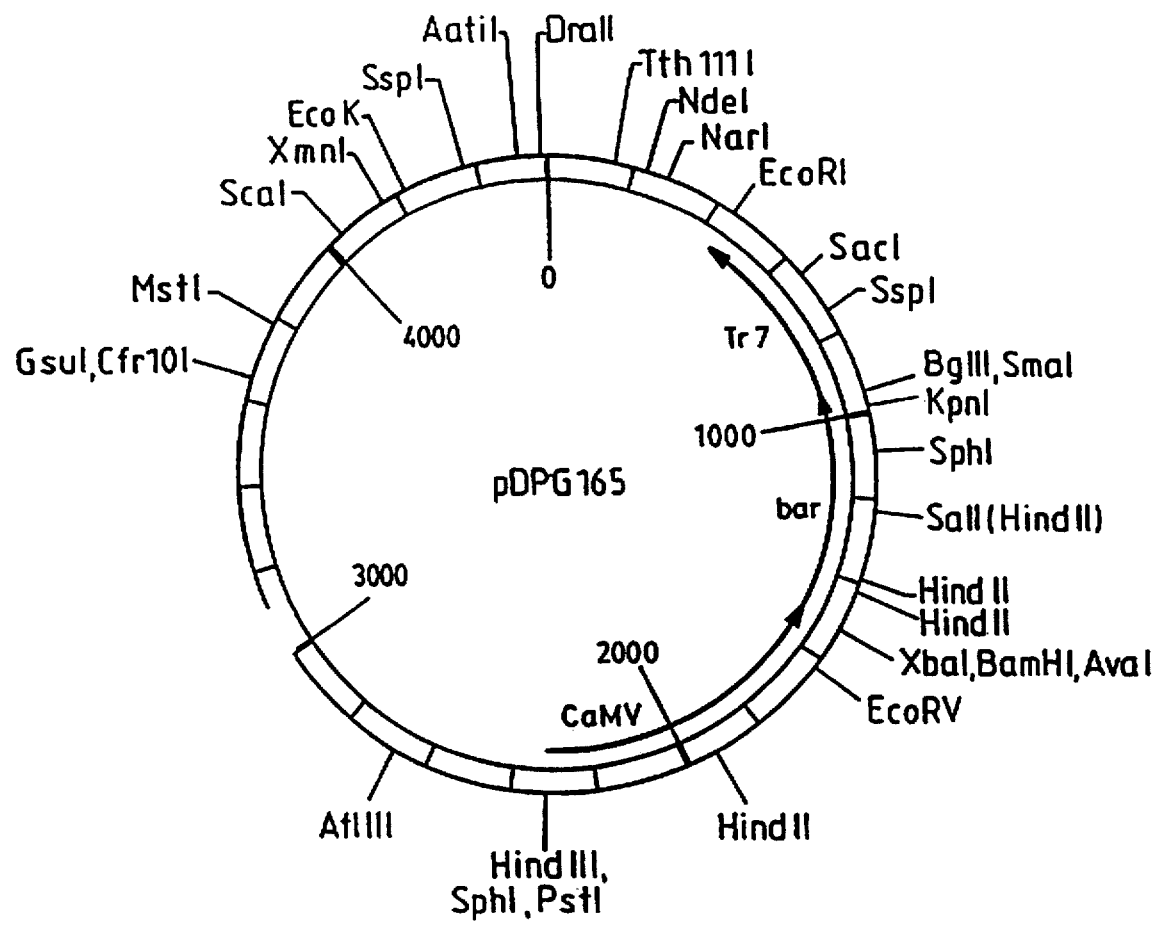
FIG. 2. A schematic diagram of plasmid pDPG165.

An exemplary embodiment of vectors capable of delivering DNA to plant host cells is the plasmid, pDPG165 and the vectors pDPG433, pDPG434, pDPG435, and pDPG436. The plasmid pDPG165 is illustrated in FIG. 2. A very important component of this plasmid for purposes of genetic transformation is the bar gene which encodes a marker for selection of transformed cells exposed to bialaphos or PPT. Plasmids pDPG434 and pDPG436 contain a maize EPSPS gene with mutations at amino acid residues 102 and 106 driven by the actin promoter and 35S promoter-Adh1 intron I, respectively. The mutated EPSPS gene encodes a marker for selection of transformed cells.

Transformation of Cell line AT824 Using Bialaphos Selection Following Particle Bombardment—Selection in Liquid Medium A suspension culture of AT824 was maintained in Medium 401. The bombardment was done as described above, with a few variations. Four filters of AT824 suspension cultures were plated out at approximately 0.75 ml PCV on to Medium 279. There were 4 filters bombarded with pDPG165 (FIG. 2, 35S-bar-Tr7) and pDPG480 (FIG. 3, 35S-mtlD-Tr7). The cells were left on the solid Medium 279 for 4 days and then put into liquid Medium 401. Liquid selection was started after one passage (3.5 days) using 1 mg/L bialaphos. Cells were thin plated one week later at 0.1 ml PCV (2 weeks after bombardment) on to Medium 279+ 3mg/L bialaphos. Putative transformants were observed about 8 weeks later. A total of 46 bialaphos-resistant lines and 25 lines containing mtlD DNA, as determined by a polymerase chain reaction, were obtained.

Transformation of Cell Line AT824 Using Bialaphos Selection Following Particle Bombardment—Solid Medium Selection Cells were bombarded as described above, except the gold particle-DNA preparation was made using 25 μl pDPG319 DNA (bar gene and aroA expression cassette containing the α-tubulin promoter). Following particle bombardment cells remained on solid Medium 279 in the absence of selection for one week. At this time cells were removed from solid medium, resuspended in liquid Medium 279, replated on Whatman filters at 0.5 ml PCV per filter, and transferred to Medium 279 containing 1 mg/L bialaphos. Following one week, filters were transferred to Medium 279 containing 3 mg/L bialaphos. One week later, cells were resuspended in liquid Medium 279 and plated at 0.1 ml PCV on Medium 279 containing 3 mg/L bialaphos. Nine transformants were identified 7 weeks following bombardment.

Transformation of Hi-II callus using Bialaphos Selection Following Particle Bombardment.

Hi-II callus was initiated and bombarded as described above. Four filters were bombarded with pDPG165 FIG. 2, (35S-bar-Tr7) and pDPG493 (FIG. 4, 35S-mtlD-Tr7). After bombardment, cells were allowed to recover on solid media for 3 days. The four original bombarded filters were transferred to Medium 201 containing 1 mg/L bialaphos for 2 weeks. After this time, cells were removed from solid medium, resuspended in liquid medium, replated on Whatman filters at 0.5 ml PCV per filter, and transferred to Medium 201 containing 1 mg/L bialaphos. Following 2–3 weeks, cells were resuspended in liquid medium and plated at 0.1 ml PCV on Medium 201 containing 3 mg/L bialaphos. Putative transformants were visible about 5–6 weeks after thin plating. There were 8 bialaphos-resistant lines, and out of these 4 transformants contained mtlD DNA, as determined by PCR.

Another consideration is that plants may need to have very high levels of osmoprotectant to show a significant change in stress resistance. Thus, a combination of mtlD constructs with different promoters was transformed into Hi-II callus, and mtlD PCR⁺ transformants were obtained. Southern and PCR analysis can determine which mtlD constructs have been incorporated into which transformants.

Transformation of Immature Embryos of the Genotype Hi-II Using Bialaphos as a Selective Agent Following Particle Bombardment.

Immature embryos of the genotype Hi-II were bombarded as described above using pDPG670 (H3C4-adhI-bar-Tr7) and pDPG598 (ActI-mtlD-Tr7). Embryos were allowed to recover on high osmoticum medium (Medium 201+12% sucrose +100 μM AgNO₃) for about 1–3 days, preferably at least overnight, i.e., for about 16–24 hours, and were then transferred to selection medium containing 1 mg/l bialaphos (Medium 201+1 mg/l bialaphos +100 μM AgNO₃). Embryos were maintained in the dark at 24° C. After two to four weeks on the initial selection plates about 50% of the embryos had formed Type II callus and were transferred to selective medium containing 3 mg/l bialaphos (Medium 201+3mg/L bialaphos). Responding tissue was subcultured about every two weeks onto fresh selection medium (Medium 201+3mg/L bialaphos). Six bialaphos-resistant lines were recovered from this experiment.

If cells are producing too much mannitol at the callus level, there may be possible cell death due to swelling or bursting. Immature embryo transformation experiments have been conducted using a low level of mannitol during selection. It is possible that osmoticum in the medium may counteract mannitol producing cells to make a more isotonic environment. It may be possible to obtain high mtlD expressing transformants by doing so.

EXAMPLE V

Plants From Transformed Cells

For use in agriculture, transformation of cells in vitro is only one step toward commercial utilization of these genotypically new plant cells. Plants must be regenerated from the transformed cells, and the regenerated plants must be developed into full plants capable of growing crops in open fields. For this purpose, fertile corn plants are required. The following protocol describes a method for regenerating plants, but one of skill in the art will be familiar with other equally efficient protocols.

During suspension culture development, small cell aggregates (10–100 cells) are formed, apparently from larger cell clusters, giving the culture a dispersed appearance. Upon plating these cells to solid media, somatic embryo development can be induced, and these embryos can be matured, germinated and grown into fertile seed-bearing plants. The characteristics of embryogenicity, regenerability, and plant fertility are gradually lost as a function of time in suspension culture. Cryopreservation of suspension cells arrests development of the culture and prevents loss of these characteristics during the cryopreservation period.

Regeneration of AT824 Transformants and HiII callus

Transformants were produced as described above. For regeneration tissue was first transferred to solid Medium 223 or Medium 201+1 mg/L, bialaphos and incubated for two weeks. Transformants can be initially subcultured on any solid culture that supports callus growth, e.g., Medias 223, 425, 409, and the like. Subsequently transformants were subcultured one to three times, but usually twice on Medium 189 (first passage in the dark and second passage in low light) and once or twice on Medium 101 in petri dishes before being transferred to Medium 607 in Plant Cons©. Variations in the regeneration protocol are normal based on the progress of plant regeneration. Hence some of the transformants were first subcultured once on Medium 425, twice on Medium 189, once or twice on Medium 101 followed by transfer to Medium 501 in Plant Cons©. As shoots developed on Medium 101, the light intensity was increased by slowly adjusting the distance of the plates from the light source located overhead. All subculture intervals were for about 2 weeks at about 24° C. Transformants that developed 3 shoots and 2–3 roots were transferred to soil.

Plantlets in soil were incubated in an illuminated growth chamber and conditions were slowly adjusted to adapt or condition the plantlets to the drier and more illuminated conditions of the greenhouse. After adaptation/conditioning in the growth chamber, plants were transplanted individually to 5 gallon pots of soil in the greenhouse.

EXAMPLE VI

Determination of MDH Activity

Mannitol-1-P Dehydrogenase (MDH) Spectrophotometric Assay

The MDH assay has been used to determine if there is expression of the mtlD gene in transformed callus or leaf tissue. The spectrophotometer measures differences at the 340 nm wavelength, looking for a change from NAD⁺ to NADH, a result of expression of the mtlD gene changing mannitol-1-phosphate to fructose-6-phosphate.

Bacterial extracts are used as controls. An aliquot of the glycerol stocks of bacteria containing the bar gene (p165) or containing the mtlD gene (p480) was put into LB media (100 mg/L ampicillin). These cultures are grown overnight at 37° C. The next day cultures are spun down at 5,000 rpm for 5 minutes. The pellet is rinsed with either Tris-citrate (0.1 M Tris-citrate, pH 8.5) or PAT buffer (50 mM Tris-HCl, pH. 7.5, 2 mM EDTA, 0.15 mg/ml leupeptin, 0.15 mg/ml PMSF, 0.3 mg/ml BSA, 0.3 mg/ml DTT)and spun down again. Then the pellet, about 200 µl of glass beads, and 500 µl of buffer are put into a 1.5 ml eppendorf tube and shaken twice for 20 seconds on "high" (MINI-BEADBEATER™, Biospec Products). The tubes are then spun down and the supernatant is used for the assay. All tubes are kept on ice.

For callus or plant extracts, about 0.5 g of tissue is used. Tissue is homogenized with approximately 250 µl of Tris-citrate or PAT buffer. Extracts are spun down in the microfuge at 14,000 rpm for 5 minutes. Protein is quantified using the BioRad assay.

For the MDH assay, a master assay mix is made to be used for all the samples. The mix includes: 2.5 ml 0.1 M Tris-citrate, pH 8.5, 0.1 ml of 4 mM $NAD^+$ (dissolve one 20 mg vial of SIGMA, β-nicotinamide adenine dinucleotide, in 7.15 ml dd$H_2O$), and 0.1 ml of 6 mM mannitol-1-phosphate (SIGMA)).

The spectrophotometric readings were done as follows: 1 ml of assay mix was put into a cuvette. Then 2–100 µg of protein was added. The cuvette was inverted about 3 times and then the reading was initiated. Measurements were taken for up to 5 minutes at 340 nm.

Bioassays for mannitol

Callus assays were conducted on transformants derived from AT824 (S80HO-52) and Hi-II callus (HC05II-55), as well as on controls. Callus growth assays were started by plating 0.1–0.5 g callus fresh weight on to Whatman filters. Filters were then put on to media with additional concentrations of osmoticum. The osmoticum includes mannitol (0, 0.3, 0.6, 0.9 M) and NaCl (0, 50, 150, 250 mM). Fresh weight gains were taken after 2–3 weeks in culture.

To determine if there is a significant amount of mannitol being produced at the callus level, osmotic potential readings can be conducted on 0.1 g callus samples using the Psychrometer (Wescor Inc. C-52 sample chambers) by methods well known to the art.

EXAMPLE VII

Transformant Plants into the Greenhouse and Characterization of $R_0$ Plants

Once plants are regenerated, hardened off in the growth chamber, plants are transferred to the greenhouse to obtain seed. Leaf samples are taken of the $R_0$ plants as well as subsequent generations and crosses and endogenous mannitol levels are determined. Phenotypic changes in the plants possessing the transgene were documented.

To determine the mannitol content of these plants, approximately 30 grams (fresh weight) of the tip of mature, healthy leaves are sampled. The leaf samples are placed in 50 ml polypropylene test tubes in a −70° C. freezer. Frozen leaf samples are then dried in a freeze drier and stored until analysis. In separate 50 ml polypropylene test tubes, 1.0 to 1.5 gram quantities of dried leaf sample are weighed. The samples are then homogenized in 40 mls of 80% ethanol (v/v) using a Polytron. The resulting solutions are incubated in a 72° C. water bath for 30 minutes, with a brief vortexing step at approximately 15 minutes. Following the incubation, the solutions are heated in a boiling water bath for 2 minutes. The samples are then centrifuged at 3000xg for 15 minutes. The resulting supernatants are then recovered and taken to dryness overnight in a 40° C. nitrogen evaporator. The remaining paste is frozen then freeze-dried for approximately 2 hours. The dried material is dissolved in 0.5 mls of distilled, deionized water to form the aqueous simple carbohydrate extract. The extract is purified prior to HPLC separation techniques by passing it through a C-18 solid phase extraction column (Varian Bond Elut®) and a 1.2 micron acrodisc filter.

Mannitol content of the simple carbohydrate extracts are determined using HPLC separation techniques. An RCM monosaccharide column (Phenomenex®) is used, with water as the mobile phase. The separated simple sugars are detected with an Erma® ERC-7512 refractive index detector. The resulting sample chromatograms are analyzed using Maxima® peak integration software and compared to chromatograms of mannitol standards.

The above procedure for mannitol extraction and quantification from corn leaf material was tested using a plant species which was known to possess naturally occurring endogenous levels of mannitol. Extracts were prepared from leaves, roots, small stems, and large stalks of the celery plant. All four extracts were found to possess detectable levels of mannitol. Based on chromatograms obtained from standards, the amount of mannitol in the tissue was estimated to be between 20 mg (roots) to 112 mg (stems) per gram of dry weight.

During the mid vegetative stage of development, greenhouse grown $R_0$ maize plants were sampled for leaf mannitol content, according to the above described procedure. Over a 10 month period, leaf samples from one hundred four $R_0$ plant clones from seventeen callus cell lines were assayed. Carbohydrate extracts of $R_0$ clones from several cell lines were found to exhibit HPLC chromatograms which contained peaks with retention times similar to mannitol standards. Although leaf samples from most of the cell lines expressed relatively small amounts of leaf tissue mannitol, those derived from two cell lines were found to express putative levels of mannitol which were over 3.0 milligrams per gram of dry weight (mg/g dry wt.). Addition of mannitol to the extracts resulted in an increase in the area of the "mannitol" peak without the production of any new peaks. Levels of leaf tissue mannitol in $R_0$ clones ranged from 19.31 mg/g dry wt. for the cell line HCO5II-55 (derived from Hi-II callus) to 3.63 mg/g dry wt. for the cell line S80HO-52 (derived from AT824).

Transformation Using the Glb1 promoter

Transformed plant cell lines derived from AT824 suspension (S87KM) and immature embryos (HI68KM) which were $PCR^+$ for the pDPG586 construct have been in regeneration. The pDPG586 vector is potentially sensitive to ABA induction at the callus level due to the presence of the Glb1 promoter. Moreover, levels of ABA are increased in drought sensitive plants during a period of drought (Landi et al., *Maydica*, 40 (1995)), indicating that an ABA inducible promoter is also drought inducible.

Droughted pDPG586-containing transgenic plants are tested for the production of ABA and for increased levels of mannitol. HPLC analyses showed low levels of mannitol in leaf tissue from these plants. Young transgenic seedlings are exposed to ABA and differences in mannitol expression determined at later plant stages. MDH assays are conducted on ABA treated callus from tissue transformed with this construct. Seed viability after drought is also tested to determine whether mannitol is expressed in the embryo.

Transformation Using the Maize Transit Peptide (MZTP)

The MZTP was used to express mtlD in the chloroplast. Increased mtlD expression in the chloroplast can give protection to the chloroplastic photosynthetic system under reduced water availability conditions. The expression of mtlD thus allows the chloroplast to osmotically adjust to the cellular conditions that change as a result of changes in the water relations in the plant. In addition, if mannitol is expressed exclusively in the cytosol, some disruption of chloroplast function could occur due to the imbalance of osmotic relations between the compartments of the cell. Moreover, increased mtlD expression in the chloroplast may also provide anti-oxidant activity.

One construct, pDPG587 (35S-MZTP-mtlD-Tr7 3'), has been tested using AT824 suspension (S85KN, S87KN, S88LG), Hi-II callus (HS06LG, HZ04LG), and immature embryos (HI88LG, HI89LG, HI90LG, IH07LW, DI.04LW, IH16LW, CS12LW, DT01LW). PCR$^+$ transformants with the construct were obtained. Furthermore, the presence of mannitol was detected in transformants containing the (35S-MZTP-mtlD-Tr7 3') expression cassette.

Chloroplast viability assays, magnetic isolation of chloroplasts, and greenhouse and field studies of the resultant transformed plants under a range of water stress or non-stress conditions are performed, by methods described herein or by other methods well known to the art.

EXAMPLE VIII

Characterization of $R_1$ Transformants

Seed were recovered from several outcrosses of S80HO-52 and HCO5II-55 $R_0$ plants. The first $R_1$ seed became available from the outcrosses involving S80HO-52 X AW. The $R_1$ seed was evaluated in three separate greenhouse plantings.

The first planting of twenty-two $R_1$ seeds resulting from the cross of S80HO-5207 X AW were planted in the greenhouse to compare results from HPLC determined leaf tissue mannitol levels to PCR-derived data. The carbohydrate profiles obtained from the twenty-two plants revealed twelve as expressing levels of mannitol comparable to the $R_0$ plant. The results were found to agree with the PCR data developed from the same set of plants.

A second, larger, planting of $R_1$ populations was made in the greenhouse after additional seed became available. The planting included eight populations from various outcrosses of S80HO-52 $R_0$ plants to AW. Twenty seeds were planted per population among ten 15-gallon pots, two seeds from the transgenic population per pot plus the common tester, AW. Therefore, a total of three plants per pot were planted. During the mid-late vegetative stage of development a drought episode was imposed on the plants for 33 days. During midday and predawn sampling periods, several whole plant physiological measurements were collected when appropriate, including the following: 1. water relations parameters (under water stress and rewatered conditions), 2. gas exchange measurements, 3. leaf temperature, 4. leaf mannitol samples, 5. plant height, 6. flowering synchrony, and 7. Glufosinate® sensitivity test.

All populations exhibited approximately a 1:1 segregation for Glufosinate® sensitivity. No visual, morphological differences were observed between plants which were resistant to Glufosinate® (and presumably possessed the preselected DNA segment) and those which were sensitive. This indicates that no deleterious effect on plant growth and development occurred with the mtlD gene at this level of expression.

Data from the twenty plants evaluated among each population were sorted by resistance versus sensitivity to Glufosinate®, then mean values were generated. In all populations, expression of leaf tissue mannitol, as determined by HPLC, co-segregated with expression of Glufosinate® resistance. Levels of leaf tissue mannitol were found to approximate levels expressed in the $R_0$ plants.

Figure 7B:
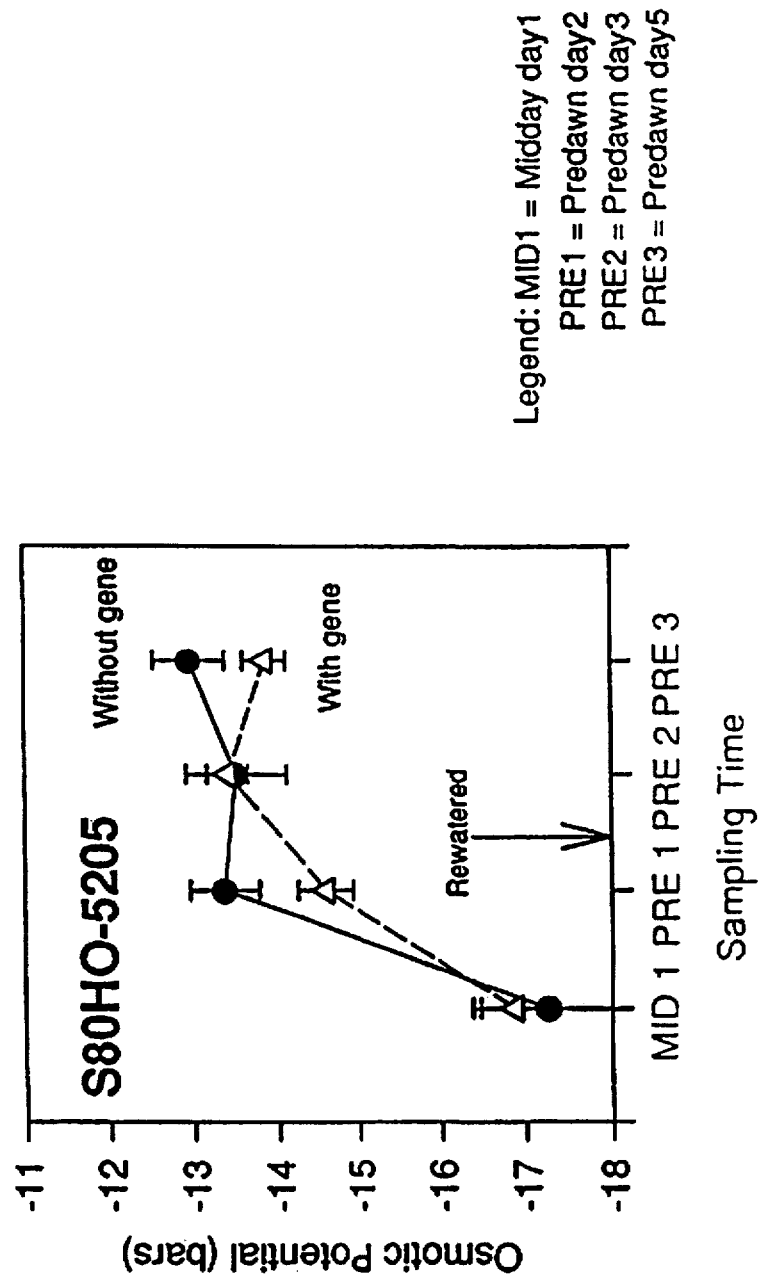
FIG. 7. A time course of leaf osmotic potential values collected from a population of transgenic maize plants. All plants were derived from AT824 cells bombarded with pDPG165 and pDPG480 which were subsequently selected on bialaphos-containing medium. (A) S80HO-5201, (B) S80HO-5205, and (C) S80HO-5208.

A time course of leaf osmotic potential values collected from the S80HO-5201, -5205, and -5208 populations was assembled from the water relations data (FIG. 7). With the exception of 1 sampling period in the -5205 population, plants which exhibited resistance to Glufosinate® applications were found to express more negative predawn osmotic potential values when compared to plants which were Glufosinate® sensitive. However, to fully understand the influence of increased leaf tissue solutes (such as mannitol) on osmotic potential, the influence of tissue dehydration due to drops in total water potential must be examined.

During the first predawn sampling period, total water potential values were between -1.0 to -2.0 bars. No differences were observed between plants with and without the gene. Plants were rewatered prior to the second and third predawn sampling period, which brought the total water potential values to -0.2 bars. When the total water potentials approach zero, the osmotic potentials are directly comparable since the water content is similar. This indicates that differences in osmotic potential values were influenced only by differences in accumulated cell solutes and not by dehydration. During the midday sampling period, total water potential values were between -10.0 to -15.0 bars, indicating that tissue dehydration occurred. As shown in FIG. 7, there were no differences in leaf osmotic potential among any of the populations during the midday period.

Midday gas exchange data, leaf rolling observations, plant heights, and anthesis to silking intervals were also collected in all of the eight $R_1$ populations. No statistically significant differences were observed between plants with and without the gene for any of these measurements. This indicates that at this level of mannitol expression, no deleterious effect on the transgenic plants was noted.

The osmotic potential findings in this experiment represented the first direct link between gene induced leaf mannitol expression and a significant whole plant physiological trait related to drought tolerance.

EXAMPLE IX

Evaluation of the Two Highest Expressing Mannitol Cell Lines, S80HO-5201XAW and HCO5II-5503 XAW In a third greenhouse planting one $R_1$ population was included from each of the two highest mannitol expressing cell lines. Twenty seeds from each of the populations S80HO-5201 X AW and HCO5II-5503 X AW were grown to the mid vegetative stage of development. Plant production and arrangement in the greenhouse was similar to that described above in Example VIII. LH132 was used as the common tester. Therefore a total of three plants per pot were planted. A drought episode was then imposed on half of the twenty plants from each population. During midday and predawn sampling periods, the same whole plant physiological measurements used in the previous $R_1$ experiment were collected. All populations exhibited approximately a 1:1 segregation for Glufosinate® sensitivity. Data from the ten plants evaluated among each population/treatment combination were sorted by resistance versus sensitivity to Glufosinate®, then mean values were generated.

Leaf tissue mannitol, as determined by HPLC, was measured once during the predawn sampling period. In both populations, expression of mannitol co-segregated with expression of Glufosinate® resistance. As was found in the $R_0$ plants, $R_1$ plants from the cell line HCO5II-55 expressed leaf tissue mannitol levels which were approximately 8 times higher than $R_1$ plants from the cell line S80HO-52 (Table 2). Among both populations, plants which were exposed to the drought stress conditions expressed higher levels of leaf tissue mannitol than plants grown under well watered conditions.

TABLE 2

Predawn leaf mannitol content (mg/g dry wt.) in two cell lines.

| TREATMENT | GLUFOSINATE ® RESISTANT | GLUFOSINATE ® SENSITIVE |
|---|---|---|
| | HCO5II-5503 X AW | |
| Stressed | 39.8 | 0.0 |
| Watered | 8.1 | 0.0 |
| | S80HO-5201 X AW | |
| Stressed | 5.1 | 0.0 |
| Watered | 1.1 | 0.0 |

Water relations data collected at 2 time periods prior to the rewatering of plants for the HCO5II-55 and S80HO-52 populations are shown in Tables 3–6. In the HCO5II-55 population, significant ($P \leq 0.05$) differences were observed between plants which were resistant to Glufosinate® compared to plants which were not for both predawn and midday osmotic and turgor potential values. Among the S80HO-52 population, significant ($P \leq 0.05$) differences were observed between Glufosinate® resistant and sensitive plants for predawn osmotic potential values, but not during the midday period.

TABLE 3

Leaf water relations during the predawn period for HCO5II-5503 X AW Glufosinate ® resistant and susceptible plants grown under water stress and watered conditions.

| | GLUFOSINATE ® | PREDAWN PERIOD | | |
|---|---|---|---|---|
| TREATMENT | RESISTANCE | TOTAL | OSMOTIC | TURGOR |
| | | bars | | |
| Stress | No | −12.49 | −14.99 | 2.51 |
| Stress | Yes | −11.73 | −16.93* | 5.20* |
| P($\leq$) | | ns | 0.05 | 0.05 |
| Watered | No | −0.20 | −11.68 | 11.48 |
| Watered | Yes | −0.20 | −12.70 | 12.50 |
| P($\leq$) | | ns | ns | ns |

TABLE 4

Leaf water relations during the midday period for HCO5H-5503 X AW Glufosinate ® resistant and susceptible plants grown under stress and watered conditions.

| | GLUFOSINATE ® | MIDDAY PERIOD | | |
|---|---|---|---|---|
| TREATMENT | RESISTANCE | TOTAL | OSMOTIC | TURGUR |
| | | bars | | |
| Stress | No | −16.21 | −16.14 | −0.07 |
| Stress | Yes | −14.93 | −18.94* | 4.01* |
| P($\leq$) | | ns | 0.05 | 0.05 |
| Watered | No | −4.90 | −13.57 | 8.67 |
| Watered | Yes | −5.13 | −14.25 | 9.12 |
| P($\leq$) | | ns | ns | ns |

TABLE 5

Leaf water relations during the predawn period for S80HO-5201 X AW Glufosinate ® resistant and susceptible plants grown under watered stress and watered conditions.

| | GLUFOSINATE ® | PREDAWN PERIOD | | |
|---|---|---|---|---|
| TREATMENT | RESISTANCE | TOTAL | OSMOTIC | TURGOR |
| | | bars | | |
| Stress | No | −13.00 | −14.94 | 1.94 |
| Stress | Yes | −15.60* | −16.40* | 0.80 |
| P($\leq$) | | 0.05 | 0.05 | ns |
| Watered | No | −0.20 | −12.58 | 12.38 |
| Watered | Yes | −0.20 | −13.08 | 12.88 |
| P($\leq$) | | ns | ns | ns |

TABLE 6

Leaf water relations during the midday period for S80HO-5201 X AW Glufosinate ® resistant and susceptible plants grown under stress and watered period.

| | GLUFOSINATE ® | MIDDAY PERIOD | | |
|---|---|---|---|---|
| TREATMENT | RESISTANCE | TOTAL | OSMOTIC | TURGOR |
| | | bars | | |
| Stress | No | −15.01 | −15.30 | 0.29 |
| Stress | Yes | −16.37 | −15.62 | −0.74 |
| P($\leq$) | | ns | ns | ns |
| Watered | No | −6.30 | −15.87 | 9.57 |
| Watered | Yes | −6.45 | −16.62 | 10.17 |
| P($\leq$) | | ns | ns | ns |

After rewatering of the drought stressed plants, Glufosinate® HCO5II-55 plants continued to maintain more negative osmotic potential values than Glufosinate® sensitive plants for up to 5 days (Tables 7–8). Osmotic adjustment, as calculated by the difference between rewatered and watered plants was over 4 bars for both sample periods. These are significant changes in osmotic potential levels compared to the plants not having the mtlD gene or expressing mannitol. For the lower mannitol expressing line S80HO-5201, no significant differences were observed for changes in osmotic potential between the Glufosinate® resistant and susceptible plants (Tables 9–10). The contrast between the higher and lower mannitol expressing lines may indicate the range of expression needed to work with in crop improvement.

TABLE 7

Differences in osmotic potential of HCO5II-5503 X AW Glufosinate ® resistant and susceptible plants 12 hours after rewatering.

TIME = 12 hrs Rewatered

| GLUFOSINATE ® RESISTANCE | REWATERED OSMOTIC | WATERED OSMOTIC | DIFFERENCE |
|---|---|---|---|
| | bars | | |
| No | −11.70 | −10.80 | 0.90 |
| Yes | −17.30*** | −11.70 | 5.6 |
| P(≦) | 0.001 | | |

TABLE 8

Differences in osmotic potential of HCO5II-5503 X AW Glufosinate ® resistant and susceptible plants 5 days after rewatering.

| GLUFOSINATE ® RESISTANCE | REWATERED OSMOTIC | WATERED OSMOTIC | DIFFERENCE |
|---|---|---|---|
| | bars | | |
| No | −12.90 | −11.80 | 1.1 |
| Yes | −16.40** | −12.10 | 4.3 |
| P(≦) | 0.01 | ns | |

TABLE 9

Differences in osmotic potential of S80HO-5201 X AW Glufosinate ® resistant and susceptible plants 12 hours after rewatering.

TIME = 12 hrs Rewatered

| GLUFOSINATE ® RESISTANCE | REWATERED OSMOTIC | WATERED OSMOTIC | DIFFERENCE |
|---|---|---|---|
| | bars | | |
| No | −11.73 | −13.02 | −1.29 |
| Yes | −12.20 | −12.89 | −0.69 |
| P(≦) | ns | ns | |

TABLE 10

Differences in osmotic potential of S80HO-5201 X AW Glufosinate ® resistant and susceptible plants 5 days after rewatering.

TIME = 5 days Rewatered

| GLUFOSINATE ® RESISTANCE | REWATERED OSMOTIC | WATERED OSMOTIC | DIFFERENCE |
|---|---|---|---|
| | bars | | |
| No | −12.36 | −12.44 | −0.08 |
| Yes | −13.26 | −12.94 | 0.32 |
| P(≦) | ns | ns | |

Among both populations, no statistically significant differences were observed between plants with and without the gene for midday gas exchange data, leaf rolling observations, plant heights, and anthesis to silking intervals.

On the Glufosinate® resistant HCO5II-55 plants, at flowering and further developing during the grainfill, a leaf speckling which developed into a leaf chlorosis followed by necrosis was observed. This abnormality was observed mainly on plants grown under the well watered treatment. The droughted plants did not exhibit this leaf expression in the upper most leaves after rewatering. Due to drought induced leaf firing and senescence it was not able to read the lower leaves of the stressed plants for the chlorosis or speckling. The symptoms first appeared on the oldest leaves of the plant and progressed to younger leaves prior to the onset of physiological maturity. Other than the leaf chlorosis, the plants were morphologically normal and set seed. This chlorosis may disappear with plants where mannitol accumulation is targeted to the chloroplast.

Seed planted from this cell line has confirmed that this chlorosis first starts in the lower most (oldest) leaves and progresses up the plant as the leaves become older. To determine what the pattern of mannitol accumulation is and if there is a correlation to the occurrence of the chlorosis, leaf samples of the plants from oldest to newest leaves will be analyzed. Also ultrastructural studies are being done through transmission microscopy to see the cellular ultrastructure in the chlorotic areas compared cellular ultrastructure in leaf samples from plants without the gene and to green sectors on leaves of plants having the gene.

EXAMPLE X

Evaluation of Mannitol Expressing Transformants in a Field Environment Under Water Stress and Irrigated Conditions Under field conditions, it is necessary to evaluate the phenotype of plants having different levels of mannitol expression under irrigated and water stressed condition.

Germplasm evaluated were the following: (S80H05201X AW) X BK R2 generation with the mtlD gene; (S80H05201X AW) X BK R2 generation without the gene; (HC05II5503XAW) X BK R2 generation with the gene; and BK, a standard inbred line.

The contribution of different levels of mannitol expression to stress tolerance among R2 generation plants from two mannitol expressing cell lines, S80HO-52 and HCO5II-55, was evaluated. The two segregating populations were derived from crosses of greenhouse grown R1 generation plants, transformed with constructs containing the mtlD gene and the bar gene, crossed to the elite stiff stalk inbred designated BK. Stable transformants were determined by resistance to the herbicide Glufosinate®. Leaf tissue of R1 generation plants contained mannitol concentrations from at least about 5.0 mg/g dry weight, for the low expressing cell line, and up to about 40.0 mg/g dry weight for the high expressing cell line. The R2 generation populations were planted in a modified randomized complete block design with 4 repetitions nested within areas of low and high water supply.

A drought stress episode was successfully maintained in the low water supply plot for a period of 12 days at the mid to late vegetative growth stage. The two populations were treated with a 2% Glufosinate® solution and both populations segregated 1:1 for Glufosinate® resistance. Within each plot, data were collected from both Glufosinate® resistant and sensitive plants. On eight separate dates, during the midday sampling period, measurements of leaf temperature, and associated environmental data, were collected. The eight dates ranged from the early stages of the drought stress to seven days after rewatering. Water relations data were collected on ten separate dates during both predawn and midday sampling periods. During several stressed and rewatered sampling dates, leaf samples were collected for mannitol analysis.

HPLC determinations of leaf tissue mannitol from samples collected 6 days after the drought imposition are shown in Table 11. In both populations, expression of mannitol co-segregated with expression of Glufosinate® resistance. Glufosinate® resistant plants from the cell line HCO5II-55 expressed leaf tissue mannitol levels which were approximately 6–8 times higher than plants from the cell line S80HO-52. In previous greenhouse experiments with R1 plants, Glufosinate® resistant plants which were exposed to drought stress conditions expressed higher levels of leaf tissue mannitol than plants grown under well watered conditions. In this experiment, the drought stress episode had little effect on mannitol levels. In general, the levels of mannitol expressed among Glufosinate® resistant plants in this experiment were less than 20% of the levels observed among the same cell lines grown in the greenhouse. This difference may be the result of the compressed (shortened) growth period associated with the environment employed in this experiment. Expression of the mtlD gene in these transformants was under the transcriptional control of the Cauliflower Mosaic Virus 35S promoter.

The levels of other plant carbohydrates in these lines was also determined. Glucose was the only carbohydrate to exhibit significant ($P \leq 0.05$) differences between Glufosinate® sensitive and resistant plants, i.e., Glufosinate® resistant plants contained higher levels of glucose relative to Glufosinate® sensitive plants. Because glucose is known to have pleiotropic effects in plant cells, it is contemplated that the levels of glucose may need to be moderated in these plants.

TABLE 11

Midday leaf mannitol content of 2 R2 populations grown under watered and drought stressed conditions in Kihei, HI.

| TREATMENT | GLUFOSINATE® RESISTANT | GLUFOSINATE® SENSITIVE |
|---|---|---|
| | (mg/g dry wt.) | |
| | High Expressing Population | |
| Stressed | 5.71 | 0.0 |
| Watered | 5.06 | 0.0 |
| Prob ($\leq$) | ns | ns |
| | Low Expressing Population | |
| Stressed | 0.84 | 0.0 |
| Watered | 1.36 | 0.0 |
| Prob ($\leq$) | 0.01 | ns |

Table 12 shows the water relations results for both populations grown under water stress conditions. The results represent the average of six midday periods collected prior to rewatering and indicated more favorable leaf turgor potential values among plants comprising the mtlD gene compared to plants which do not contain the gene. These differences were observed in both the low and high mannitol expressing populations. The improvements in turgor levels among Glufosinate® resistant plants in both populations were the combined results of improvements in total water potential ($\psi_w$) and osmotic potential ($\psi_s$). Since osmotic potential is influenced by both cellular dehydration and by the active accumulation of solutes, the less negative $\psi_w$ values in the Glufosinate® resistant plants prevented the detection of significant differences for $\psi_s$. However, the combined changes among both $\psi_w$ and $\psi_s$ led to highly significant (P<0.01) improvements in leaf turgor.

TABLE 12

Midday water relations parameters for plants exhibiting resistance and sensitivity to Glufosinate® applications among low and high mannitol expressing R2 populations grown under water stress conditions in Kihei, HI. Results are the average of 6 dates.

| | Low Expressing Population | | High Expressing Population | |
|---|---|---|---|---|
| | Glufosinate® Resistance | | | |
| Water Relations | Resis. | Sens. | Resis. | Sens. |
| | (bars) | | | |
| $\Psi_w$ | −9.25 | −9.73 ns | −8.55 | −9.87*** |
| $\Psi_s$ | −13.03 | −12.73 ns | −12.99 | −12.38 ns |
| $\Psi_p$ | 3.77 | 3.00** | 4.44 | 3.01*** |

**Prob. $\leq$0.05
***Prob. $\leq$0.01

Table 13 shows the predawn water relations results for the plants grown under stress. In the high mannitol expressing population, plants which were resistant to Glufosinate® applications expressed significantly ($P \leq 0.01$) more favorable values for all three water relations parameters. Differences among resistant versus susceptible plants in the low expressing population were not significant.

TABLE 13

Predawn water relations parameters for plants exhibiting resistance and sensitivity to Glufosinate® applications among low and high mannitol expressing R2 populations grown under water stress conditions in Kihei, HI. Results are for one sample date.

| | Low Expressing Population | | High Expressing Population | |
|---|---|---|---|---|
| | Glufosinate® Resistance | | | |
| Water Relations | Resis. | Sens. | Resis. | Sens. |
| | (bars) | | | |
| $\Psi_w$ | −1.2 | −1.2 ns | −0.85 | −1.05*** |
| $\Psi_s$ | −10.69 | −11.03 ns | −10.57 | −9.32** |
| $\Psi_p$ | 9.83 | 9.49 ns | 9.72 | 8.27*** |

**Prob. $\leq$0.05
***Prob. $\leq$0.01

Table 14 shows the predawn water relations results for the same plot collected 24 hours after rewatering. Total water potential differences were eliminated by the rewatering event, however significant differences in osmotic potential remain and, since turgor is calculated from total and osmotic water potentials, the accumulation of mannitol resulted in higher turgor values in the high expressing population. Again, differences among plants in the low expressing population were not significant. The improvements in water relations parameters associated with the presence of the mtlD gene in plants were smaller in magnitude than improvements observed in previous greenhouse studies and may be the result of lower levels of leaf mannitol expression. Because water potential and higher turgor pressure under water stress are correlated with a drought resistant phenotype (Morgan, *Aust. J. Agric. Res.*, 34, 607 (1983)), changes in water relations associated with the presence of the mtlD gene in maize can provide plants with an altered ability to utilize available water.

TABLE 14

Rewatered predawn water relations parameters for plants exhibiting resistance and sensitivity to Glufosinate ® applications among low and high mannitol expressing R2 populations previously grown under water stress conditions in Kihei, HI. Results are for one sample date.

| Water Relations | Low Expressing Population | | High Expressing Population | |
|---|---|---|---|---|
| | Glufosinate ® Resistance | | | |
| | Resis. | Sens. | Resis. | Sens. |
| | (bars) | | | |
| $\Psi_w$ | −0.2 | −0.2 ns | −0.2 | −0.2 ns |
| $\Psi_s$ | −10.77 | −10.82 ns | −10.61 | −9.70** |
| $\Psi_p$ | 10.57 | 10.62 ns | 10.41 | 9.50** |

**Prob. ≦0.05

During the collection of midday water relations data, observations of drought-induced leaf rolling were recorded. In previous field experiments, more favorable water relations parameters among hybrids and inbreds grown under drought stress conditions were correlated with decreases in leaf rolling (flatter leaves). Additionally, less leaf rolling among hybrids have been correlated with higher relative yield under stress. In this study, Glufosinate® resistant plants in both the high and low mannitol expressing populations exhibited highly significant (P≦0.01) decreases in leaf rolling (Table 15.).

TABLE 15

Midday leaf rolling scores for plants exhibiting resistance and sensitivity to Glufosinate ® applications among low and high mannitol expressing populations grown under water stress conditions in Kihei, HI. Results are the average of 5 dates.

| Low Expressing Population | | High Expressing Population | |
|---|---|---|---|
| Glufosinate ® Resistance | | | |
| Resis. | Sens. | Resis. | Sens. |
| 3.8[1] | 3.6*** | 4.1 | 3.6*** |

[1]Score: 1 = Severely rolled leaves to 5 = Flat leaves
***Prob. ≦0.01

Figure 8B:
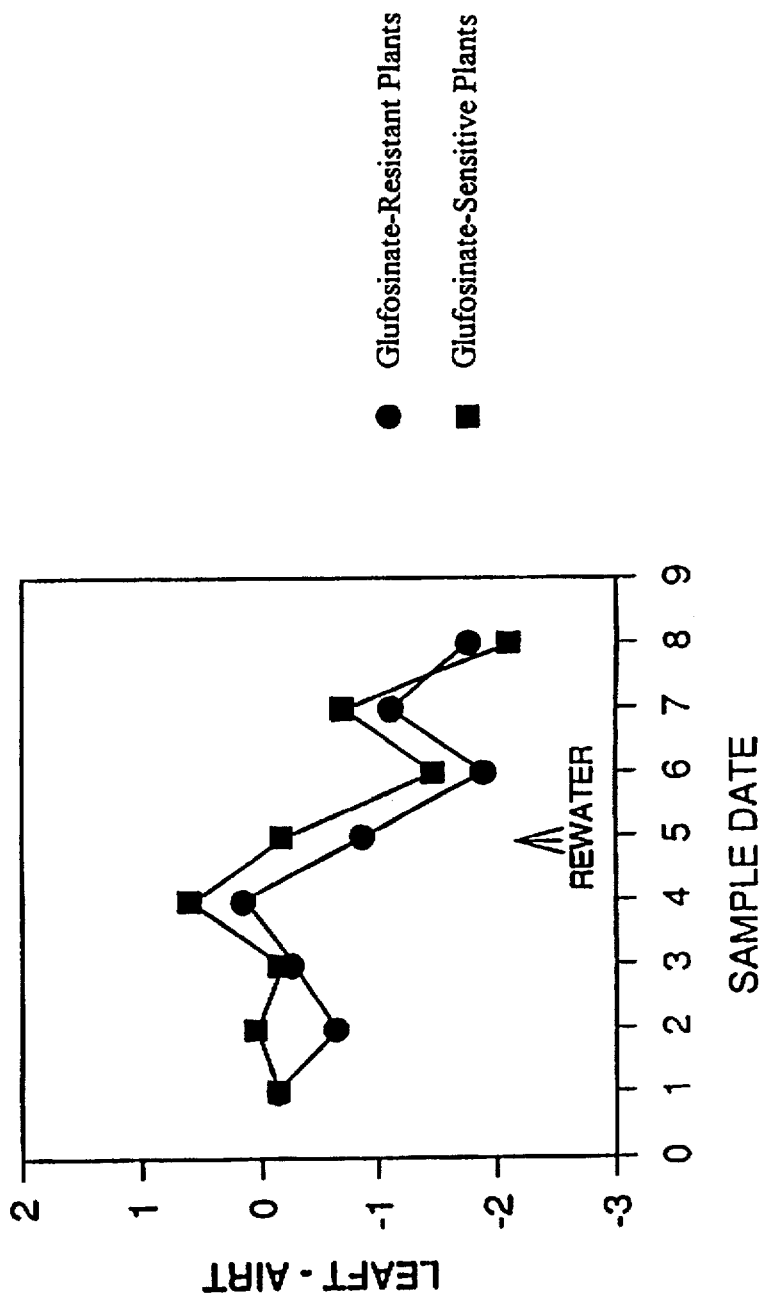
FIG. 8. Leaf temperature data from Glufosinate® sensitive (mtlD negative) and resistant (mtlD positive) plants grown under water stress conditions in the field.

More favorable water relations parameters have also been correlated with higher rates of leaf transpiration and, as a result, cooler leaf temperatures. In one study, leaf temperature data was collected on eight dates. Analysis of the results indicated significantly (P≦0.01) cooler leaf temperatures among plants which possess the mtlD gene compared to plants which did not (FIG. 8). These temperature differences were observed in both the low and high mannitol expressing populations.

The leaf chlorosis symptoms, which were associated with high levels of mannitol expression in greenhouse studies, were observed among both populations in this study. The most severe symptoms were found among Glufosinate® resistant plants in the high expressing population. The degree of leaf chlorosis was more severe than the chlorosis observed in greenhouse grown plants and may have been exacerbated by the high light intensities which occur in the field environment employed in those studies.

Expression of leaf tissue mannitol among both cell lines, co-segregated with expression of Glufosinate® resistance and was lower than that observed in previous greenhouse experiments with R1 plants. Glufosinate® resistant plants from the high mannitol expressing cell line (HCO5II-55) exhibited more favorable turgor potential levels during midday and predawn water stress conditions, and during predawn rewatered conditions. The low mannitol expressing cell line (S80HO-52) exhibited more favorable turgor potential levels during midday stress conditions. Glufosinate® resistant plants from both populations exhibited less leaf rolling and maintained cooler leaf temperatures. The occurrence of mannitol-induced leaf chlorosis was more extensive than in previous greenhouse experiments, and is suspected to be light intensity dependant. Thus, several improvements in whole plant drought tolerance traits were observed in plants co-segregating for Glufosinate® resistance and the mtlD gene. The improvements in water relations parameters, leaf rolling, and canopy temperature (transpiration) are all important factors in drought stress resistance.

EXAMPLE XI

Exposure of Maize Plants Expressing Mannitol to Salt Stress

R3 generation seeds of the high mannitol expressing line (HCO5II-5503) were germinated in paper towels (12 seeds per towel) moistened with water containing 1% Glufosinate® and 1.2 ml/L of DOMAIN (fungicide). Seeds were allowed to germinate at 25° C. for 5 days. The resultant surviving seedlings were transferred to a hydroponics system for further evaluation. Alternatively, seeds can be germinated without Glufosinate® and the segregating population examined.

The hydroponic system consist of tanks which individually hold approximately 4 liters of solution. The individual germinated plants were placed in sponge like material with slits cut to accept the plants and were inserted into holes in the lid of the tank. The planting density was twenty seedlings per tank. The hydroponic solution was described by Clark (*J. Plant Nutrition*, 5, 1039 1982)). The solution was aerated for the duration of the evaluation. For the purposes of a seedling assay generally ¼ or ½ strength Clarks solution is used.

The plants were grown for 6 days, which corresponds to the 2–3 leaf stage of growth in ½ strength Clark's solution in the absence of added NaCl. At this point, the hydroponic solution was changed (½ strength Clark's) and salt (NaCl) added to the solution. Plants were assayed for resistance to 0, 50, 100, 150, 200 and 250 mM NaCl in ½ strength Clark's solution.

At concentrations of NaCl less than 150 mM, no differences in appearance of plant growth (no wilting) were observed after a 24 hour exposure to salt. At 200 mM NaCl, and more particularly at 250 mM NaCl, wilting was observed in the control plants, i.e. same genotype that was used for transformation and not in the transformed mannitol-containing plants. Upon harvest, which is 7 days after the start of the salt stress, determination of osmotic potentials demonstrates that a favorable shift in osmotic potential is associated with the presence of mannitol, resulting in the maintenance of turgor. Salt-stressed mannitol-expressing transformants have significantly more dry matter than controls.

EXAMPLE XII

Exposure of Maize Plants Expressing Mannitol to a Range of Environmental Stresses.

Salt or osmotic stress. Transgenic seeds containing the mtlD gene are germinated in the presence of various salt or osmotically active solutions to determine whether transgenic seeds demonstrate increased tolerance or resistance to salt stress. Alternatively, seedlings can be grown in hydroponic systems and challenged with salt or agents of differing osmotic potentials at different, or all, developmental stages in order to assess the response of mannitol expressing plants to these stresses. Growth and physiological measurements are used to document the differences.

Cold. To demonstrate whether mannitol expression can confer increased germination ability under cool conditions, transgenic seeds containing the mtlD gene are germinated under conditions similar to the standard cold germination test used in the corn industry. Alternatively, transgenic seeds are planted under cool seed bed conditions made cool by artificial environments or naturally cool seed beds in the field. Additionally, plants expressing mannitol are challenged during the grain filling period for cool night time temperatures in order to demonstrate less inhibition of leaf or canopy activity as a result of cold stress during this time of crop development. Young transgenic seedlings are grown at low temperature, such as about 15° C., during the light and dark period. The expression of mannitol in these seedlings allows for increased growth and allows the seedlings to become photosynthetic under such conditions, as well as to survive and grow.

Frost/Freeze. Mannitol expressing plants are assayed for increased freezing tolerance at the seedling stage as well as late season periods. These assays are done in artificial environments to simulate frost or freeze events. Alternatively, seeds are planted outside during times when the naturally occurring environment would impose the stress.

High Heat. Mannitol expressing plants are assayed in artificial environments or in the field in order to demonstrate that the transgene confers resistance or tolerance to heat.

EXAMPLE XIII

Mannitol Expression Causes Yield Increase Under Relatively Non-Stress or More Typical Environment.

Seeds of mannitol expressing corn plants are planted out in test plots and their agronomic performance is compared to standard corn plants using techniques familiar to those of skill in the art. Optionally included in this comparison are plants of similar genetic background without the transgene. A yield benefit is observed and plants exhibiting the increased yield are advanced for commercialization.

Furthermore, transgenic plants with increased levels of mannitol are field tested for agronomic performance under conditions, including, but not limited to, limited and/or adequate water availability. When compared to substantially isogenic nontransgenic plants, mannitol containing plants exhibit higher yield than their nontransgenic counterparts under non-optimal growing conditions.

All publications and patents are incorporated by reference herein, as though individually incorporated by reference. The invention is not limited to the exact details shown and described, for it should be understood that many variations and modifications may be made while remaining within the spirit and scope of the invention defined by the claims.

---

What is claimed is:

1. A method to increase water stress resistance or tolerance in a monocot plant, comprising:
   (a) introducing into cells of a monocot plant an expression cassette comprising a preselected DNA segment comprising an mtlD gene, operably linked to a promoter functional in the monocot plant cells, to yield transformed monocot plant cells; and
   (b) regenerating a differentiated fertile plant from said transformed cells, wherein the mtlD gene is expressed in the cells of the plant so as to render the transformed monocot plant substantially tolerant or resistant to a reduction in water availability that inhibits the growth of an untransformed monocot plant.

2. The method according to claim 1 wherein the expression cassette is introduced into the plant cells by a method selected from the group consisting of electroporation, protoplast transformation, and microprojectile bombardment.

3. The method according to claim 1 wherein the cells of the monocot plant comprise cells of callus, immature embryos, gametic tissue, meristematic tissue or cultured cells in suspension.

4. The method according to claim 1 wherein the expression cassette further comprises a second DNA segment encoding an amino terminal chloroplast transit peptide which is operably linked to the preselected first DNA segment.

5. The method according to claim 4 wherein the second DNA segment encodes a maize chloroplast transit peptide.

6. The method according to claim 4 wherein mannitol-1-phosphate dehydrogenase encoded by the mtlD gene is expressed in the cytosol of the cells of the transformed monocot plant.

7. The method according to claim 4 wherein mannitol-1-phosphate dehydrogenase encoded by the mtlD gene is expressed in the chloroplasts of the cells of the transformed monocot plant.

8. A method to increase salt stress resistance or tolerance in a monocot plant, comprising:
   (a) introducing into cells of a monocot plant an expression cassette comprising a preselected DNA segment comprising an mtlD gene, operably linked to a promoter functional in the monocot plant cells, to yield transformed monocot plant cells; and
   (b) regenerating a differentiated fertile plant from said transformed cells, wherein the mtlD gene is expressed in the cells of the plants so as to render the transformed monocot plant substantially tolerant or resistant to an amount of salt that inhibits the growth of an untransformed monocot plant.

9. The method according to claim 1 or 8 further comprising (c) obtaining progeny from said fertile plant of step (b), which comprise said preselected DNA segment.

10. The method according to claim 9 wherein said progeny are obtained by crossing said fertile plant of step (b) with an inbred line.

11. The method according to claim 9 comprising obtaining seed from said progeny and obtaining further progeny plants comprising said preselected DNA segment from said seed.

12. The method according to claim 11 wherein seeds are obtained from said further progeny plants and plants comprising said preselected DNA segment are recovered from said seed.

13. The method according to claim 10 comprising obtaining seed from said progeny and obtaining further progeny plants comprising said preselected DNA segment from said seed.

14. The method according to claim 13 wherein seeds are obtained from said further progeny plants and plants comprising said preselected DNA segment are recovered from said seed.

15. The method according to claim 10 wherein the progeny obtained in step (c) are crossed back to the inbred line, to obtain further progeny which comprise said preselected DNA segment.

16. The method according to claim 15 wherein said further progeny are crossed back to the inbred line to obtain progeny which comprise said preselected DNA segment.

17. A transformed monocot plant, which plant is substantially tolerant or resistant to a reduction in water availability, the cells of which comprise a recombinant DNA segment comprising a preselected DNA segment comprising an mtlD gene, and wherein the mtlD gene is expressed so as to confer tolerance or resistance to the transformed plant to a reduction in water availability that inhibits the growth of the corresponding untransformed plant.

18. The transformed plant of claim 17 wherein the transformed plant has an improved osmotic potential when the total water potential of the transformed plant approaches zero relative to the osmotic potential of a corresponding untransformed plant.

19. A fertile transgenic *Zea mays* plant comprising a recombinant DNA segment comprising a promoter operably linked to a first DNA segment comprising an mtlD gene, wherein the level of mannitol-1-phosphate dehydrogenase expressed from the mtlD gene in the cells of the transgenic *Zea mays* plant is substantially increased above the level in the cells of a *Zea mays* plant which only differ from the cells of the transgenic *Zea mays* plant in which the recombinant DNA segment is absent, and wherein the recombinant DNA segment is transmitted through a complete normal sexual cycle of the transgenic plant to the next generation.

20. The fertile transgenic *Zea mays* plant of claim 19 wherein the recombinant DNA segment further comprises a second DNA segment encoding an amino terminal chloroplast transit peptide operably linked to the first DNA segment.

21. A seed produced by the transgenic plant of claim 19.

22. A progeny transgenic *Zea mays* plant derived from the seed of claim 21.

23. A progeny transgenic *Zea mays* seed derived from the plant of claim 19.

24. A transformed monocot plant, which plant is substantially salt tolerant or resistant, the cells of which comprise a recombinant DNA segment comprising a preselected DNA segment comprising an mtlD gene, and wherein mannitol-1-phosphate dehydrogenase encoded by the mtlD gene is expressed in an amount effective to confer tolerance or resistance to the transformed plant to an amount of salt that inhibits the growth of the corresponding untransformed plant.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
      ( A ) LENGTH: 41 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:1:

```
GTAACCGCTT ATAAAGCAAT GCAATAATGA GTACTCTGCA G          41
```

( 2 ) INFORMATION FOR SEQ ID NO:2:

( i ) SEQUENCE CHARACTERISTICS:
      ( A ) LENGTH: 31 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:2:

```
GAGTACTCAT TATTGCATTG CTTTATAAGC G                     31
```